(12) United States Patent
Clouser et al.

(10) Patent No.: US 10,692,316 B2
(45) Date of Patent: Jun. 23, 2020

(54) RFID SCANNING DEVICE

(71) Applicant: Gary L Sharpe, Naples, FL (US)

(72) Inventors: Doug Clouser, Galloway, OH (US); Kurt Wolf, Circleville, OH (US); Gary L. Sharpe, Naples, FL (US); Brian Dutro, Dublin, OH (US)

(73) Assignee: Gary L. Sharpe, Naples, FL (US)

( * ) Notice: Subject to any disclaimer, the term of this patent is extended or adjusted under 35 U.S.C. 154(b) by 0 days.

(21) Appl. No.: 15/828,508

(22) Filed: Dec. 1, 2017

(65) Prior Publication Data

US 2019/0340855 A1 Nov. 7, 2019

Related U.S. Application Data

(63) Continuation-in-part of application No. 15/724,218, filed on Oct. 3, 2017, now Pat. No. 10,482,292.
(Continued)

(51) Int. Cl.
*G07C 9/00* (2020.01)
*G16H 40/40* (2018.01)
(Continued)

(52) U.S. Cl.
CPC ...... *G07C 9/00182* (2013.01); *E05B 65/5246* (2013.01); *G06K 7/0008* (2013.01);
(Continued)

(58) Field of Classification Search
CPC .................................................. G07C 9/00182
(Continued)

(56) References Cited

U.S. PATENT DOCUMENTS 4,884,827 A 12/1989 Kelley
4,961,533 A 10/1990 Teller et al.
(Continued)

FOREIGN PATENT DOCUMENTS

CA 2722328 10/2009
CA 2722328 A1 10/2009
(Continued)

OTHER PUBLICATIONS

Barlas, Stephen, "Pharmacy Product Tracing Likely to Go National—Costs to Pharmacies Worrisome", Pharmacy & Therapeutics, Jan. 2009, vol. 34 No. 1, p. 14.
(Continued)

*Primary Examiner* — Allyson N Trail
(74) *Attorney, Agent, or Firm* — Standley Law Group LLP; Jeffrey Standley; Jeffrey Norris

(57) ABSTRACT

Systems, devices and methods for performing inventory management using RFID technology. The system includes a double-door box for receiving one or more items containing RFID tags. Items are scanned against a baseline content data to confirm all items are present and whether any items have expired. The box has security features to prevent unauthorized access to its contents and create an audit trail of access. Access to the box may be granted when two users present separate authorized RFID-enabled cards, wrist bands, or other items. Multiple locking features provide for additional security. A drop box mechanism on top of the housing allows for items to be deposited into the box without the same security protocols needed for accessing items. Scanning, authorization, and notification functions may be controlled remotely by an outside server or locally by a processing unit contained within the box itself.

18 Claims, 45 Drawing Sheets

Related U.S. Application Data

(60) Provisional application No. 62/403,319, filed on Oct. 3, 2016, provisional application No. 62/465,329, filed on Mar. 1, 2017.

(51) Int. Cl.
*E05B 65/52* (2006.01)
*G06K 7/00* (2006.01)
*G06Q 10/08* (2012.01)
*G06K 17/00* (2006.01)

(52) U.S. Cl.
CPC .......... *G06Q 10/087* (2013.01); *G16H 40/40* (2018.01); *G06K 2017/0051* (2013.01); *G07C 2009/0019* (2013.01); *G07C 2009/00269* (2013.01); *G07C 2009/00293* (2013.01)

(58) Field of Classification Search
USPC .................. 235/385, 375, 450, 492, 449
See application file for complete search history.

(56) References Cited

U.S. PATENT DOCUMENTS

| | | | |
|---|---|---|---|
| 5,713,485 | A | 2/1998 | Liff et al. |
| 5,930,145 | A | 7/1999 | Yuyama et al. |
| 5,963,134 | A | 10/1999 | Bowers et al. |
| 5,986,662 | A | 11/1999 | Argiro et al. |
| 6,112,502 | A | 9/2000 | Frederick et al. |
| 6,189,727 | B1 * | 2/2001 | Shoenfeld .............. G07F 13/10 221/2 |
| 6,249,299 | B1 | 6/2001 | Tainer |
| 6,275,157 | B1 | 8/2001 | Mays et al. |
| 6,294,999 | B1 | 9/2001 | Yarin et al. |
| 6,330,351 | B1 | 12/2001 | Yasunaga |
| 6,574,166 | B2 | 6/2003 | Niemiec |
| 6,632,619 | B1 | 10/2003 | Harrison et al. |
| 6,771,369 | B2 | 8/2004 | Rzasa et al. |
| 6,825,864 | B2 | 11/2004 | Botten et al. |
| 6,847,861 | B2 | 1/2005 | Lunak et al. |
| 6,851,615 | B2 | 2/2005 | Jones |
| 6,861,954 | B2 | 3/2005 | Levin |
| 6,877,658 | B2 | 4/2005 | Raistrick et al. |
| 6,879,876 | B2 | 4/2005 | O'Dougherty et al. |
| 6,899,626 | B1 | 5/2005 | Luciano et al. |
| 6,900,021 | B1 | 5/2005 | Harrison et al. |
| 6,933,849 | B2 | 8/2005 | Sawyer |
| 6,935,560 | B2 | 8/2005 | Andreasson et al. |
| 6,952,681 | B2 | 10/2005 | McQuade et al. |
| 6,985,870 | B2 | 1/2006 | Martucci et al. |
| 6,992,574 | B2 | 1/2006 | Aupperle et al. |
| 6,994,249 | B2 | 2/2006 | Peterka et al. |
| 7,028,182 | B1 | 4/2006 | Killcommons |
| 7,036,729 | B2 | 5/2006 | Chung |
| 7,061,831 | B2 | 6/2006 | De La Huerga |
| 7,111,780 | B2 | 9/2006 | Broussard et al. |
| 7,116,343 | B2 | 10/2006 | Botten et al. |
| 7,118,029 | B2 | 10/2006 | Nycz et al. |
| 7,140,542 | B2 | 11/2006 | Andreasson et al. |
| 7,146,247 | B2 | 12/2006 | Kirsch et al. |
| 7,151,456 | B2 | 12/2006 | Godfrey |
| 7,158,030 | B2 | 1/2007 | Chung |
| 7,165,077 | B2 | 1/2007 | Kalies |
| 7,175,081 | B2 | 2/2007 | Andreasson et al. |
| 7,177,721 | B2 | 2/2007 | Kirsch et al. |
| 7,178,729 | B2 | 2/2007 | Shaffer et al. |
| 7,182,256 | B2 | 2/2007 | Andreasson et al. |
| 7,212,100 | B2 | 5/2007 | Terenna |
| 7,212,127 | B2 | 5/2007 | Jacober et al. |
| 7,227,469 | B2 | 6/2007 | Varner et al. |
| 7,232,066 | B2 | 6/2007 | Andreasson et al. |
| 7,253,736 | B2 | 8/2007 | Tethrake et al. |
| 7,256,699 | B2 | 8/2007 | Tethrake et al. |
| 7,263,501 | B2 | 8/2007 | Tirinato et al. |
| 7,264,323 | B2 | 9/2007 | Tainer et al. |
| 7,268,684 | B2 | 9/2007 | Tethrake et al. |
| 7,275,645 | B2 | 10/2007 | Mallett et al. |
| 7,299,981 | B2 | 11/2007 | Hickle et al. |
| 7,316,231 | B2 | 1/2008 | Hickle |
| 7,317,393 | B2 | 1/2008 | Maloney |
| 7,318,529 | B2 | 1/2008 | Mallett et al. |
| 7,339,550 | B2 | 3/2008 | Hayama et al. |
| 7,341,147 | B2 | 3/2008 | Mallett et al. |
| 7,348,884 | B2 | 3/2008 | Higham |
| 7,354,884 | B2 | 4/2008 | Hada et al. |
| 7,362,228 | B2 | 4/2008 | Nycz et al. |
| 7,375,737 | B2 | 5/2008 | Botten et al. |
| 7,394,383 | B2 | 7/2008 | Hager et al. |
| 7,428,980 | B2 * | 9/2008 | Irwin .............. E05G 7/001 232/45 |
| 7,440,818 | B2 | 10/2008 | Handfield et al. |
| 7,446,747 | B2 | 11/2008 | Youngblood et al. |
| 7,454,880 | B1 | 11/2008 | Austin et al. |
| 7,486,188 | B2 | 2/2009 | Van Alstyne |
| 7,492,257 | B2 | 2/2009 | Tethrake et al. |
| 7,492,261 | B2 | 2/2009 | Cambre et al. |
| 7,504,954 | B2 | 3/2009 | Spaeder |
| 7,518,502 | B2 | 4/2009 | Austin et al. |
| 7,518,516 | B2 | 4/2009 | Azevedo et al. |
| 7,551,089 | B2 | 6/2009 | Sawyer |
| 7,559,483 | B2 | 7/2009 | Hickle et al. |
| 7,564,364 | B2 | 7/2009 | Zweig |
| 7,596,427 | B1 | 9/2009 | Frederick et al. |
| 7,630,791 | B2 | 12/2009 | Nguyen et al. |
| 7,639,136 | B1 | 12/2009 | Wass et al. |
| 7,644,016 | B2 | 1/2010 | Nycz et al. |
| 7,672,872 | B2 | 3/2010 | Shanton |
| 7,706,915 | B2 | 4/2010 | Mohapatra et al. |
| 7,706,916 | B2 | 4/2010 | Hilton |
| 7,712,670 | B2 | 5/2010 | Sauerwein, Jr. et al. |
| 7,715,277 | B2 | 5/2010 | De La Huerga |
| 7,724,918 | B2 | 5/2010 | Balakrishnan et al. |
| 7,729,597 | B2 | 6/2010 | Wright et al. |
| 7,734,157 | B2 | 6/2010 | Wright et al. |
| 7,735,732 | B2 | 6/2010 | Linton et al. |
| 7,747,477 | B1 | 6/2010 | Louie et al. |
| 7,752,085 | B2 | 7/2010 | Monroe |
| 7,772,964 | B2 | 8/2010 | Tethrake et al. |
| 7,775,056 | B2 | 8/2010 | Lowenstein |
| 7,783,163 | B2 | 8/2010 | Wright et al. |
| 7,783,174 | B2 | 8/2010 | Wright et al. |
| 7,801,422 | B2 | 9/2010 | Wright et al. |
| 7,815,117 | B2 | 10/2010 | Tuschel et al. |
| 7,834,765 | B2 | 11/2010 | Sawyer |
| 7,834,766 | B2 | 11/2010 | Sawyer |
| 7,837,093 | B1 | 11/2010 | Leu et al. |
| 7,837,107 | B1 | 11/2010 | Leu et al. |
| 7,858,841 | B2 | 12/2010 | Krautkramer et al. |
| 7,860,730 | B1 | 12/2010 | Goodall et al. |
| 7,868,754 | B2 | 1/2011 | Salvat, Jr. |
| 7,893,876 | B2 | 2/2011 | Brown et al. |
| 7,908,030 | B2 | 3/2011 | Handfield et al. |
| 7,918,830 | B2 | 4/2011 | Langan et al. |
| 7,933,033 | B2 | 4/2011 | Ohishi et al. |
| 7,976,508 | B2 | 7/2011 | Hoag |
| 7,985,711 | B2 | 7/2011 | Tohmatsu et al. |
| 7,990,272 | B2 | 8/2011 | Wass et al. |
| 7,996,286 | B2 | 8/2011 | Kreiner et al. |
| 8,002,174 | B2 | 8/2011 | Coyne, III et al. |
| 8,006,903 | B2 | 8/2011 | Braun et al. |
| 8,009,913 | B2 | 8/2011 | Greyshock |
| 8,031,347 | B2 | 10/2011 | Edwards et al. |
| 8,042,738 | B2 | 10/2011 | Cloix |
| 8,049,627 | B1 | 11/2011 | Addante |
| 8,063,925 | B2 | 11/2011 | Tainer et al. |
| 8,065,858 | B2 | 11/2011 | Leu et al. |
| 8,072,635 | B2 | 12/2011 | Roberts et al. |
| 8,077,041 | B2 | 12/2011 | Stern et al. |
| 8,082,192 | B2 | 12/2011 | Nycz et al. |
| 8,099,339 | B1 | 1/2012 | Pinsonneault et al. |
| 8,108,068 | B1 | 1/2012 | Boucher et al. |
| 8,111,159 | B2 | 2/2012 | Andreasson et al. |
| 8,112,175 | B2 | 2/2012 | Handfield et al. |
| 8,131,397 | B2 | 3/2012 | Vahlberg et al. |

(56) References Cited

U.S. PATENT DOCUMENTS

| | | |
|---|---|---|
| 8,154,390 B2 | 4/2012 | Heath et al. |
| 8,160,741 B1 | 4/2012 | Shoenfeld |
| 8,174,392 B1 | 5/2012 | Sagbhini et al. |
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,271,128 B1 | 9/2012 | Schultz |
| 8,272,492 B1 | 9/2012 | Chang |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |
| 8,292,186 B2 | 10/2012 | Deloche et al. |
| 8,296,950 B2 | 10/2012 | Colbrunn et al. |
| 8,313,024 B2 | 11/2012 | Marino |
| 8,319,607 B2 | 11/2012 | Grimlund et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,371,448 B1 | 2/2013 | Reaux |
| 8,376,228 B2 | 2/2013 | DeVet et al. |
| 8,384,545 B2 | 2/2013 | Hussain et al. |
| 8,385,972 B2 | 2/2013 | Bochenko et al. |
| 8,386,070 B2 | 2/2013 | Eliuk et al. |
| 8,394,053 B2 | 3/2013 | Bochenko et al. |
| 8,403,212 B2 | 3/2013 | van Esch |
| 8,403,224 B2 | 3/2013 | Fedorko et al. |
| 8,405,508 B2 | 3/2013 | Burke |
| 8,438,067 B2 | 5/2013 | Omura et al. |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 | 8/2013 | Ross-Messemer |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,589,271 B2 | 11/2013 | Evans |
| 8,593,278 B2 | 11/2013 | Churbock et al. |
| 8,593,678 B2 | 11/2013 | Ohishi et al. |
| D694,817 S | 12/2013 | Adam et al. |
| 8,606,596 B1 | 12/2013 | Bochenko et al. |
| 8,636,202 B1 | 1/2014 | Keefe et al. |
| 8,639,525 B2 | 1/2014 | Levine et al. |
| 8,686,859 B2 | 4/2014 | Hussain et al. |
| 8,699,054 B2 | 4/2014 | Edwards et al. |
| 8,702,674 B2 | 4/2014 | Bochenko |
| 8,723,674 B2 | 5/2014 | Conley et al. |
| 8,749,356 B2 | 6/2014 | Hussain et al. |
| 8,755,056 B2 | 6/2014 | Edwards et al. |
| 8,825,680 B2 | 9/2014 | Burke et al. |
| 8,893,970 B2 | 11/2014 | Keefe et al. |
| 8,922,435 B2 | 12/2014 | Fontecchio et al. |
| 8,935,280 B2 | 1/2015 | Bauman et al. |
| 8,945,066 B2 | 2/2015 | Bochenko et al. |
| 8,948,478 B2 | 2/2015 | Keefe et al. |
| 8,985,388 B2 | 3/2015 | Ratnaker |
| 8,990,099 B2 | 3/2015 | MacDonald et al. |
| 9,004,346 B2 * | 4/2015 | Farentinos ............ A47G 29/30 232/43.3 |
| 9,037,479 B1 | 5/2015 | MacDonald et al. |
| 9,058,412 B2 | 6/2015 | MacDonald et al. |
| 9,058,413 B2 | 6/2015 | MacDonald et al. |
| 9,058,435 B2 | 6/2015 | Keefe et al. |
| 9,171,280 B2 | 10/2015 | Gitchell et al. |
| 9,367,665 B2 | 6/2016 | MacDonald et al. |
| 9,378,484 B1 | 6/2016 | Russell et al. |
| 9,449,296 B2 | 9/2016 | MacDonald et al. |
| 9,539,374 B2 | 1/2017 | Halpern |
| 9,582,644 B2 | 2/2017 | Gitchell et al. |
| 9,734,294 B2 | 8/2017 | MacDonald et al. |
| 9,805,169 B2 | 10/2017 | MacDonald et al. |
| 10,083,766 B2 | 9/2018 | Gitchell et al. |
| 10,210,954 B2 | 2/2019 | Caputo et al. |
| 2001/0053986 A1 | 12/2001 | Dick |
| 2002/0026330 A1 | 2/2002 | Klein |
| 2002/0049650 A1 | 4/2002 | Reff |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0102970 A1 | 6/2003 | Creel et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0055221 A1 * | 3/2004 | Hoffman ................. E05F 1/105 49/386 |
| 2004/0057609 A1 | 3/2004 | Weinberg |
| 2004/0081669 A1 | 4/2004 | Greeven et al. |
| 2004/0158507 A1 | 8/2004 | Meek, Jr. et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0014948 A1 | 1/2005 | Galbo et al. |
| 2005/0060171 A1 | 3/2005 | Molnar |
| 2005/0062603 A1 | 3/2005 | Fuerst et al. |
| 2005/0087544 A1 | 4/2005 | Skavnak |
| 2005/0108044 A1 | 5/2005 | Koster |
| 2005/0125097 A1 | 6/2005 | Chudy et al. |
| 2005/0127176 A1 | 6/2005 | Dickinson et al. |
| 2005/0149378 A1 | 7/2005 | Cyr et al. |
| 2005/0149414 A1 | 7/2005 | Schrodt et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |
| 2006/0152338 A1 | 7/2006 | Hsu |
| 2006/0152364 A1 | 7/2006 | Walton |
| 2006/0152367 A1 | 7/2006 | Narayanaswamy |
| 2006/0208886 A1 | 9/2006 | Beamer |
| 2006/0230072 A1 | 10/2006 | Partovi et al. |
| 2006/0242159 A1 | 10/2006 | Bishop et al. |
| 2006/0267731 A1 | 11/2006 | Chen |
| 2007/0001809 A1 | 1/2007 | Kodukula et al. |
| 2007/0008399 A1 | 1/2007 | Botten et al. |
| 2007/0023512 A1 | 2/2007 | Miller et al. |
| 2007/0023513 A1 | 2/2007 | Andreasson et al. |
| 2007/0074722 A1 | 4/2007 | Giroux et al. |
| 2007/0114279 A1 | 5/2007 | Lessing et al. |
| 2007/0150382 A1 | 6/2007 | Danilewitz |
| 2007/0168228 A1 | 7/2007 | Lawless |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1 | 10/2007 | Swan et al. |
| 2007/0272746 A1 | 11/2007 | Ortiz et al. |
| 2008/0004908 A1 | 1/2008 | Oh et al. |
| 2008/0012687 A1 | 1/2008 | Rubinstein |
| 2008/0045930 A1 | 2/2008 | Makin et al. |

(56) References Cited

U.S. PATENT DOCUMENTS

| | | |
|---|---|---|
| 2008/0046295 A1 | 2/2008 | Albrecht |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0157967 A1 | 7/2008 | Jones et al. |
| 2008/0172253 A1 | 7/2008 | Chung et al. |
| 2008/0184719 A1 | 8/2008 | Lowenstein |
| 2008/0191013 A1 | 8/2008 | Liberatore |
| 2008/0218307 A1 | 9/2008 | Schoettle |
| 2008/0228160 A1 | 9/2008 | Harrison |
| 2008/0243088 A1 | 10/2008 | Evans |
| 2008/0270178 A1 | 10/2008 | McRae et al. |
| 2008/0296373 A1 | 12/2008 | Zmood et al. |
| 2008/0297356 A1 | 12/2008 | Oberle |
| 2008/0306772 A1 | 12/2008 | Shahrokh |
| 2008/0316045 A1 | 12/2008 | Sriharto et al. |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0224891 A1 | 9/2009 | Vishik et al. |
| 2009/0231138 A1 | 9/2009 | Lai et al. |
| 2009/0267740 A1 | 10/2009 | Pizzuto |
| 2009/0267772 A1 | 10/2009 | Dehnadi |
| 2009/0277815 A1 | 11/2009 | Kohl |
| 2009/0294521 A1 | 12/2009 | De La Huerga |
| 2009/0307755 A1 | 12/2009 | Dvorak et al. |
| 2010/0022953 A1 | 1/2010 | Bochenko et al. |
| 2010/0022987 A1 | 1/2010 | Bochenko et al. |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Shiau et al. |
| 2010/0098425 A1 | 4/2010 | Kewitsch |
| 2010/0108761 A1 | 5/2010 | Nycz et al. |
| 2010/0114951 A1 | 5/2010 | Bauman et al. |
| 2010/0176917 A1* | 7/2010 | Bacarella .............. E05B 47/026 340/5.6 |
| 2010/0185458 A1 | 7/2010 | Newcomb et al. |
| 2010/0204659 A1 | 8/2010 | Bochenko et al. |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Louie et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Lambrou et al. |
| 2011/0063091 A1 | 3/2011 | Kang |
| 2011/0068922 A1 | 3/2011 | Ross |
| 2011/0093279 A1 | 4/2011 | Levine et al. |
| 2011/0110568 A1 | 5/2011 | Vesper et al. |
| 2011/0112682 A1 | 5/2011 | Matsukawa et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0187549 A1 | 8/2011 | Balasing |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kaman |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1 | 2/2012 | Hussain et al. |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0130534 A1 | 5/2012 | Wurm |
| 2012/0173440 A1 | 7/2012 | Dehlinger et al. |
| 2012/0177256 A1 | 7/2012 | Keefe et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Stavsky et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0221082 A1 | 8/2013 | Botten |
| 2013/0221087 A1 | 8/2013 | Keefe et al. |
| 2013/0225945 A1 | 8/2013 | Prince et al. |
| 2013/0282438 A1 | 10/2013 | Hunter et al. |
| 2013/0327822 A1 | 12/2013 | Keefe et al. |
| 2014/0060729 A1 | 3/2014 | Srnka et al. |
| 2014/0066880 A1 | 3/2014 | Prince et al. |
| 2014/0117081 A1 | 5/2014 | Jablonski et al. |
| 2014/0136229 A1 | 5/2014 | Levine et al. |
| 2014/0138440 A1* | 5/2014 | D'Ambrosio ........ G06Q 10/087 235/385 |
| 2014/0142975 A1 | 5/2014 | Keefe et al. |
| 2014/0184390 A1 | 7/2014 | Elizondo, II |
| 2014/0184391 A1 | 7/2014 | Elizondo, II |
| 2014/0197954 A1 | 7/2014 | Caputo et al. |
| 2014/0210596 A1 | 7/2014 | Hussain et al. |
| 2014/0262919 A1 | 9/2014 | Hussain et al. |
| 2014/0263614 A1 | 9/2014 | Keefe et al. |
| 2014/0276213 A1 | 9/2014 | Bochenko |
| 2014/0279548 A1 | 9/2014 | Wang et al. |
| 2014/0282197 A1 | 9/2014 | Keefe et al. |
| 2014/0291397 A1 | 10/2014 | Caputo et al. |
| 2014/0316561 A1 | 10/2014 | Tkachenko et al. |
| 2014/0367080 A1 | 12/2014 | Hussain et al. |
| 2014/0372145 A1 | 12/2014 | MacDonald et al. |
| 2015/0058182 A1 | 2/2015 | Kress-Spatz et al. |
| 2015/0115029 A1* | 4/2015 | Rahim ................ G06F 19/30 235/385 |
| 2015/0235005 A1 | 8/2015 | MacDonald et al. |
| 2015/0339622 A1 | 11/2015 | MacDonald et al. |
| 2016/0019367 A1* | 1/2016 | Olson .................. G07F 11/62 700/241 |
| 2016/0132649 A1 | 5/2016 | Gitchell et al. |
| 2017/0061095 A1 | 3/2017 | Waskins et al. |
| 2017/0132734 A1 | 5/2017 | MacDonald et al. |
| 2017/0212993 A1 | 7/2017 | Gitchell et al. |
| 2018/0039758 A1 | 2/2018 | MacDonald et al. |
| 2018/0279781 A1* | 10/2018 | Jeffries ................ A47B 95/02 |
| 2019/0088354 A1 | 3/2019 | Yanowitz et al. |
| 2019/0115098 A1 | 4/2019 | Gitchell et al. |

FOREIGN PATENT DOCUMENTS

| | | |
|---|---|---|
| CA | 2790220 | 6/2013 |
| CN | 102791310 B | 12/2014 |
| IN | 201204914 P4 | 10/2013 |
| WO | 02095675 | 11/2002 |
| WO | 2006135830 | 2/2006 |
| WO | 2006026246 | 3/2006 |
| WO | 2010074781 | 7/2010 |

(56) References Cited

FOREIGN PATENT DOCUMENTS

| WO | 2011115676 | 9/2011 |
| --- | --- | --- |
| WO | 2011150013 | 12/2011 |
| WO | 2013082423 | 6/2013 |
| WO | 2013116873 | 8/2013 |
| WO | 2013134256 | 9/2013 |
| WO | 2014092754 A1 | 6/2014 |
| WO | 2014159928 | 10/2014 |
| WO | 2014189834 | 11/2014 |

OTHER PUBLICATIONS

Belson, D., "Storage, Distribution, and Dispensing of Medical Supplies", CREATE Interim Report Under FEMA Grant EMW-2004-GR-0112, Apr. 21, 2005, pp. 1-36.
Cakici et al., "Using RFID for the management of pharmaceutical inventory-system optimization and shrinkage control", Decision Support Systems, 2011, pp. 842-852.
CPG Sec. 400.210, Radiofrequency Identification Feasibility Studies and Pilot Programs for Drugs, Nov. 2004, Compliance Policy Guide, available at: http://www.fda.gov/ICECI/ComplianceManuals/CompliancePolicyGuidanceManual/ucm074357.htm.
Crash Cart Inventory Checklist, Outpatient Surgery Magazine, Oct. 2004, "Outpatient Surgery", available at: http://www.outpatientsurgery.net/resources/forms/2004/pdf/OutpatientSurgeryMagazine 0410 crashCart.pdf, in 1 page.
Curtin et al., "Making the 'MOST' out of RFID: a research agenda for the study of the adoption, usage and impact of RFID", Information Technology Management, Apr. 2007, pp. 87-110.
Gonzalez, Stephanie, "Health Maintenance System (HMS) Hardware Research, Design, and Collaboration", NASA USRP—Internship Final Report, 2010, pp. 1-20.
Harrop et al., "RFID for Healthcare and Pharmaceuticals, 2008-2018", Securing Pharma, May 2008, pp. 1-12.
Houliston, Bryan, "Integrating RFID Technology into a Drug Administration System", Bulletin of Applied Computing and Information Technology, vol. 3, No. 1, May 2005, pp. 8. Retrieved Sep. 26, 2013 from http://citrenz.ac.nz/bacit/0301/2005Houliston RFID.htm.
Jorgensen et al., "Executable Use Cases: Requirements for a Pervasive Health Care System", IEEE Software, Mar./Apr. 2004, pp. 34-41.
Lai et al., "Enhancing Medication Safety and Reduce Adverse Drug Events on Inpatient Medication Administration using RFID", WSEAS Transactions on Communications, Oct. 2008, vol. 7, No. 10, pp. 1045-1054.
Lampe et al., "The Smart Box Application Model", Advances in Pervasive Computing, 2004, pp. 1-6.
"McKesson's Announces New Touch-Screen Driven Medication Dispensing Solution", Business Wire, Jun. 15, 2009, pp. 2, Available at: http://www.businesswire.com/news/home/20090615005349/en/McKesson-Announces-Touch-Screen-Driven-Medication-Dispensing-Solution#.NR7quPnF 10.
"Medical Packaging Inc. Announces Clear Stem Flag Label System for Ampoules, Vials, and Syringes", Feb. 1, 2006 available at: http://www.medpak.com/v1/news/20060201 CSFLAG.pdf, in 1 page.
O'Driscoll et al., "RFID: An Ideal Technology for Ubiquitous Computing?" Dublin Institute of Technology School of Electronics and Communications Conference Papers, Jan. 1, 2008, pp. 1-17.
Pappu, Ph.D. et al., "RFID in Hospitals: Issues and Solutions" Consortium for the Accelerated Deployment of RFID in Distribution, Sep. 2004, pp. 1-12.
Tzeng et al., "Evaluating the Business Value of RFID: Evidence from Five Case Studies", International Journal of Production Economics, 2008, vol. 112, pp. 601-613.
Wang et al., "Applying RFID Technology to Develop a Distant Medical Care Service Platform", International Journal of Electronic Business Management, 2010, vol. 8, No. 2, pp. 161-170.
O'Connor, "Johnson & Johnson Finds Value in Multiple RFID Apps" (Apr. 23, 2008), retrieved Aug. 21, 2017, 2 pages, available at http://www.rfidjounal.com/articles/pdf?4046.
Collins, "RFID Cabinet Manages Medicine" (Aug. 12, 2004), retrieved Aug. 21, 2017, 1 page, available at http://www.rfidjournal.com/articles/pdf?1081.
O'Connor, Mary Catherine, "To Keep Drugs from Expiring, Hospital Tests Intelliguard System", RFID Journal, Jan. 12, 2011, pp. 3. http://www.rfidjournal.com/articles/view?8123.
Liu et al, "Point-of-Care Support for Error Free Medication Process" (Jun. 25, 2007), retrieved Aug. 21, 2017, 12 pages, available at: http://ieeexplore.ieee.org/document/4438162/.
McCall et al., "RMAIS: RFID-based Medication Adherence Intelligence System" (Aug. 31, 2010), retrieved Aug. 21, 2017, 4 pages, available at http://ieeexplore.ieee.org/document/5627529/.
Tsai et al., "iMAT: Intelligent Medication Administration Tools" (Jul. 1, 2010), retrieved Aug. 21, 2017, 8 pages, available at http://ieeexplore.ieee.org/document/5556551/.
Tsai et al., "Smart Medication Dispenser: Design, Architecture, and Implementation" (Sep. 27, 2010), retrieved Aug. 21, 2017, 12 pages, available at http://ieeexplore.ieee.org/document/5585838/.
Becker et al. SmartDrawer: RFID-Based Smart Medicine Drawer for Assistive Environments,pp. 1-8, PETRA '09, Jun. 9-13, 2009, Corfu, Greece.
Mike Mowry, A Survey of RFID in the Medical Industry With Emphasis on Applications to Surgery and Surgical Devices, MAE188 Introduction to RFID Dr. Rajit Gadh UCLA, Jun. 9, 2008, pp. 1-22, USA.
JD Howard, Implementation of RFID in the Pharmaceutical Industry, Advisor: Dr. Jay Singh, Feb. 2009, pp. 1-11, San Luis Obispo, CA, USA.
Yahia Zare Mehrjerfi, RFID-enabled healthcare systems: risk-benefit analysis, Department of Industrial Engineering, Yazd University, vol. 4 No. 3, 2010, pp. 282-300, Yazd, Iran.
Cakici et al, Using RFID for the management of pharmaceutical inventory—system optimization and shrinkage control, www.elsevier.com, Feb. 5, 2011, pp. 1-11, Rochester, NY, USA.
John Edwards, RFID Smart Shelves and Cabinets, www.rfidjournal.com, Aug. 24, 2009, pp. 1-4, USA.
Bendavid et al., Using RFID to Improve Hospital Supply Chain Management for High Value and Consignment Items, ScieneDirect, Procedia Computer Science 5 (2011) 849-856, Canada.
Wickipedia, Faraday cage, http://wikipedi.org/w/index.php?title=Faraday, Apr. 23, 2018, pp. 1-3.
Floerkemeier et al., The Smart Box Concept for Ubiquitous Computing Environments, Institute for Pervasive Computing Department of Computer Science, pp. 1-4, ETH Zurich, Switzerland.
School of Electrical and Electronic Engineering, Dublin Institute of Technology, RFID: an Ideal Technology for Ubiquitous Computing?, http://arrow.dit.ie/engschcecon, Jan. 1, 2008, pp. 1-17.
Loc Ho et al. A Prototype on RFID and Sensor Networks for Elder Healthcare: Progress Report, Loc Ho, et al., SIGCOMM '05 Workshops, pp. 70-75, Aug. 22-26, 2005, Philadelphia, PA, USA.
C. Saygin, Adaptive Inventory Management Using RFID Data, C. Saygin, Adv Manuf Technol (2007) 32: 1045-1051.
Yannick Meiller et al. Adaptive Knowledge-Based System for Health Care Applications with RFID-Generated information, Elsevier, Decision Support Systems.
AmerisourceBergen Specialty Group Reconfigures Cubixx Medical Cabinet, Pharmaceutical Commerce, Jan. 9, 2011, Posted in Supply Chain/Logistics, Tagged Nov./Dec. 2010.
Malabika Parida et al., Application of RFID Technology for In-House Drug Management System, IEEE, 2012 15th International Conference on Network-Based Information Systems.
Beth Bacheldor, Healthcare Deploys RFID Refrigerated Drug Cabinets, Sep. 24, 2007, RFID Journal.
Beth Bacheldor, Cardinal Health Readies Item-Level Pilot, May 31, 2006, RFID Journal.
Crash Cart Inventory Checklist (Sample), Courtesy of Progressive Surgical Solutions, LLC, Outpatient Surgery Magazine, Oct. 2004.
Data Gathering Developments, Manufacturing Chemist, p. 24, Feb. 2005.
Chia-Chen Chao et al., Determining Technology Trends and Forecasts of RFID by a Historical Review and Bibliometric Analysis from 1991 to 2005, et al., Elsevier, ScienceDirect, 2006.

(56) References Cited

OTHER PUBLICATIONS

Doing the Wave: Inventory Management with RFID, Kathryn Green, Sr. Director Radiology Services and Cardiovascular Diagnostic & Interventional Services, UMass Memorial Medical Center, Worchester, Massachusetts, vol. 15—Issue 9—Sep. 2007.
Mary Cahtherine O'Connor, Drug Distributor Uses RFID to Vend Meds, May 23, 2006, RFID Journal.
Chun-Liang Lai et al.m Enhancing Medication Safety and Reduce Adverse Drug Events on Inpatient Medication Administration Using RFID, WSEAS.
Chih-Peng Lin et al., Fair Sharing Using Real-time Polling Service to Adaptive VBR Stream Transmission in a 802.16 Wireless Networks, Transactions on Communications, ISSN: 1109-2742, Issue 10, vol. 7, Oct. 2008.
Mary Catherine O'Connor, GlaxoSmithKline Tests RFID on HIV Drug, Mar. 24, 2006, RFID Journal.
Carol Humble, RN, How RFID Freed Nurses from the Pain of Inventory Duties, Memorial Health Care System, Chattanooga, TN, vol. 17—Issue 12—Dec. 2009.
Intel & Siemens Launch RFID Blood Bank in Malaysia, Aug. 16, 2007, RFID Journal.
Mary Catherine O'Connor, Interrogators Start to Evolve, Jun. 1, 2006, RFID Journal.
Ergin Erdem et al., Investigation of RFID Tag Readability for Pharmaceutical Products at Item Level, Drug Development and Industrial Pharmacy, 2009; 35(11): 1312-1324.
Andrea Cangialosi et al., Leveraging RFID in Hospitals: Patient Life Cycle and Mobility Perspectives, IEEE Applications & Practice, Sep. 2007.
Jones et al., Marketing Intelligence & Planning: The benefits, challenges and impacts of radio frequency identification technology (RFID) for retailers in the UK., Marketing Intelligence & Planning, vol. 23 Issue: 4, pp. 395-402, Mar. 2005.
Mary Catherine O'Connor, McKesson Starts RFID Pilot for Viagra, Feb. 17, 2005, RFID Journal.
Jerry Fahrni, More RFID Refrigerator Stuff—Cubixx and myCubixx, Sep. 3, 2012.
New RFID Medical Cabinets Deployed at 50 Hospitals, Sep. 17, 2007, RFID Journal.
Mary Catherine O'Connor, Pfizer Using RFID to Fight Fake Viagra, Jan. 6, 2006, RFID Journal.
Elizabeth Wasserman, Purdue Pharma to Run Pedigree Pilot, May 31, 2005, RFID Journal.
Ygal Bendavid et al., Redesigning the Replenishment Process of Medical Supplies in Hospitals with RFID, Business Process Management Journal, (2010), vol. 16, Issue: 6, pp. 991-1013.
Shang-Wei Wang et al., RFID Applications in Hospitals: a Case Study on a Demonstration RFID Project in a Taiwan Hospital, Proceedings of the 39th Hawaii International Conference on System Sciences, 2006.
Mark Roberti, RFID Basics for Health Care: Understanding the Fundamental Concepts That Affect RFID Deployments, RFID Journal presentation, Sep. 17, 2009, The Westin Waltham-Boston, Waltham, MA.
Mark O. Lewis et al., RFID—Enabled Capabilities and Their Impact on Healthcare Process Performance, Jan. 1, 2010, Association for Information Systems AIS Electronic Library (AISeL), ICIS 2010 Proceedings, International Conference in Information Systems.
RFID Medical Cabinets Evaluated in New Benchmark, Sep. 12, 2007, RFID Journal.
Antti Lahtela et al., RFID and NFC in Healthcare: Safety of Hospitals Medication Care, University of Kuopio, Kuopio, Finland, 2008 Second International Conference on Pervasive Computing Technologies for Healthcare, 241-244, IEEE.
RFID and NFC in Healthcare Information Page.
Amitava Dutta et al., RFID and Operations Management: Technology, Value, and Incentives, Production and Operations Management, vol. 16, No. 5, Sep.-Oct. 2007, pp. 646-655.

Ari Juels, RFID Security and Privacy: A Research Survey, IEEE Journal on Selected Areas in Communications, vol. 24, No. 2, pp. 381-394, Feb. 2006.
Christian Floerkemeier et al., The Smart Box Concept for Ubiquitous Computing Environments, Institute for Pervasive Computing, Department of Computer Science, ETH Zurich, Switzerland, Jan. 2004.
Clair Swedberg, Tennessee Hospital Tracks High-Value Items, Aug. 5, 2009, RFID Journal.
Mary Catherine O'Connor, To Keep Drugs from Expiring, Hospital Tests Intelliguard System, Jan. 12, 2011, RFID Journal.
Beth Bacheldor, UCSD Medical Center Expands Its RFID Deployment, Oct. 29, 2008, RFID Journal.
Beth Bacheldor, UMass Med Center Finds Big Savings Through Tagging, Nov. 21, 2007, RFID Journal.
Kinsella, B., Kit Check Announces New RFID Scanning Station, Little Blue Box is Smaller, Lighter, Provided Free for Users, Jun. 2, 2014, 2 pages, Kit Check, webpage includes video link at https://kitcheck.com/2014/06/new-kit-check-smaller-rfid-scanning-station-little-blue-box/.
Inderbir Singh et al., Versatility of Radio Frequency Identification (RFID) Tags in the Pharmaceutical Industry, Instrumentation Science and Technology, 36: 656-663, 2008.
The Orange Book, Approved Drug Products with Therapeutic Equivalence Evaluations, 2018.
Kit Check, Kit Check Installs in One Hour, video link at https://kitcheck.com/learn-more/video/kit-check-installs-in-me-hour/, publication date unknown, accessed Jul. 8, 2019.
Kit Check, Overview, video link at https://www.youtube.com/watch?v=UvNnoZYgGW4, published Oct. 13, 2013.
Kit Check, Wick Video, video link at https://www.youtube.com/watch?v=tDpVoM4iMbl, published Oct. 14, 2013.
Brown, Dennis E., RFID Implementation, McGraw-Hill Communications, 2007, 34 pages (excerpts), The McGraw-Hill Companies.
Glover, Bill et al., RFID Essentials, First Edition, Jan. 2006, 37 pages (excerpts), O'Reilly Media, Inc., Sebastopol, CA.
Bacheldor, Beth, Children's Hospital Boston Joins Others Using RFID to Track Implantables, RFID Journal, Mar. 5, 2008, 3 pages.
U.S. Department of Health and Human Services, Food and Drug Administration, Approved Drug Products with Therapeutic Equivalence Evaluations ("The Orange Book"), 28th edition, 2008, first published in 1980, 1103 pages.
Reexamination Control No. 90014344, Request for Ex Parte Reexamination of U.S. Pat. No. 8,990,099 B2 with Appendices A-D, filed with the USPTO on Jul. 25, 2019, 1387 pages.
Reexamination Control No. 90014345, Request for Ex Parte Reexamination of U.S. Pat. No. 9,058,412 B2 with Appendices A-D, filed with the USPTO on Jul. 26, 2019, 1429 pages.
Reexamination Control No. 90014343, Request for Ex Parte Reexamination of U.S. Pat. No. 9,058,413 B2 with Appendices A-D, filed with the USPTO on Jul. 25, 2019, 1463 pages.
Reexamination Control No. 90014346, Request for Ex Parte Reexamination of U.S. Pat. No. 9,367,665 B2 with Appendices A-D, filed with the USPTO on Jul. 26, 2019, 1477 pages.
Reexamination Control No. 90014347, Request for Ex Parte Reexamination of U.S. Pat. No. 9,805,169 B2 with Appendices A-D, filed with the USPTO on Jul. 29, 2019, 1535 pages.
Case IPR2019-00376, Petition for Inter Partes Review of U.S. Pat. No. 8,990,099 with Exhibits 1001-1011 filed with the USPTO Patent Trial and Appeal Board on Nov. 30, 2018 by Health Care Logistics, Inc., Patent Owner's Preliminary Response filed with the USPTO Patent Trial and Appeal Board on Mar. 8, 2019 by Kit Check, Inc., and Decision Denying Institution of Inter Partes Review entered by the USPTO Patent Trial and Appeal Board on Jun. 4, 2019, 863 pages.
Case IPR2019-00385, Petition for Inter Partes Review of U.S. Pat. No. 9,058,412 with Exhibits 1001-1014 filed with the USPTO Patent Trial and Appeal Board on Nov. 30, 2018 by Health Care Logistics, Inc., Patent Owner's Preliminary Response filed with the USPTO Patent Trial and Appeal Board on Mar. 8, 2019 by Kit Check, Inc., and Decision Denying Institution of Inter Partes Review entered by the USPTO Patent Trial and Appeal Board on Jun. 3, 2019, 2013 pages.

(56) References Cited

OTHER PUBLICATIONS

Case IPR2019-00387, Petition for Inter Partes Review of U.S. Pat. No. 9,058,413 with Exhibits 1001-1014 filed with the USPTO Patent Trial and Appeal Board on Dec. 1, 2018 by Health Care Logistics, Inc., Patent Owner's Preliminary Response filed with the USPTO Patent Trial and Appeal Board on Mar. 13, 2019 by Kit Check, Inc., and Decision Denying Institution of Inter Partes Review entered by the USPTO Patent Trial and Appeal Board on Jun. 7, 2019, 2014 pages.
Case IPR2019-00394, Petition for Inter Partes Review of U.S. Pat. No. 9,367,665 with Exhibits 1001-1014 filed with the USPTO Patent Trial and Appeal Board on Dec. 3, 2018 by Health Care Logistics, Inc., Patent Owner's Preliminary Response filed with the USPTO Patent Trial and Appeal Board on Mar. 13, 2019 by Kit Check, Inc., and Decision Denying Institution of Inter Partes Review entered by the USPTO Patent Trial and Appeal Board on Jun. 11, 2019, 638 pages.
Case IPR2019-00388, Petition for Inter Partes Review of U.S. Pat. No. 9,805,169 with Exhibits 1001-1010 filed with the USPTO Patent Trial and Appeal Board on Dec. 1, 2018 by Health Care Logistics, Inc., Patent Owner's Preliminary Response filed with the USPTO Patent Trial and Appeal Board on Mar. 13, 2019 by Kit Check, Inc., and Decision Denying Institution of Inter Partes Review entered by the USPTO Patent Trial and Appeal Board on Jun. 3, 2019, 625 pages.
Complaint, *Kit Check, Inc.*, Plaintiff, v. *Health Care Logistics, Inc.*, Defendant, Case No. 2:17-cv-1041, United States District Court for the Southern District of Ohio Eastern Division, Dec. 1, 2017, 45 pages.
Defendant's First Amended Answer, Affirmative Defenses, and Counterclaims to Plaintiff's Complaint, *Kit Check, Inc.* v. *Health Care Logistics, Inc.*, Case No. 2:17-cv-01041-ALM-CMV, United States District Court for the Southern District of Ohio Eastern Division, Feb. 9, 2018, 117 pages.
Defendant Health Care Logistics, Inc.'s Motion for Judgment on the Pleadings Pursuant to FED. R. CIV. P. 12(C), *Kit Check, Inc.* v. *Health Care Logistics, Inc.*, Case No. 2:17-cv-01041-ALM-CMV, United States District Court for the Southern District of Ohio Eastern Division, May 25, 2018, 43 pages.
Plaintiff Kit Check, Inc.'s Memorandum in Opposition to Defendant Health Care Logistics, Inc.'s Motion for Judgment on the Pleadings, *Kit Check, Inc.* v. *Health Care Logistics, Inc.*, Case No. 2:17-cv-01041, United States District Court for the Southern District of Ohio Eastern Division, Jun. 29, 2018, 91 pages.
Defendant Health Care Logistics, Inc.'s Reply in Support of Motion for Judgment on the Pleadings Pursuant to FED. R. CIV. P. 12(C), *Kit Check, Inc.* v. *Health Care Logistics, Inc.*, Case No. 2:17-cv-01041-ALM-CMV, United States District Court for the Southern District of Ohio Eastern Division, Jul. 20, 2018, 76 pages.
Joint Claim Construction and Prehearing Statement, *Kit Check, Inc.* v. *Health Care Logistics, Inc.*, Case No. 2:17-cv-01041, United States District Court for the Southern District of Ohio Eastern Division, Sep. 20, 2018, 21 pages.
Plaintiff Kit Check, Inc.'s Opening Claim Construction Brief, *Kit Check, Inc.* v. *Health Care Logistics, Inc.*, Case No. 2:17-cv-01041, United States District Court for the Southern District of Ohio Eastern Division, Nov. 16, 2018, 93 pages.
Defendant Health Care Logistics, Inc.'s Opening Claim Construction Brief, *Kit Check, Inc.* v. *Health Care Logistics, Inc.*, Case No. 2:17-cv-01041, United States District Court for the Southern District of Ohio Eastern Division, Nov. 16, 2018, 307 pages.
Deposition of Jeffrey Fischer, *Kit Check, Inc.* v. *Health Care Logistics, Inc.*, Case No. 2:17-cv-01041, United States District Court for the Southern District of Ohio Eastern Division, Dec. 19, 2018, 86 pages.
Plaintiff Kit Check, Inc.'s Responsive Claim Construction Brief, *Kit Check, Inc.* v. *Health Care Logistics, Inc.*, Case No. 2:17-cv-01041, United States District Court for the Southern District of Ohio Eastern Division, Jan. 3, 2019, 88 pages.
Defendant Health Care Logistics, Inc.'s Response to Plaintiff Kit Check, Inc.'s Opening Claim Construction Brief, *Kit Check, Inc.* v. *Health Care Logistics, Inc.*, Case No. 2:17-cv-01041-ALM-CMV, United States District Court for the Southern District of Ohio Eastern Division, Jan. 3, 2019, 32 pages.
Defendant Health Care Logistics, Inc.'s Motion for Stay, *Kit Check, Inc.* v. *Health Care Logistics, Inc.*, Case No. 2:17-cv-01041-ALM-CMV, United States District Court for the Southern District of Ohio Eastern Division, Jan. 21, 2019, 12 pages.
Opinion & Order, *Kit Check, Inc.* v. *Health Care Logistics, Inc.*, Case No. 2:17-cv-01041, United States District Court for the Southern District of Ohio Eastern Division, Mar. 14, 2019, 17 pages.
Joint Stipulation of Partial Dismissal Without Prejudice, *Kit Check, Inc.* v. *Health Care Logistics, Inc.*, Case No. 2:17-cv-01041, United States District Court for the Southern District of Ohio Eastern Division, Apr. 16, 2019, 2 pages.
Joint Notice Regarding Claim Terms Which No Longer Need to be Construed at Markman, *Kit Check, Inc.* v. *Health Care Logistics, Inc.*, Case No. 2:17-cv-01041, United States District Court for the Southern District of Ohio Eastern Division, Apr. 16, 2019, 2 pages.
Opinion & Order, *Kit Check, Inc.* v. *Health Care Logistics, Inc.*, Case No. 2:17-cv-01041, United States District Court for the Southern District of Ohio Eastern Division, Apr. 29, 2019, 4 pages.
Notice to the Court Regarding PTAB's Decision to Deny Institution on All of Defendant's IPR Petitions, *Kit Check, Inc.* v. *Health Care Logistics, Inc.*, Case No. 2:17-cv-01041, United States District Court for the Southern District of Ohio Eastern Division, Jun. 12, 2019, 120 pages.
Notice of Status of Defendant Health Care Logistics Inc.'s Requests for Inter Partes Review, *Kit Check, Inc.* v. *Health Care Logistics, Inc.*, Case No. 2:17-cv-01041-ALM-CMV, United States District Court for the Southern District of Ohio Eastern Division, Jun. 20, 2019, 3 pages.
Roberti, Mark, RFID Basics for Health Care, Understanding the fundamental concepts that affect RFID deployments, RFID Journal presentation, Sep. 17, 2009, 33 pages, The Westin Waltham-Boston, Waltham, MA.
KitCheck, Bluesight for Controlled Substances Overview, as retrieved Aug. 30, 2018 from https://web.archive.org/web/20180830001131/https://kitcheck.com/learn-more/video/bluesight-for-controlled-substances-overview/, 1 page.
KitCheck, Diversion Events, as retrieved Aug. 30, 2018 from https://web.archive.org/web/20180830001851/https://kitcheck.com/solutions/controlled-substances/diversion-events/, 1 page.
Kitcheck, Security, as retrieved Aug. 30, 2018 from https://web.archive.org/web/20180830000040/https://kitcheck.com/security/, 1 page.
New, et al., "Utilize ADC Transaction Data to Detect Diversion", Oct. 2017, vol. 14, No. 10, pp. 10 as retrieved from https://www.pppmag.com/article/2119, 1 page.
Swedberg, Claire, "Zimmer Ohio in Use RFID to Manage Orthopedic Products", RFID Journal, May 12, 2010, https://www.rfidjournal.com/articles/pdf?7588, 3 pages.
Opinion & Order, *it Check, Inc.* v. *Health Care Logistics, Inc.*, Case No. 2:17-cv-01041, United States District Court for the Southern District of Ohio Eastern Division, Aug. 30, 2019, 26 pages.
Notice of Granting of Three of HCL's Requests for Ex Parte Reexamination with Exhibits A-C, *Kit Check, Inc.* v. *Health Care Logistics, Inc.*, Case No. 2:17-cv-01041, United States District Court for the Southern District of Ohio Eastern Division, Sep. 9, 2019, 61 pages.
Notice of Granting of HCL's Two Remaining Requests for Ex Parte Reexamination with Exhibits A and B, *Kit Check, Inc.* v. *Health Care Logistics, Inc.*, Case No. 2:17-cv-01041, United States District Court for the Southern District of Dhio Eastern Division, Sep. 10, 2019, 48 pages.
Reexamination Control No. 90014346, Office Action dated Dec. 19, 2019 for U.S. Pat. No. 9,367,665, 50 pages.
Reexamination Control No. 90014347, Office Action dated Dec. 19, 2019 for U.S. Pat. No. 9,805,169, 52 pages.

\* cited by examiner

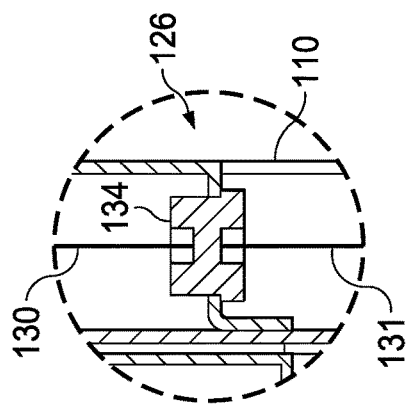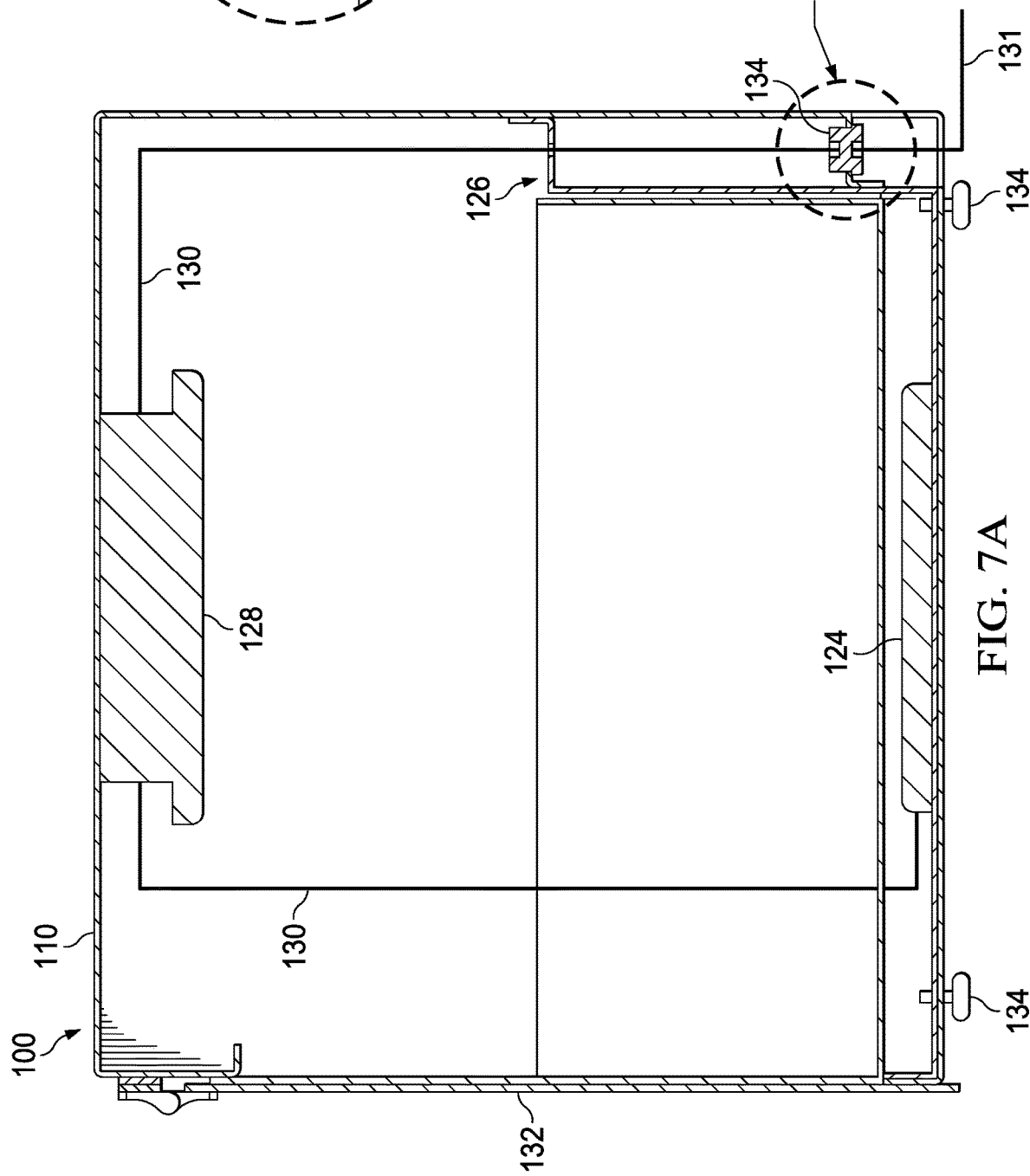

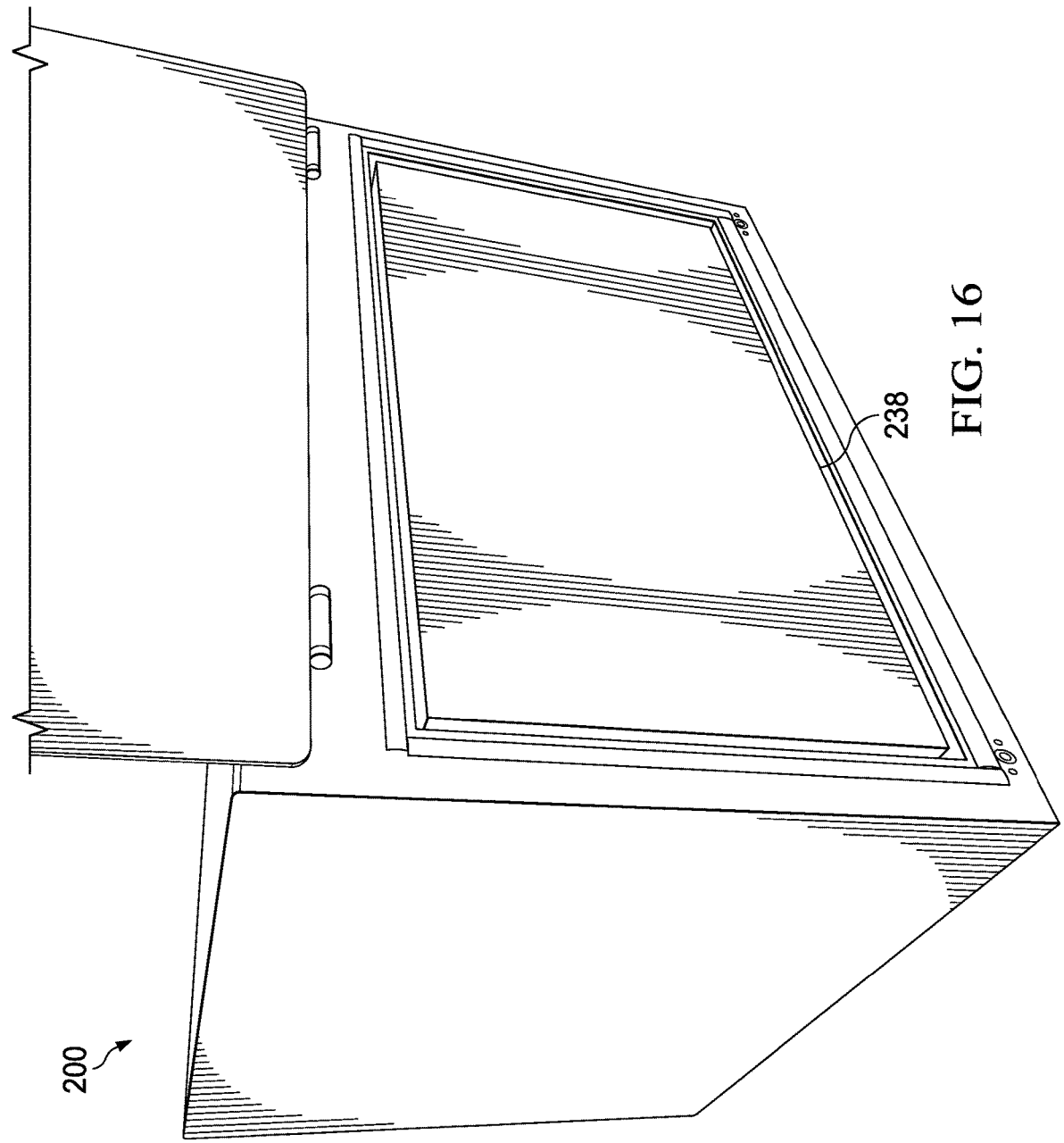

RFID SCANNING DEVICE

CROSS-REFERENCE TO RELATED APPLICATIONS

This non-provisional application is a continuation-in-part of, and claims the benefit of priority to, U.S. Non-provisional application Ser. No. 15/724,218, filed on Oct. 3, 2017, which in turn claims the benefit of priority to U.S. Provisional Application No. 62/403,319 filed Oct. 3, 2016; and U.S. Provisional Application No. 62/465,329, filed Mar. 1, 2017. The contents of these non-provisional and provisional applications are hereby incorporated by references as if fully recited herein.

TECHNICAL FIELD

Exemplary embodiments of the present invention relate generally to RFID scanning systems, devices and methods, and more specifically those used for managing and securing critical inventories, such as medication kits, narcotics, and other prescription drugs.

BACKGROUND OF THE INVENTION

RFID (radio-frequency identification) technology has seen adoption for many uses, such as advertising, transportation, shipping and general inventory management, for instance. Tagging and tracking items with RFID technology in inventory stock is generally done to decrease latency in the reporting of inventory information and to increase the accuracy in the information being reported. In many use cases, the application of RFID technology to inventory management procedures can produce significant gains in a business's efficiency and speed of operations, and further permits the use of electronic tracking and large-scale inventory information analysis often used for further improvements systemically.

RFID technology in general, however, has some disadvantages that can be magnified in certain potential use cases. In some industries, coping with these types of issues has led to a slower rate of deployment of the technology in general. For example, in the medical industry, accuracy of the objects being inventoried (typically medication) is critical.

The medical professionals using the inventoried medication need to consistently have particular medications available to them. Known RFID inventory technology is insufficient, however, due to problem with the labor-intensive creation of such RFID devices, inability to provide bulk scanning, and the actual or potential inaccurate RFID readings due to electromagnetic interference and leakage which can cause inaccuracies in the gathered data.

There is, therefore, an unmet need in the prior art for a highly accurate bulk scanning RFID inventory device that is relatively easy and cost efficient to manufacture. There is also an unmet need for a scanning RFID inventory device that is secure. Pain killers and other medications are commonly subject to theft. Furthermore, there are many settings outside of the traditional hospital or medical office that store medications or supplies. For example, fire stations often store pain killers and/or sedatives for use in their ambulances. There is an increasing amount of theft of pain killers and other medications from fire stations and other facilities. It is, therefore, desirable to have a secure scanning device that limits access to authorized users. It is also desirable to have a scanning device that is compact and can be utilized in a variety of environments without the need for a pharmacy computer or computer station nearby. It is also desirable to have a scanning system that can communicate basic information in a simple way that can be understood by both medical and non-medical personnel.

BRIEF SUMMARY OF THE INVENTION

Exemplary embodiments of the present disclosure pertain to an RFID box that is comprised of a conductive metallic material so as to insulate it from electromagnetic interference. The RFID box comprises a hinged door that is biased open but held shut by latches. Preferably, the door is hinged at the top of the RFID box. The RFID box may comprise an RFID antenna and a RFID antenna/reader, both of which are configured to read RFID tags placed within the RFID box. A pass-through device is preferably located on the rear wall of the RFID box which provides a channel for the passage of a communications wire and power supply.

The box may be formed by one C-shaped enclosure and a pair of open top box shaped side panels such that the enclosure and the side panels form a lip around the front aperture of the RFID box. The hinged door may be hung from the top of the enclosure such that it covers said front aperture when placed in the closed position. A gasket may run the perimeter of the lip to prevent electromagnetic leakage.

The RFID box may be in communication with a remote server and electronic device. The RFID box may transmit baseline data regarding the inventory placed within the RFID box and current content data regarding the inventory current located in the RFID box to the remote server. The remote server may compare the data and send a summary of the comparison to the electronic device.

In an alternative embodiment, the RFID box may comprise a housing surrounding an interior cavity, where the housing has a front side with an aperture for receiving one or more items into said interior cavity. The housing may have a door adapted to move between an open position (allowing access to the interior cavity) and a close position where such access is prohibited. The RFID box may have an antenna and an antenna/reader for communicating with and receiving information from one or more RFID tags located within the interior cavity. The RFID box may have a local processor that is within the housing. The processor may communicate with the antenna and antenna/reader to direct scanning of the items in the interior cavity and obtain RFID information that comprises, among other things, unique identifiers of each of the items. The processor may compare the results of a scan against baseline information previously received to determine if any items are missing and/or expired. The processor may also control access to the box by locking the box until and unless an authorized user, as identified by an RFID bracelet, badge, card, or other item, is recognized by an RFID reader located on the device. The processor may achieve this by being in electronic communication with an access control or audit system comprising one or more lock mechanisms, authentication mechanisms, access control units, and associated communicative coupling means. Magnetic and/or mechanical latches and locks may be used to keep the door securely shut when an authorized user is not accessing the box. The processor may further store access information in local memory and communicate such information to a remote server in order to create an audit trail of users that have obtained access to the interior cavity. Information regarding items scanned and the audit trail may be transmitted to a web portal or to electronic devices. In various embodiments the RFID box may have a variety of shapes and sizes as desired. In some embodiments the RFID box may be sized to receive a single tray of items, such as a crash cart tray, while in other embodiments the RFID box may be sized and shaped to receive multiple trays at the same time. The RFID box may have brackets, tabs, or other features that allow it to be secured to a wall for easy access. The box may also have a light that can visually communicate information to users including, for example, whether an item is missing, an item is expired, or whether an unauthorized user has accessed the device.

In an alternative embodiment, the RFID box may comprise a housing with dual doors that limit access to an interior cavity. The outer door may be connected to the front side of the housing via a hinge mechanism that allows it to move between and open position and a closed position. An inner door may be located behind the outer door in a recess in the front side of the housing. The inner door may also be connected to the housing via a hinge mechanism that allows it to move between an open position and a closed position. The inner door may be prevented from being opened until the outer door is opened. Both doors may have lips on them or other features to aid in manually opening and closing the doors, and both doors may be spring biased in an open position. Both doors may have electromechanical locking mechanisms that keep the doors securely closed by latches that inserts into apertures in the housing when the doors are closed. While opening of the doors may be achieved electronically when authorized permission is granted by an internal processor in communication with an access reader unit, the locking mechanisms may include mechanical override locks that allow the doors to be unlocked and locked in the event that the RFID box has no power. The internal processor may instruct an internal antenna in communication with an internal RFID reader to scan the contents of the interior cavity to read RFID tags when one or both of the doors are closed. In order for the RFID box to allow access when in receipt of electrical power, the access reader unit will read a first RFID card associated with an authorized user to open the outer door, and then read a second RFID card presented by a second authorized user in order to open the outer door. This dual authorization process may achieve desired security concerns for storing and accessing narcotics and other sensitive items.

This alternative embodiment may also comprise a drop box mechanism located on the top side of the RFID box, the drop box mechanism may allow items to be deposited into the interior cavity even when the inner door is closed, as long as the outer door has been opened. The drop box mechanism includes a mechanical internal locking feature comprising a spring pin, a lever and a slot on the drawer that secures the drawer in a closed position when the outer door is in a closed position. The drawer may also comprise an electrically actuated lock in addition to, or in lieu of, the mechanical internal locking feature.

The double door RFID box may be in electronic communication with a remote server associated with a database. The remote server may grant or deny requests for authorization, maintain audit records related to past access to the RFID box and which items were removed or added in connection with authorized users, may maintain an overall inventory of items stored in the RFID box and push alerts and notifications to users regarding access, attempts to access, and inventory. RFID information relayed to the remote server from the RFID box supports the tracking of items, access requests, and authorizations. The remote server may also support an online portal that users can access on a variety of devices in order to update permissions, search for particular items (such as those that may be subject to a recall or are expired), manage expiration date information, and perform other maintenance on the system. The remote server may communicate with and serve multiple RFID devices, with the ability to monitor overall inventory and track the movement of items from one RFID device to another.

The RFID tags may comprise a thin tail section for attachment to the objects to be inventoried and a pair of tabs separated from one another by a perforation. The tabs may include an RFID antenna and indication markers such as serial number, bar codes, and QR codes. Furthermore, the tabs may be configured to be folded against one another such that they create a flag. Alternatively, the second tab, which has the RFID antenna, may be torn from the first tab and adhered directly to the object to be inventoried.

An object of the present invention is to provide an RFID bulk scanning device that can be manufactured with relatively minimal labor effort and cost.

It is a further object of this invention to provide an RFID bulk scanning device that can scan objects to be inventoried located therein with a high degree of accuracy.

It is a further object of this invention to provide an RFID bulk scanning device that prevents electromagnetic leakage and interference.

It is a further object of this invention to provide an RFID bulk scanning system that can compare the current contents of the RFID bulk scanning device with a baseline data to determine, among other things, whether an item is missing or expired.

It is a further object of this invention to provide an RFID tag that can work efficiently with said RFID bulk scanning device and system.

It is a further object of this invention to provide an RFID scanning device that is compact and has wide utility.

It is a further object of this invention to provide RFID scanning devices of the type generally described herein, being adapted for the purposes set forth herein, and overcoming disadvantages found in the prior art. These and other advantages are provided by the invention described and shown in more detail below.

BRIEF DESCRIPTION OF THE DRAWINGS

Novel features and advantages of the present invention, in addition to those mentioned above, will become apparent to those skilled in the art from a reading of the following detailed description in conjunction with the accompanying drawings wherein identical reference characters refer to identical parts and in which:

FIG. 7A is a side sectional view taken along section line A-A of FIG. 6 and indicating Detail A;

FIG. 7B is a detailed side sectional view of Detail A shown in FIG. 7A;

FIG. 16 is a perspective view of the RFID box of FIG. 11 with the inventory basket of FIG. 15 located therein;

DETAILED DESCRIPTION OF THE INVENTION

Figure 1:
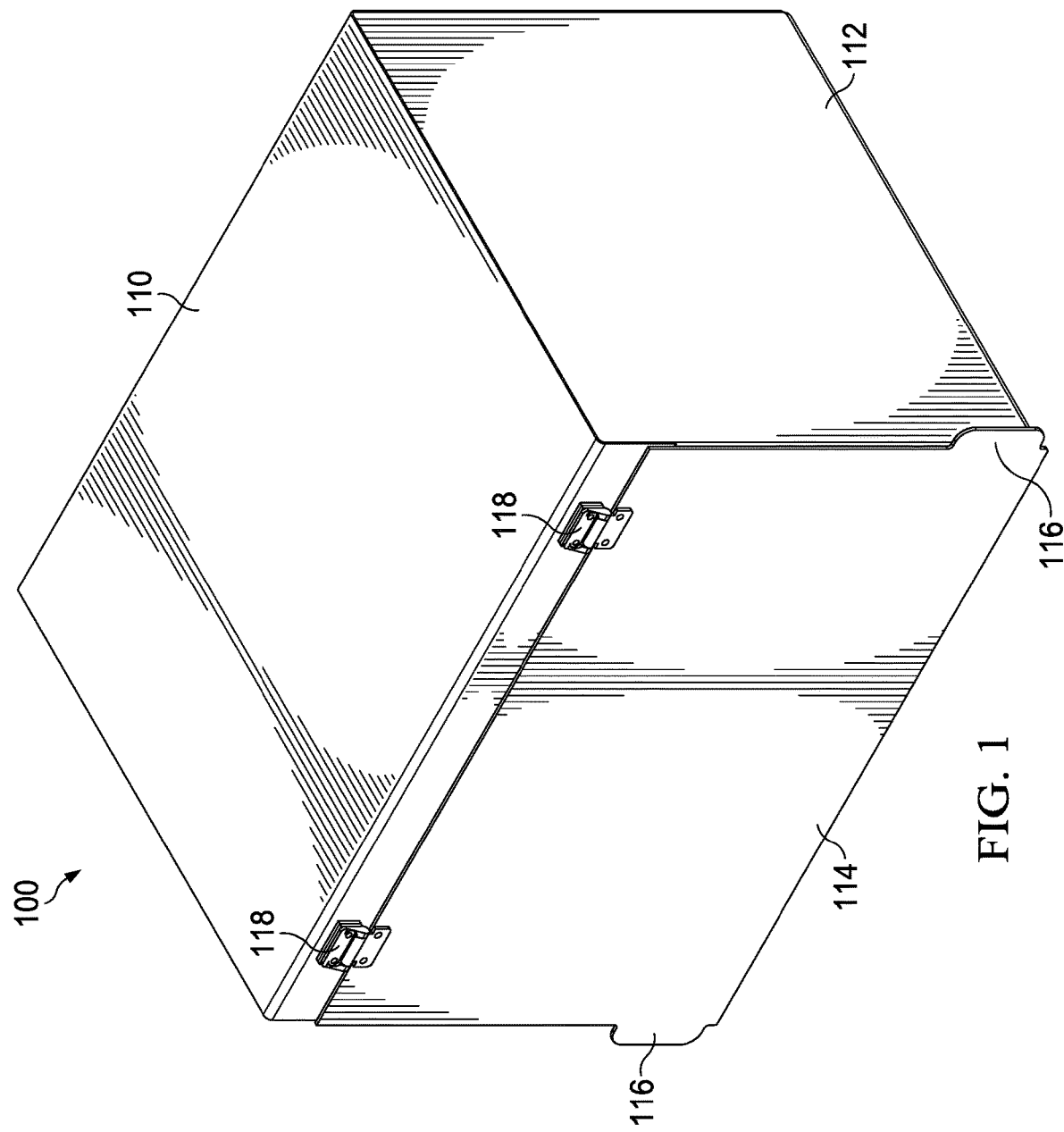
FIG. 1 is a perspective view of an exemplary embodiment of RFID box in accordance with the present invention.

FIG. 1 though FIG. 7B illustrate an exemplary embodiment of an RFID box 100 in accordance with the present invention. In exemplary embodiments of the present invention, the RFID box 100 is rectangular in shape and comprises a housing. The housing may comprise a door 114, an enclosure 110, and a pair of side panels 112. This is merely exemplary, as any size and shape RFID box 100 is contemplated along with any number of components constituting the housing of said RFID box 100.

The enclosure 110 may be C-shaped such that it forms the top, rear, and bottom surfaces of the housing and surrounds an interior cavity 113 that is accessible through the door 114. The enclosure 110 may additionally include a lip that extends vertically from the top and the bottom surfaces such that it forms a portion of the front surface of the housing and partially defines an aperture in the front surface of the housing. The pair of side panels 112 may be configured to fit within the enclosure 110 on either side thereof such that the side panels 112 forms the side surfaces of the RFID box 100. In exemplary embodiments of the present invention, the side panels 112 may be open top box shaped such that they likewise create a lip that protrudes inwardly from the left and right side panels such that it forms a portion of the front surface of the housing and partially defines an aperture in the front surface of the housing.

One or more hinges 118 may connect the door 114 to the housing such that the RFID box 100 is completely enclosed. In exemplary embodiments of the present invention, a pair of hinges 118 are located on the lip formed along the upper edge of the enclosure 110 and connect the door 114 to the enclosure 110. This may reduce sagging of the door 114 otherwise resulting from placing the hinges on the side of the RFID box 100. Sagging of the door 114 may create gaps in the RFID box 100 housing and result in electromagnetic leakage.

In exemplary embodiments of the present invention, the hinges 118 are continuous tension hinges that are configured to bias the door 114 in the opened position, preferably at a 170° angle from the front surface of the RFID box 100. The door 114 may be sized and located to cover the front of the RFID box 100 and be substantially flush with the side and bottom edges thereof, thereby preferably overlapping with at least a portion of the lip created by the enclosure 110 and the side panels 112. In exemplary embodiments of the present invention, the door 114 may comprise one or more tabs 116 that protrude beyond the side panels 112 to facilitate a user manipulating the door 114 between a closed position and an opened position. In other exemplary embodiments of the present invention, the door 114 may comprise pull handles, knobs, or other devices for opening and closing the door 114.

Figure 2:
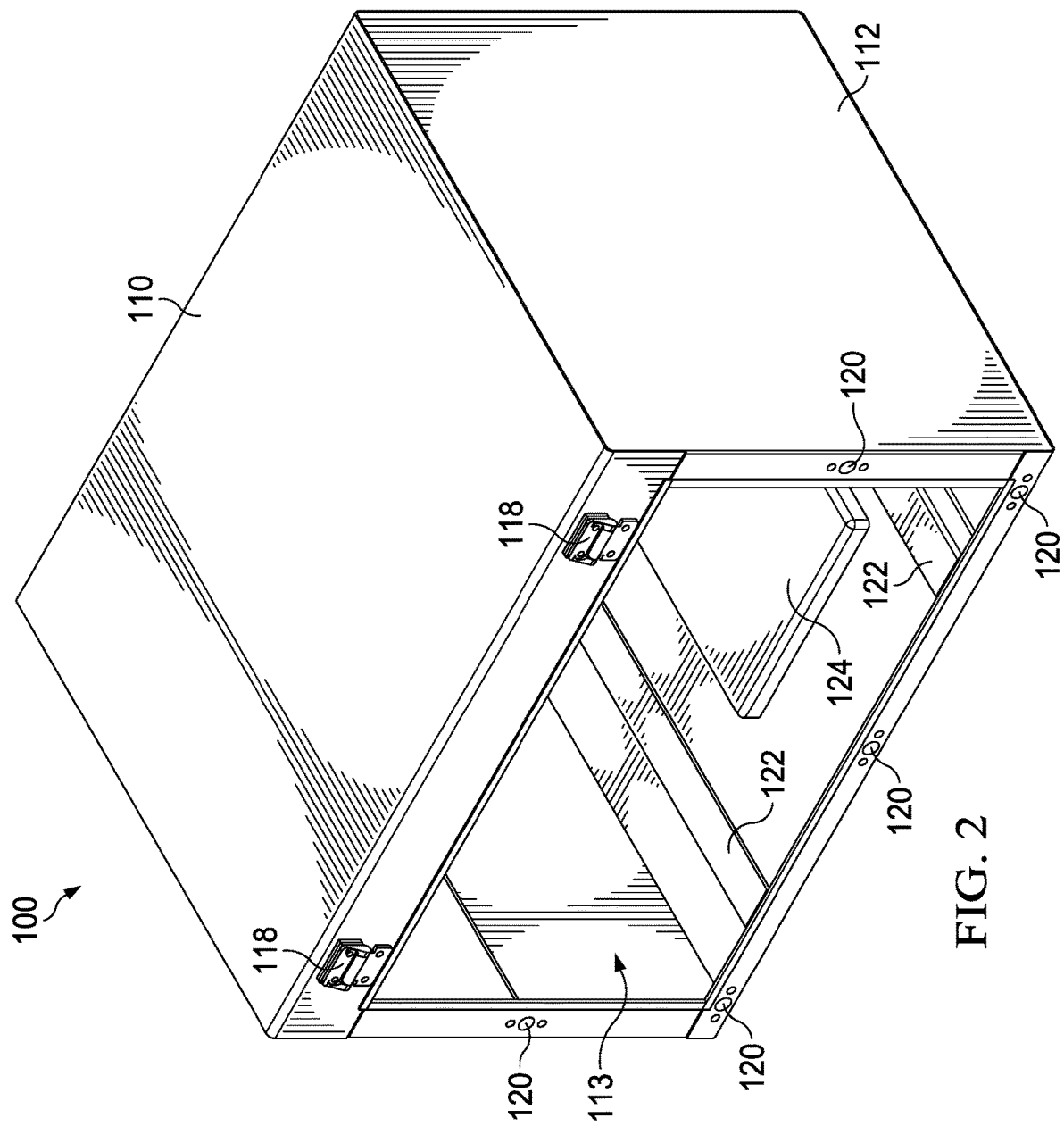
FIG. 2 is a perspective view of the device of the RFID box of FIG. 1 illustrated with the door removed to show in the interior of the RFID box.
Figure 3:
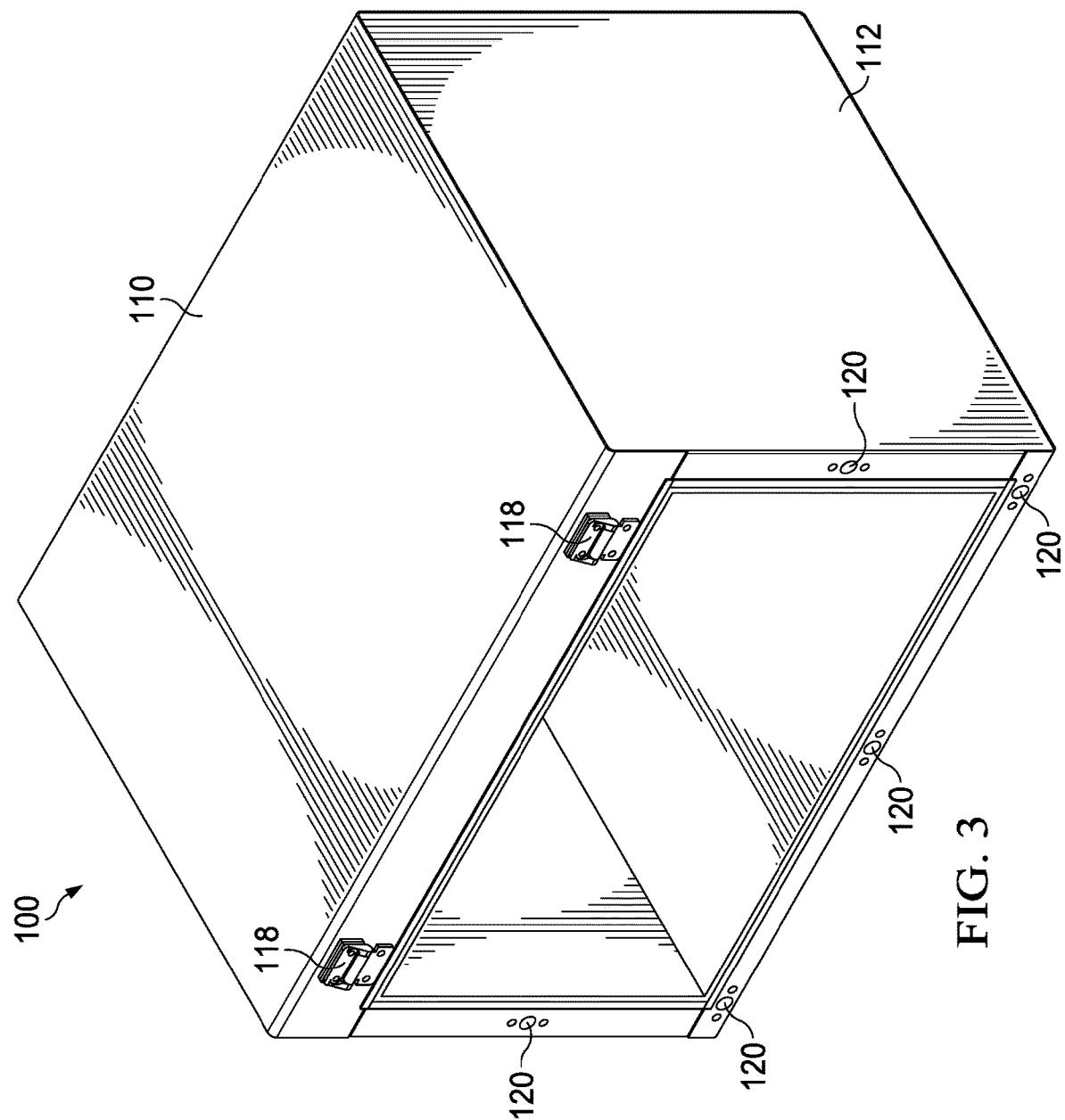
FIG. 3 is a perspective view similar to FIG. 2 shown with some of the interior elements removed to further illustrate the interior of the RFID box.
Figure 4:
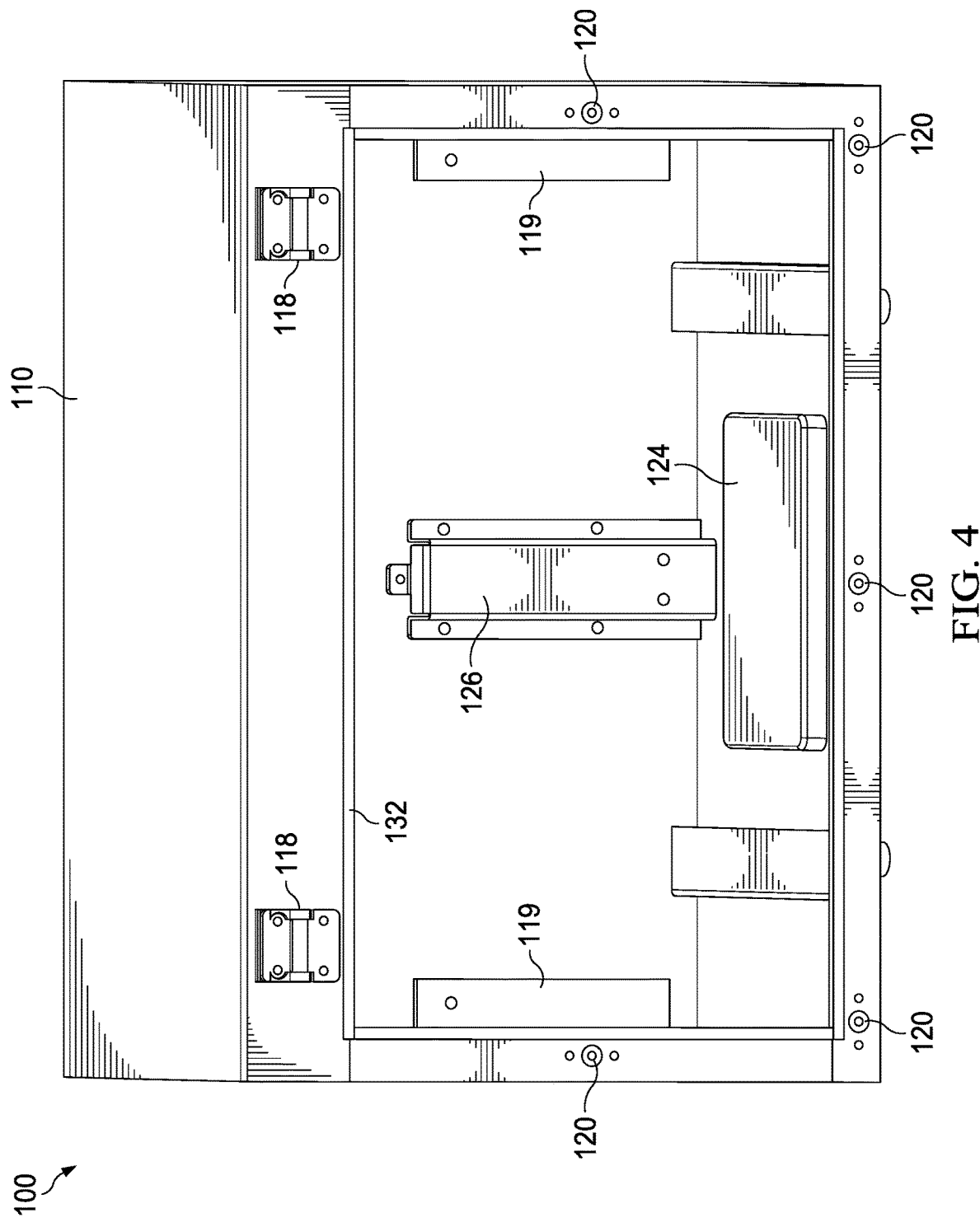
FIG. 4 is a front perspective view of the RFID box of FIG. 1 illustrated with the door removed to show the interior of the RFID box.
Figure 5:
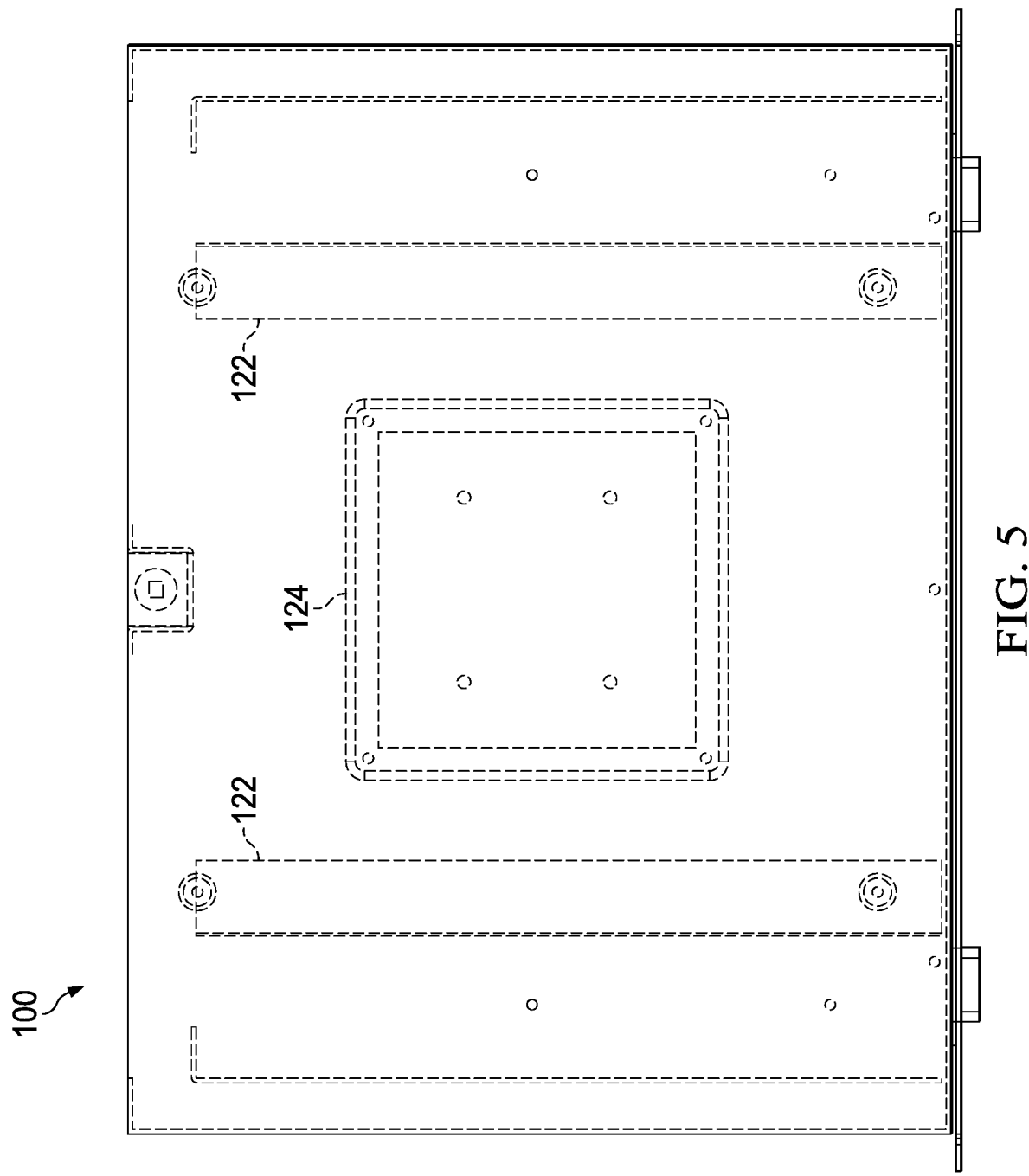
FIG. 5 is a bottom view of the RFID box of FIG. 1.
Figure 6:
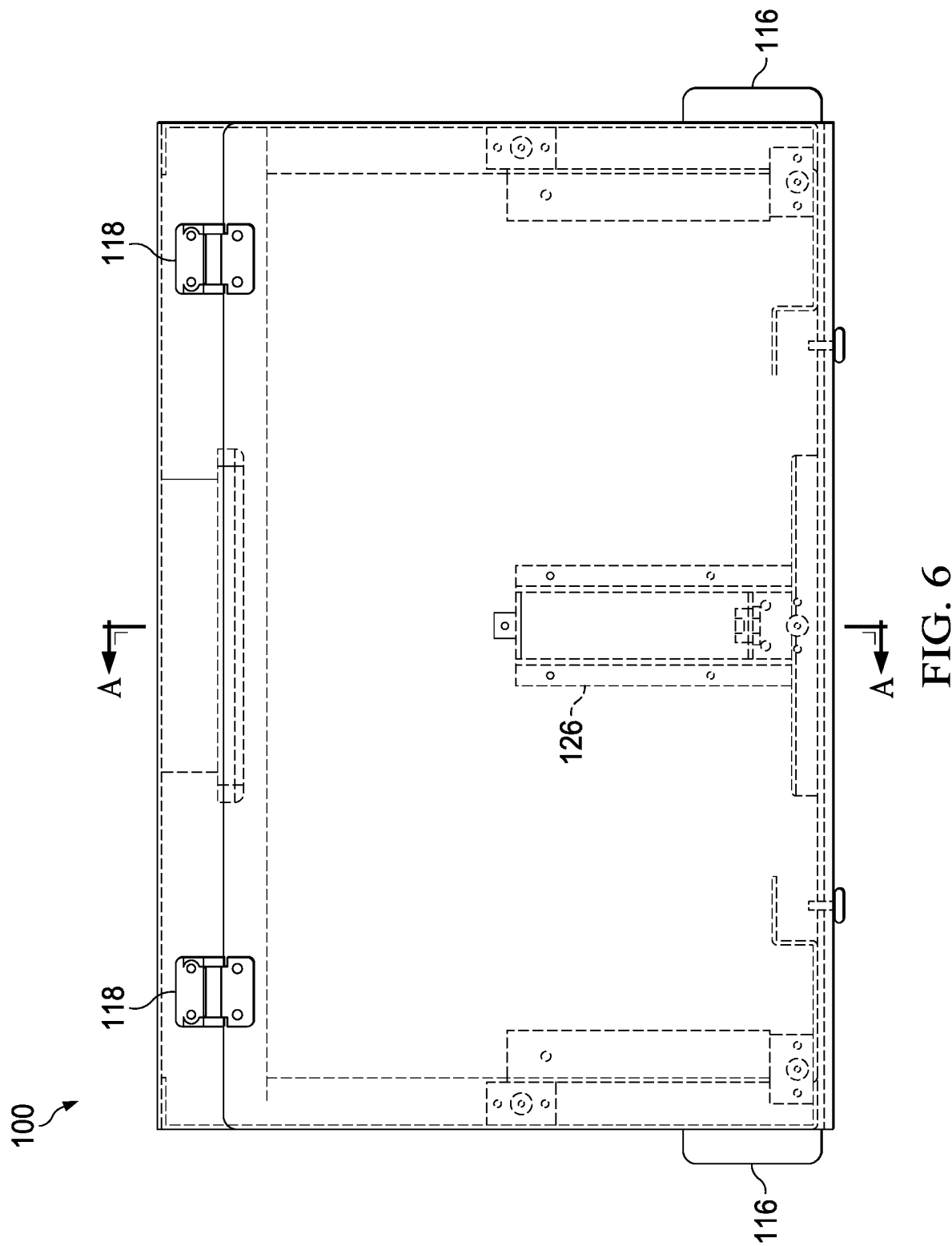
FIG. 6 is a rear view of the RFID box of FIG. 1 indicating section line A-A.

As best shown in FIG. 2 through FIG. 4, the lip extending around the front of the RFID box 100 may further comprise a number of latches 120. These latches 120 may be configured to temporarily secure the door 114 in the closed position against the housing. The latches 120 may be magnetic devices configured to interact with the door 114 itself or magnets located thereon such that the door 114 is held securely in place against the housing until acted upon by a user.

FIG. 2 through FIG. 4 also illustrates the interior of the RFID box 100. A pair of guide rails 122 may be used to guide an inventory basket 238 (best shown in FIGS. 15-16), tray, or other container for various objects to be inventoried. Any number, size, shape, or location of guide rails 122 are contemplated. In exemplary embodiments of the present invention, the guide rails 122 are configured to mate with the inventory basket 238 or other container and keep it centered as it is placed within the RFID box 100.

Figure 17A:
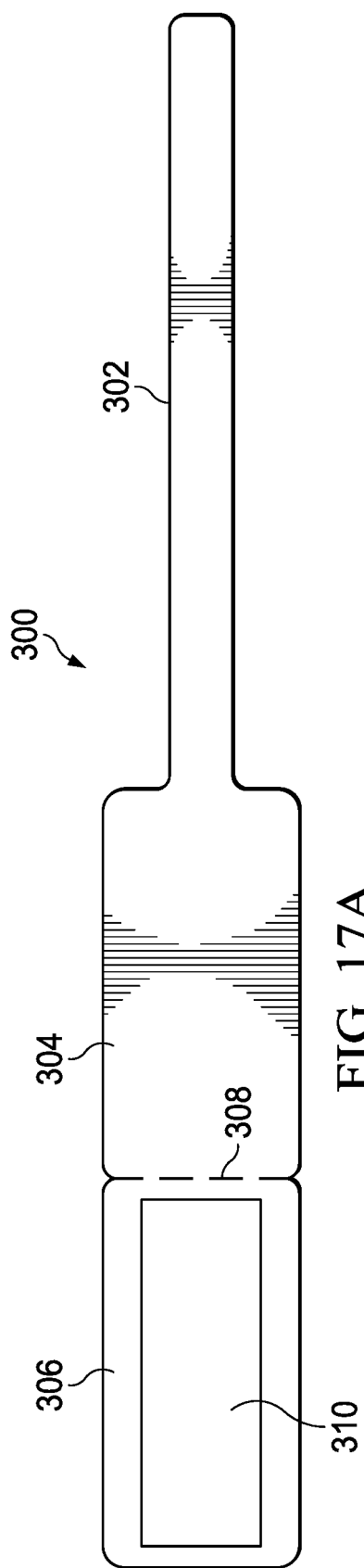
FIG. 17A is a rear view of an exemplary RFID tag for use with the present invention.
Figure 17B:
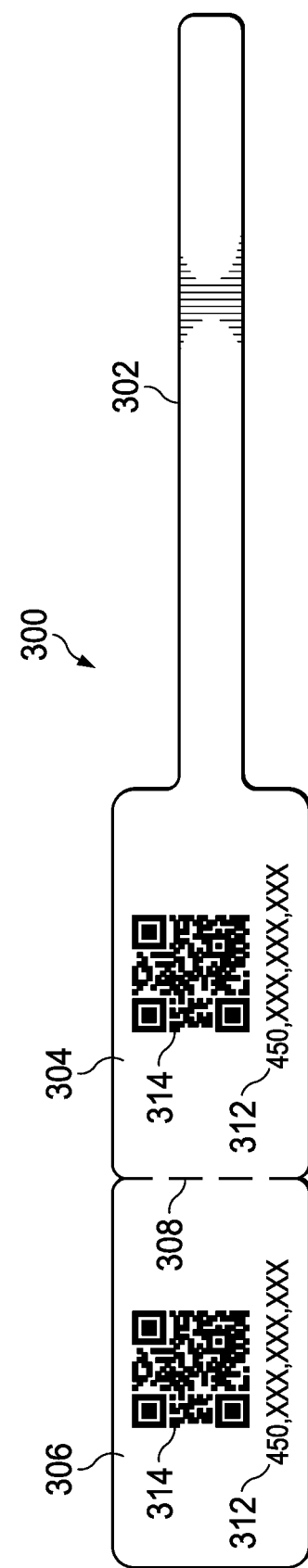
FIG. 17B is a front view of the RFID tag of FIG. 17A.
Figure 18:
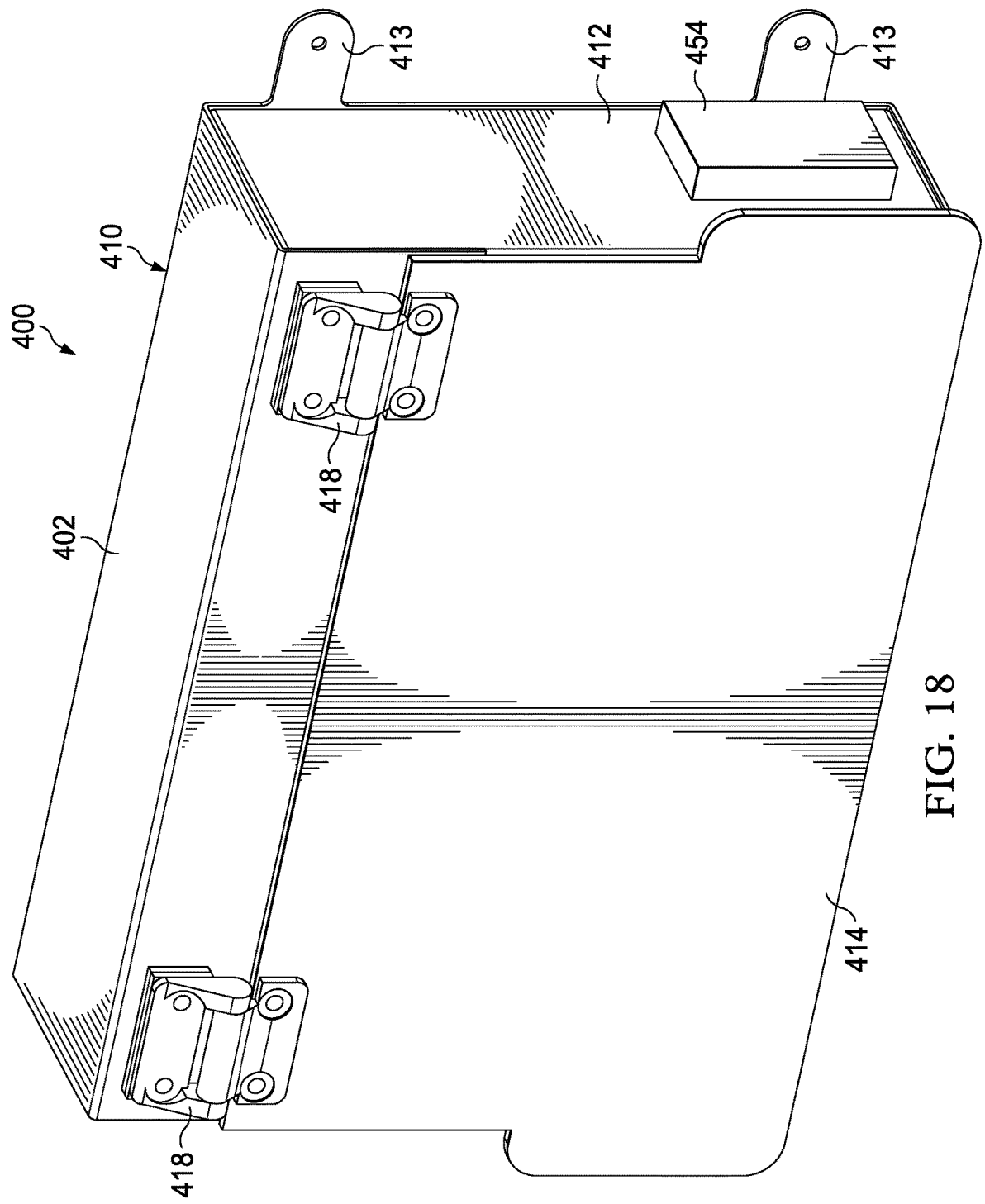
FIG. 18 is a perspective view of an exemplary RFID distribution box.
Figure 19:
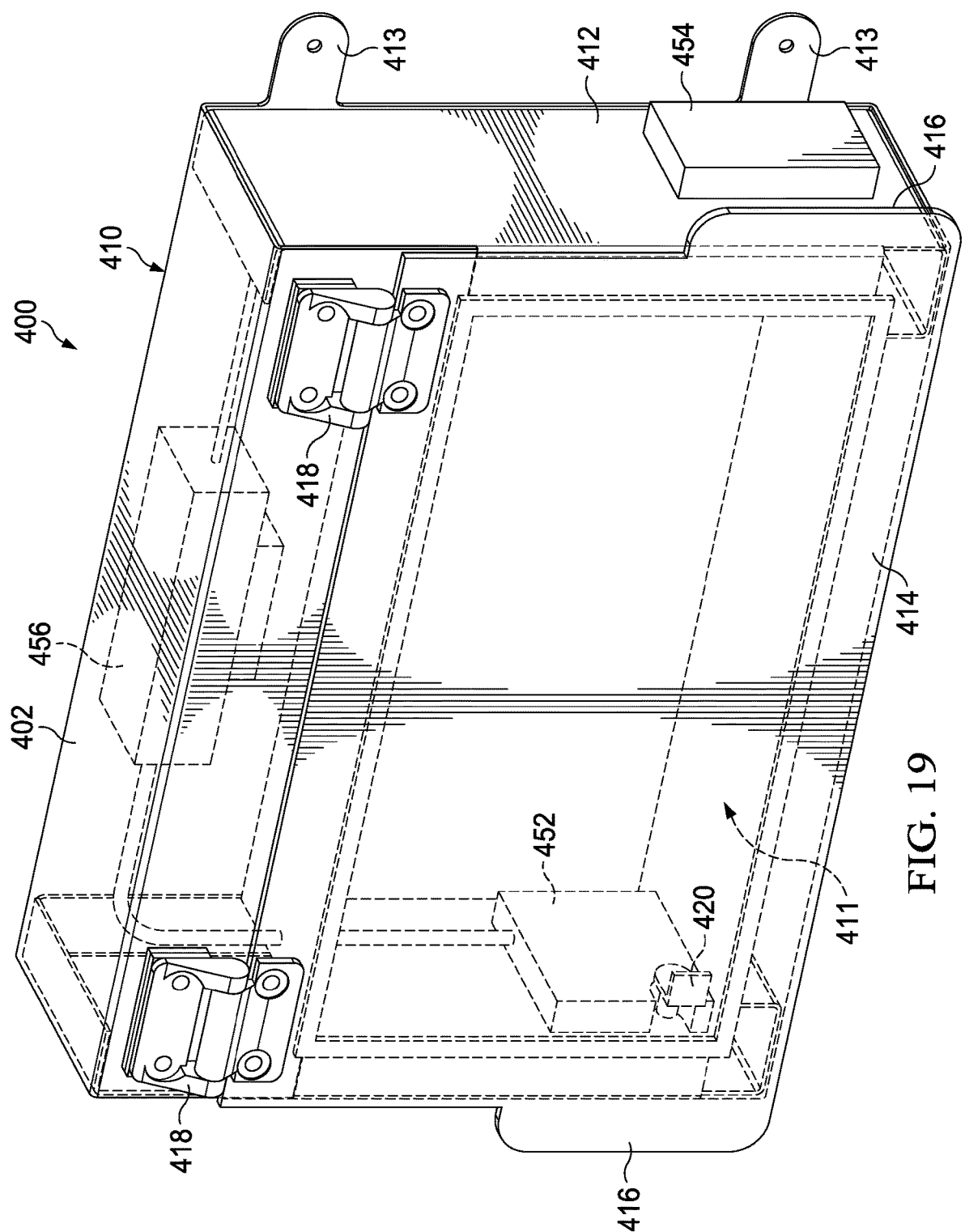
FIG. 19 is a perspective partially transparent view of the device of FIG. 18.

A gasket 132 may be located along the perimeter of the front surface of the housing for the RFID box 100. In exemplary embodiments, the gasket 132 may extend along the lip created by the enclosure 110 and the side panels 112. The gasket may be comprised of a conductive material and may be a foam, tape, pad, or the like. An RFID antenna 124 may be located along the bottom surface of the RFID box 100. The RFID antenna 124 may be configured to communicate with a series of RFID tags 300 (as shown in FIGS. 17A-C, for example). Preferably, the guide rails 122 are configured to keep the inventory basket 238 or other container above the RFID antenna 124 and thus prevent inadvertent contact or damage.

As best illustrated in FIG. 7A, an RFID antenna/reader 128 may be located along the top of the RFID box 100. The location of the RFID antenna 124 and RFID antenna/reader 128 are merely exemplary, any location is contemplated. Further, any number of RFID antennas 124 and RFID antenna/reader 128 are contemplated. The RFID antenna 124 and the RFID antenna/reader 128 may be electrically connected, preferably by a wire 130. The wire 130 may comprise wire for supplying power to components of the RFID box 100, including, but not limited to, the RFID antenna 124 and the RFID antenna/reader 128, as well as wire for facilitating the communication of data to and from components of the RFID box 100, including but not limited to the RFID antenna 124 and the RFID antenna/reader 128. In order to minimize electromagnetic leakage, the wire 130 may exit the RFID box 100 thorough a pass through device 126.

In exemplary embodiments of the present invention, the pass through device 126 may be configured to cover the aperture in the RFID box 100 where the wire 130 passes outside of the RFID box 100. The pass-through device 126 may comprise an enclosure defining a channel which extends along the rear wall of the RFID box 100 for the wire 130 to pass through. The pass through device 126 may be fastened, welded, or otherwise adhered to the inside rear wall of the RFID box 100. Preferably, conductive tape is used along the seams between the pass through device 126 and the RFID box 100 to minimize electromagnetic leakage. The pass through device 126 may comprise a coupler 134 (as best illustrated in FIG. 7B) that connects the internal wire 130 to an external wire 131. The coupler 134 may be configured to substantially seal the aperture otherwise required to allow the wire 130 to pass outside of the RFID box 100. In exemplary embodiments of the present invention, the coupler 134 may be a female to female Ethernet and power connector.

One or more mechanical stops 119 may be located along the rear wall of the RFID box 100, though such is not required. The mechanical stops 119 may be configured to prevent the inventory basket 238 or other container from contacting the pass through device 126 and/or the rear wall of the RFID box. In other exemplary embodiments of the present invention, the pass through device 126 may act as a mechanical stop 119.

The components of the RFID box 100, including, but not limited to, the enclosure 110, the side panels 112, and the pass-through device 126 may be fastened, welded, adhered, or otherwise secured in their respective locations preferably by conductive materials. Conductive tape or other conductive material may be additionally placed along the seams of the components of the RFID box 100 so as to minimize RFID leakage. These components may be comprised of a metallic, conductive material such as, but not limited to, aluminum. Specifically, they may be comprised of ⅛" thick aluminum, though any thickness is contemplated. The use of a conductive material may serve to substantially electromagnetically "seal" the RFID box 100, thus minimizing RFID leakage, which thereby ensures accuracy in RFID readings by ensuring that the RFID antenna 124 and RFID antenna/reader 128 only detect RFID signals being emitted from within the RFID box 100.

Figure 8:
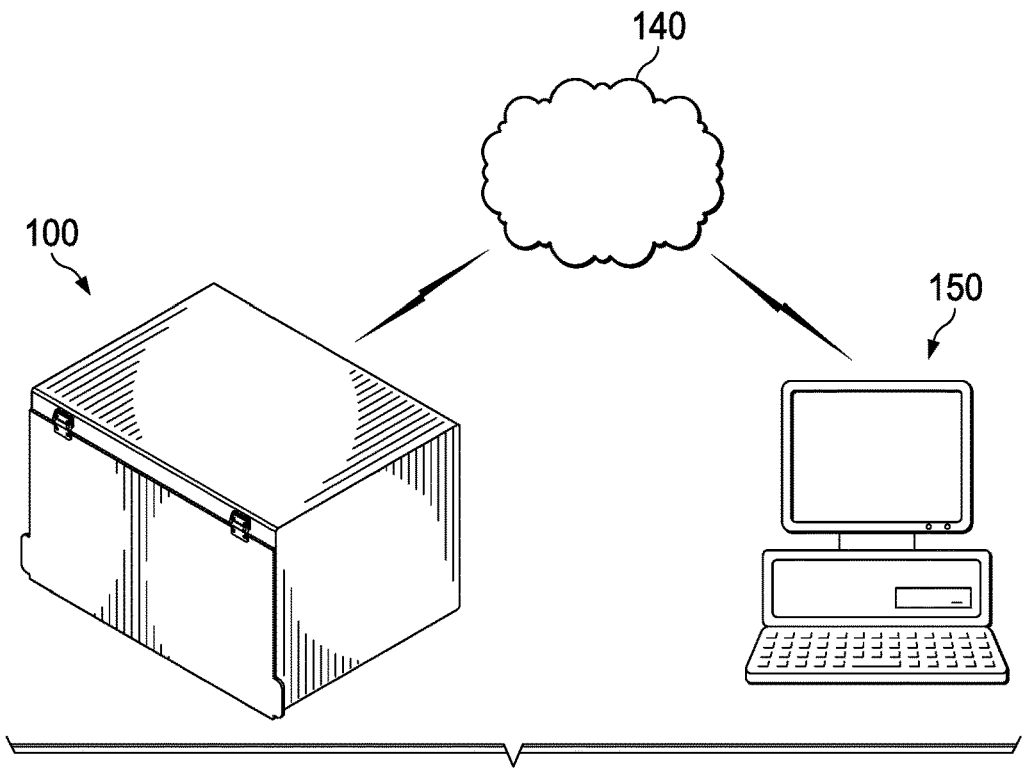
FIG. 8 is a plan view of an exemplary system in accordance with the present invention.

FIG. 8 is a plan view of an exemplary system in accordance with this invention. The system may comprise the RFID box 100, a server 140, and an electronic device 150. The RFID box 100 may be electrically connected to the server 140, which may be electrically connected to the electronic device 150. The electrical connection may be wired or wireless. In exemplary embodiments of the present invention, the server 140 is located remote from the RFID box 100 and the electronic device 150. For example, without limitation, the server 140 may be a cloud based data storage and processing server. Likewise, the electronic device 150 may be located remote from the server 140 and the RFID box 100. The RFID box 100, server 140, and electronic device 150 may be connected via the world wide web, the internet, intranet, or other communications network. The electronic device 150 may be a laptop, personal computer, tablet, smart phone, or the like.

Figure 9:
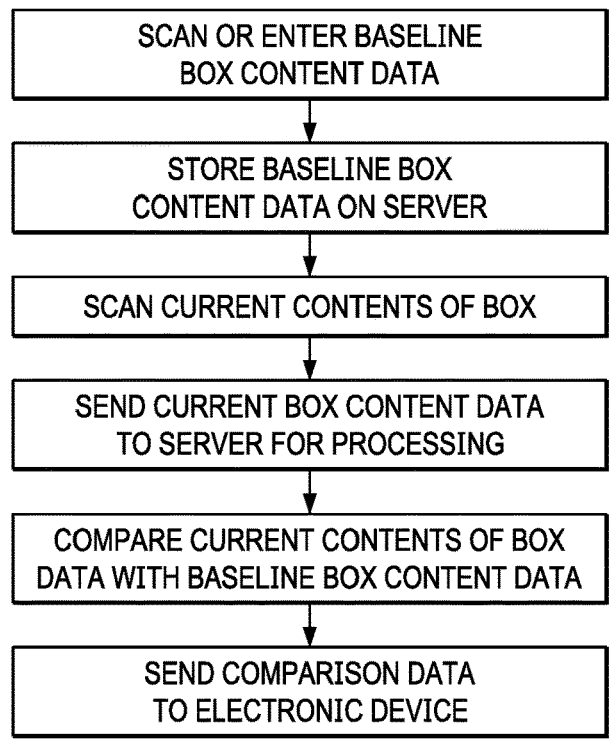
FIG. 9 is a flow chart of exemplary logic for use with the system of FIG. 8 and in accordance with the present invention.
Figure 10:
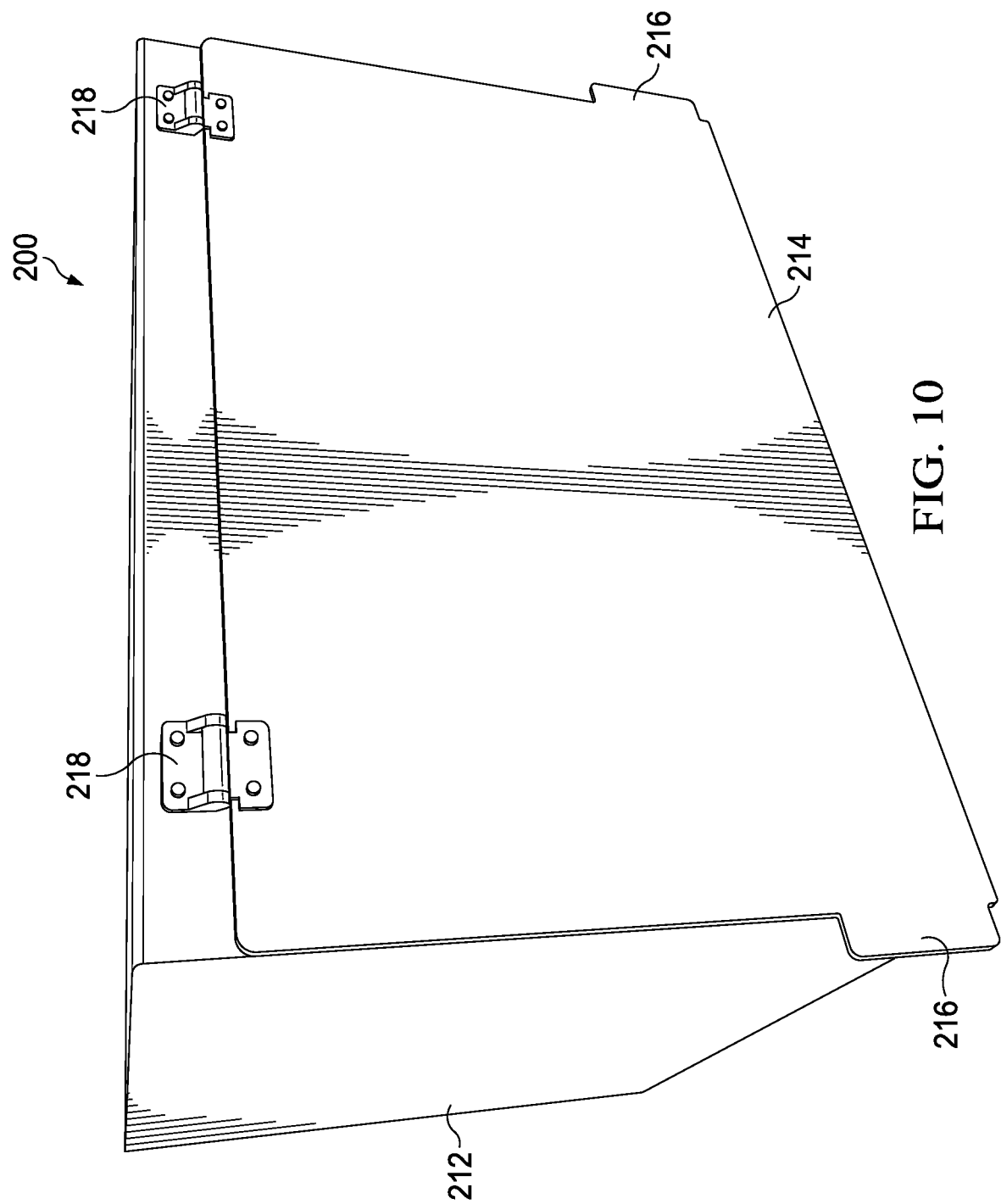
FIG. 10 is a front perspective view of another exemplary embodiment of the RFID box of the present invention.

FIG. 9 is a flow chart of exemplary logic for use with the system of FIG. 8. Initially, the RFID box 100 may perform a scan of the inventory located therein. This may be accomplished by known methods. The data pertaining to contents of the RFID box 100 and related information are hereinafter referred to as the baseline box content data. In other exemplary embodiments of the present invention, the baseline box content data may be generated in whole or part by manual entry. This baseline box content data may include the contents of the RFID box 100, names for the contents, serial numbers, and the like. For example, but without limitation, the RFID box 100 may be used in a medical setting for the inventory of medications. In such a case, the baseline box content data may include the number, type, name, expiration date, prescribing physician, date stored, date removed, and the like for each medication in the RFID box 100. Of course, this application is merely exemplary and is not intended to be limiting. Any application for the RFID box 100 is contemplated.

The baseline box content data may be transmitted to and stored on the server 140. At a later time, the contents of the RFID box 100 may be scanned and the data recorded, this data is hereinafter referred to as the current box content data. The current box content data may then be transmitted to the server 140 for storage and processing. The server 140 may compare the current box content data with the baseline box content data and produce summary of the comparison, hereinafter referred to as the comparison data. The comparison data may then be transmitted to the electronic device 150 for display.

Figure 11:
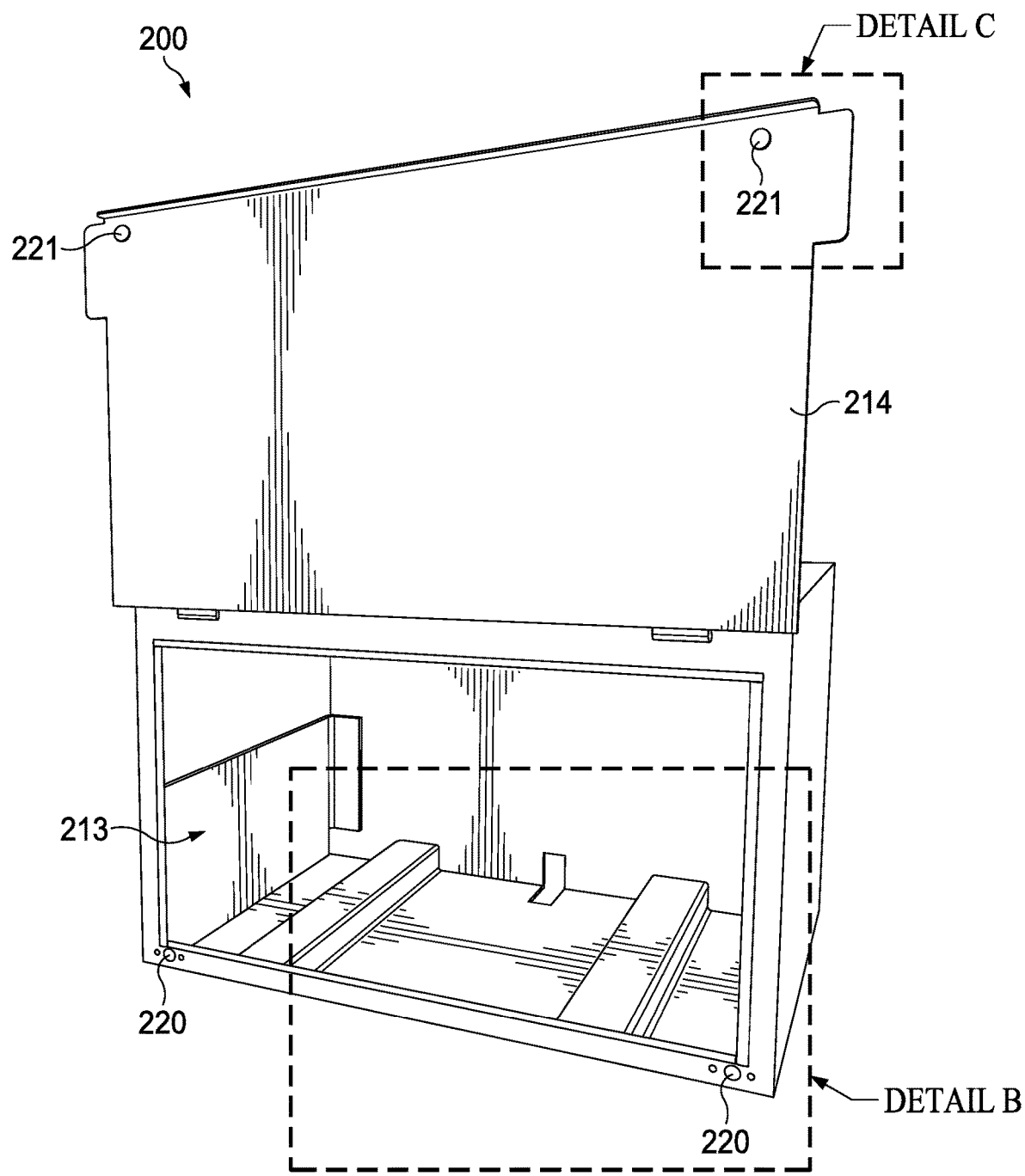
FIG. 11 is a front perspective view of the device of FIG. 10 shown with the door in an opened position and indicating Detail B and Detail C.
Figure 12:
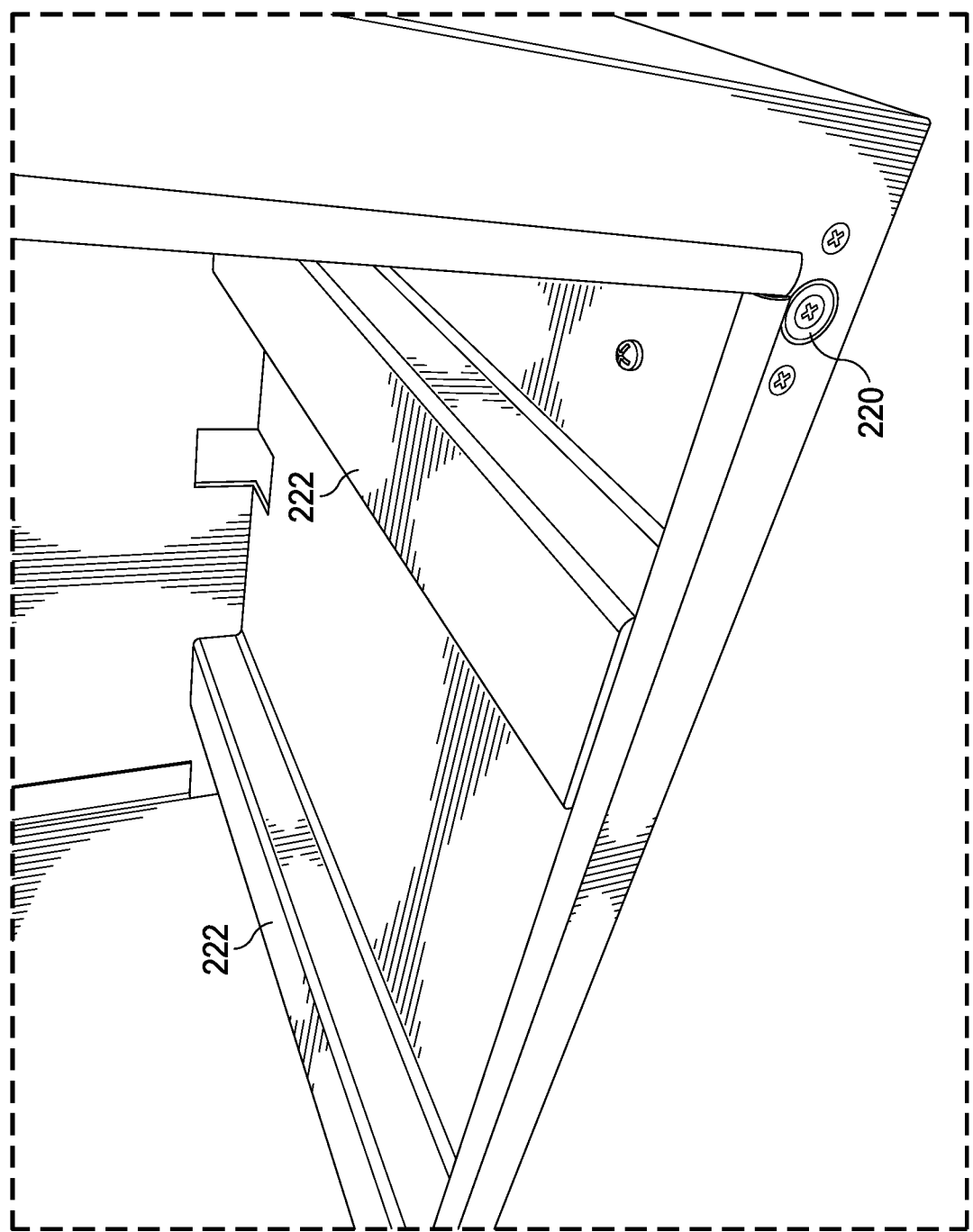
FIG. 12 is a detailed front perspective view of Detail B shown in FIG. 11.
Figure 13:
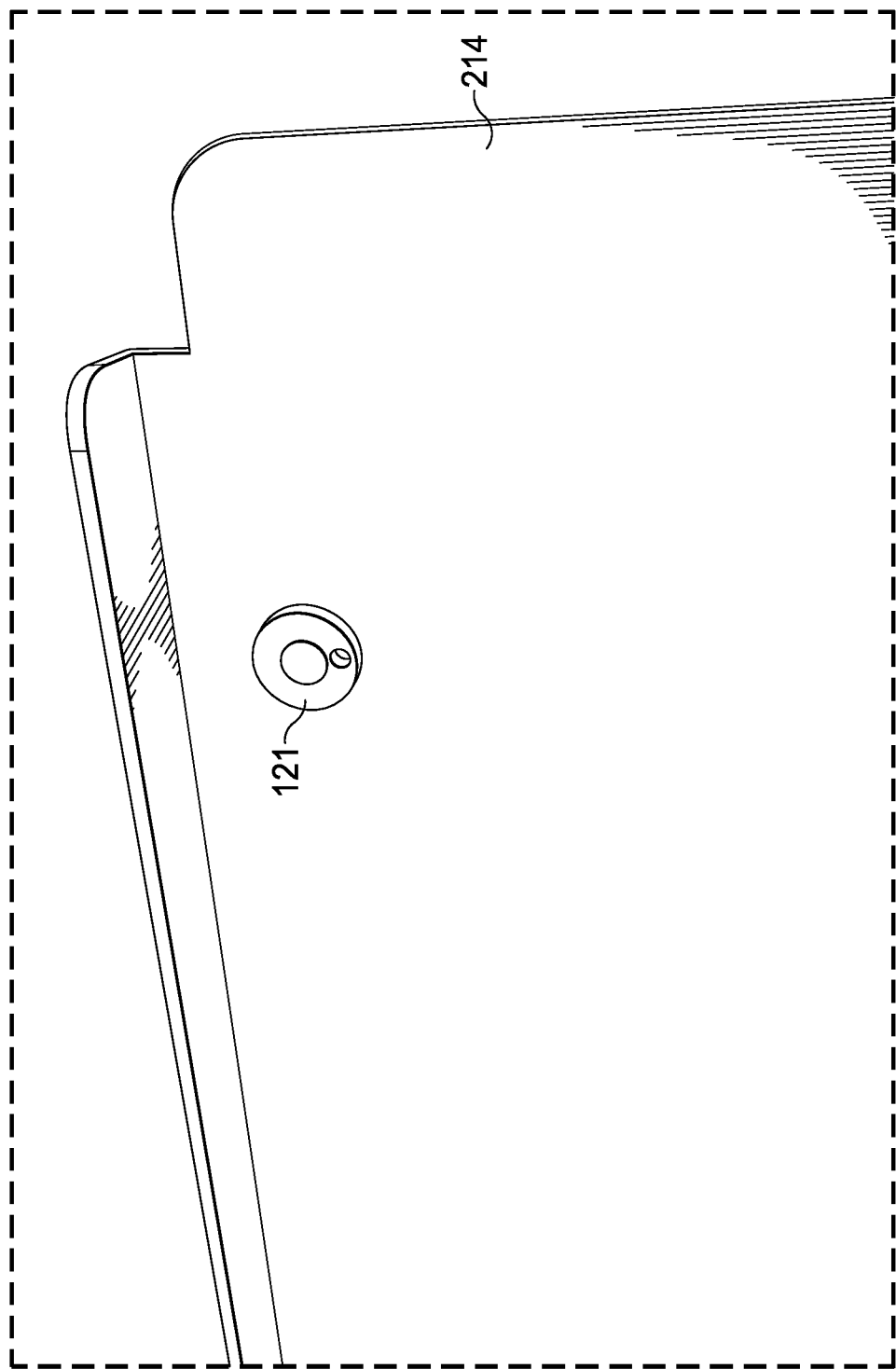
FIG. 13 is a detailed front perspective view of Detail C shown in FIG. 11.

FIG. 10 through FIG. 16 illustrates another exemplary embodiment of the present invention. In these figures, like elements have been labeled similarly to the first embodiment (e.g., RFID box 200, interior enclosure 213, door 214, tabs 216, guide rails 222, etc.). FIG. 11 through FIG. 13 illustrate how the latches 220 may interact. For example, the latches 220 may be magnetic devices placed on the lip of the RFID box 200 and may be configured to interact with a series of magnets 221 placed on the door 214. The magnets may be located and oriented such that they are attracted to one another and hold the door 214 shut when the door 214 is located in a closed position.

Figure 14:
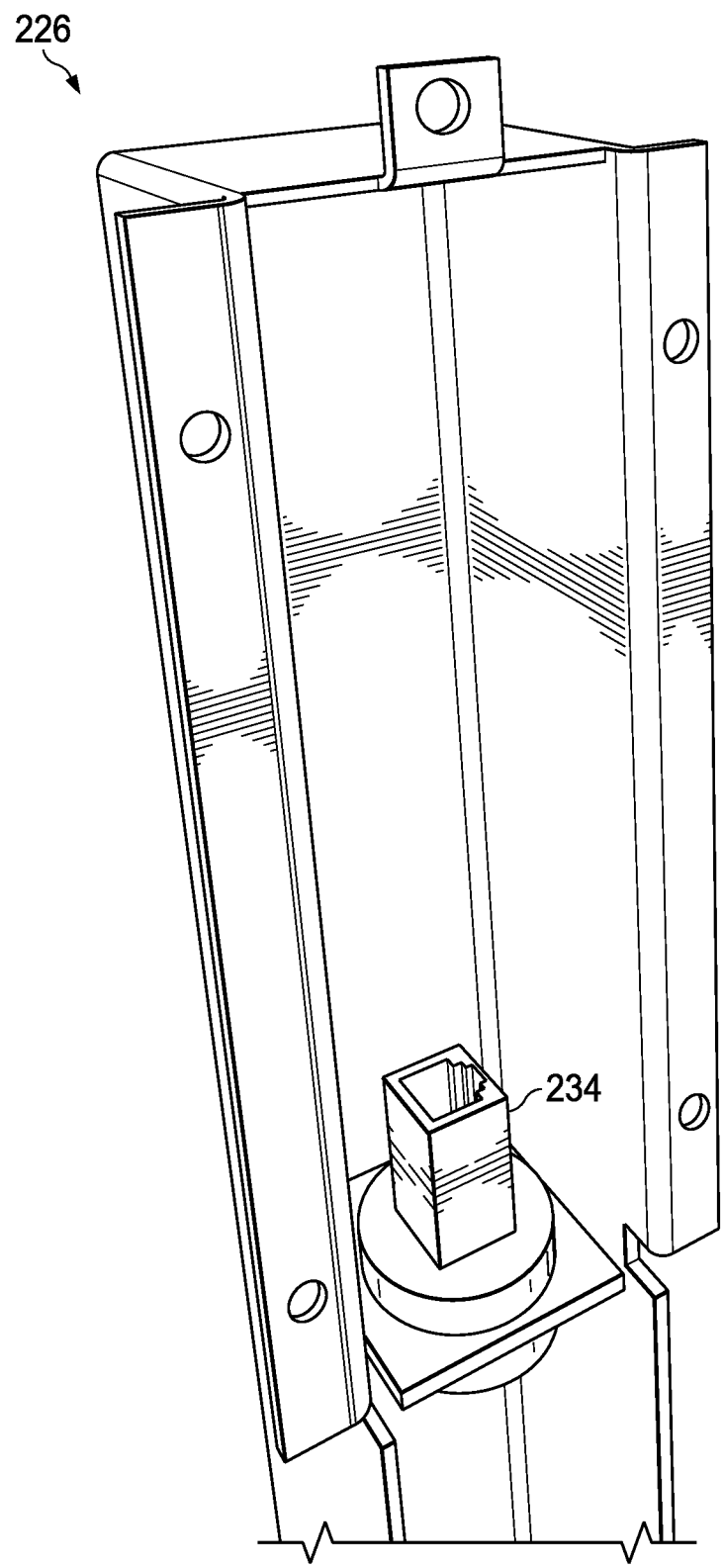
FIG. 14 is a detailed front perspective view of an exemplary pass through device used with the RFID box of FIG. 10.

FIG. 14 illustrates the rear view of and interior of another exemplary pass through device 226. In the present embodiment, the pass-through device 226 may be substantially rectangular in shape and contain the coupler 234 positioned on a bottom portion thereof and extended between a plate that substantially fills the interior of the pass-through device 226.

Figure 15:
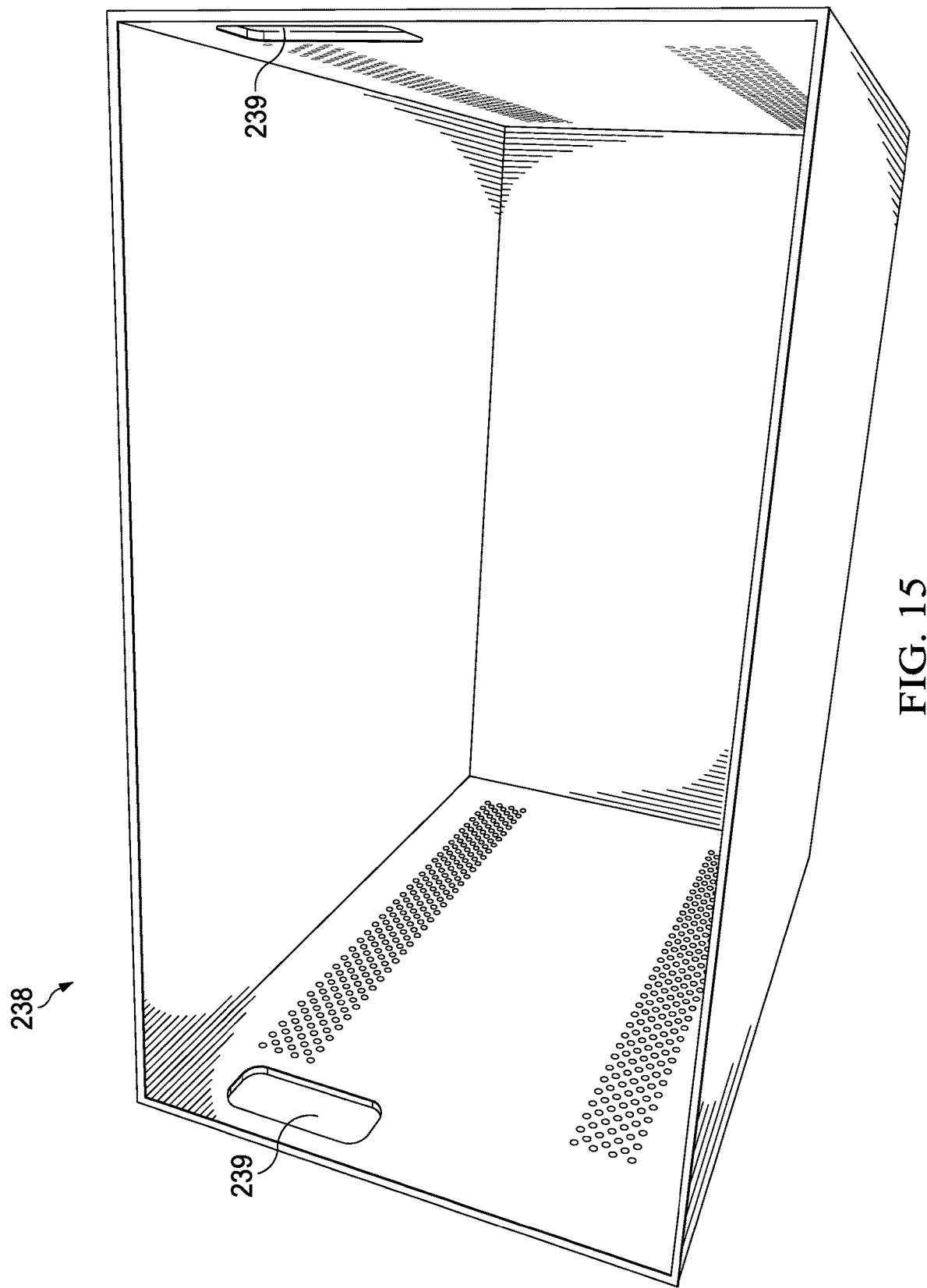
FIG. 15 is a perspective view of an inventory basket used with the RFID box of FIG. 10.

In exemplary embodiments of the present invention, as illustrated in FIGS. 15 and 16, the inventory basket 238 may be sized and configured to substantially fill the interior cavity of the RFID box 200. The inventory basket 238 may comprise grab handles 239 for ease of use.

FIGS. 17A and 17B illustrate an exemplary RFID tag 300 for use with the present invention. The RFID tag 300 may comprise a tail section 302 connected to a first tab 304, which is connected to a second tab 306. The first tab 304 and the second tab 306 may be separated by a perforation 308. Some or all of the rear surface of the RFID tag 300 may comprise an adhesive such that the RFID tag 300 may be placed on an object to be inventoried, such as, but not limited to, a medication container. The tail section 302 may be sized and configured to wrap around an object to be inventoried such that the first tab 304 sticks out from the object to be inventoried. Preferably, the tail section 302 has a reduced thickness relative to the first and second tabs 304 and 306 such that the object to be inventoried can be clearly seen. For example, without limitation, if placed around a medicine container, the label on the container and the drug itself can be clearly viewed. The second tab 306 may be removed, preferably along the perforation 308, and adhered to an object to be inventoried. In other exemplary embodiments, the second tab 306 may be folded onto the first tab 304 along the perforation 308 to form a flag.

The first tab 304 and the second tab 306 may each comprise an identification number 312 and/or a code 314 such as, but not limited to, a bar code, QR code, or the like. The second tab 306 may further comprise an RFID antenna 310 configured to communicate with the RFID antennas 124 and the RFID antenna/reader 128.

In an exemplary embodiment, each tab 306, 304 has a length of approximately 1.189 inches and a height of 0.6 inches. The tail has a height of 0.188 inches. The RFID tag 300 has an overall length of 4.75 inches, prior to any folding. The RFID tag has a thickness of 0.005 inches. In other embodiments, the dimensions of the RFID tag may vary as desired. Any size, shape, or design of the RFID tag 300 is contemplated.

A further exemplary embodiment of the invention that includes access control and auditing features is depicted in connection with FIGS. 18-25. In applications in which the present invention is deployed in connection with control substance inventories and other similarly controlled and dangerous items, it may be desirable for access to such inventories to be monitored and controlled. In the case of pharmaceutical deployment, for instance, such as at a healthcare facility, drugs inventoried utilizing the RFID box discussed herein may be distributed about the facility for use and expedient access during the provision of healthcare services. For example, distribution boxes such as box 400 may be placed in convenient locations throughout a facility for access by healthcare professionals, patients and the like, as needed.

In some embodiments, the distribution boxes may be networked with an inventory system such as shown in connection with FIG. 8 above, and may log deposits and withdraws of an inventory kit or basket and the contents thereof at each event. In other embodiments, the distribution boxes may be configured to authenticate a user attempting to access the box before access is granted. In some of these embodiments, the distribution boxes may further or separately track box access for audit purposes or regulatory compliance, for example, such as for use in furthering Joint Commission (JCAHO) compliance goals.

An exemplary embodiment of the distribution box 400 is shown with Faraday cage construction shielding methods similar to those described in connection with the RFID box 100. An enclosure 410 may be C-shaped such that it forms the top 402, rear 404, and bottom 406 surfaces of the housing. The enclosure 410 may additionally include lips 408 and 409 that extend vertically from the top 402 and the bottom 406 surfaces such that it forms a portion of the front surface of the housing and partially defines an aperture 411 in the front surface of the housing. In some embodiments, it may be convenient to mount the invented distribution box 400 on a vertical surface, such as the wall of a hospital operating room or patient room, such that mounting brackets 413 are provided for securing said box 400 to said vertical surface. A pair of side panels 412 may be configured to fit within the enclosure 410 on either side thereof such that the side panels 412 forms the side surfaces of the distribution box 400. In exemplary embodiments of the present invention, the side panels 412 may be open top box shaped such that they likewise create a lip that protrudes inwardly from the left and right side panels such that it forms a portion of the front surface of the housing and partially defines an aperture 411 in the front surface of the housing.

One or more hinge mechanisms 418 may connect the door 414 to the housing such that the distribution box 400 is completely enclosed. In an exemplary embodiment of the present invention, one or more hinges 418 are located on the lip formed along the upper edge of the enclosure 410 and connect the door 414 to the enclosure 410. This may reduce sagging of the door 414 otherwise resulting from placing the hinges on the side of the distribution box 400. Sagging of the door 414 may create gaps in the distribution box 400 housing and result in electromagnetic leakage, which is undesirable in applications in which the inventory items in a kit are being logged.

In exemplary embodiments of the present invention, the hinges 418 are continuous tension hinges that are configured to bias the door 414 in the opened position, preferably at a 170° angle from the front surface of the distribution box 400. The door 414 may be sized and located to cover the front of the distribution box 400 and be substantially flush with the side and bottom edges thereof, thereby preferably overlapping with at least a portion of the front face of the box 400 created by the lips of the enclosure 410 and the side panels 412. In exemplary embodiments of the present invention, the door 414 may comprise one or more tabs 416 that protrude beyond the side panels 412 to facilitate a user manipulating the door 414 between a closed position and an opened position. In other exemplary embodiments of the present invention, the door 414 may comprise pull handles, knobs, or other devices for opening and closing the door 414.

Figure 20:
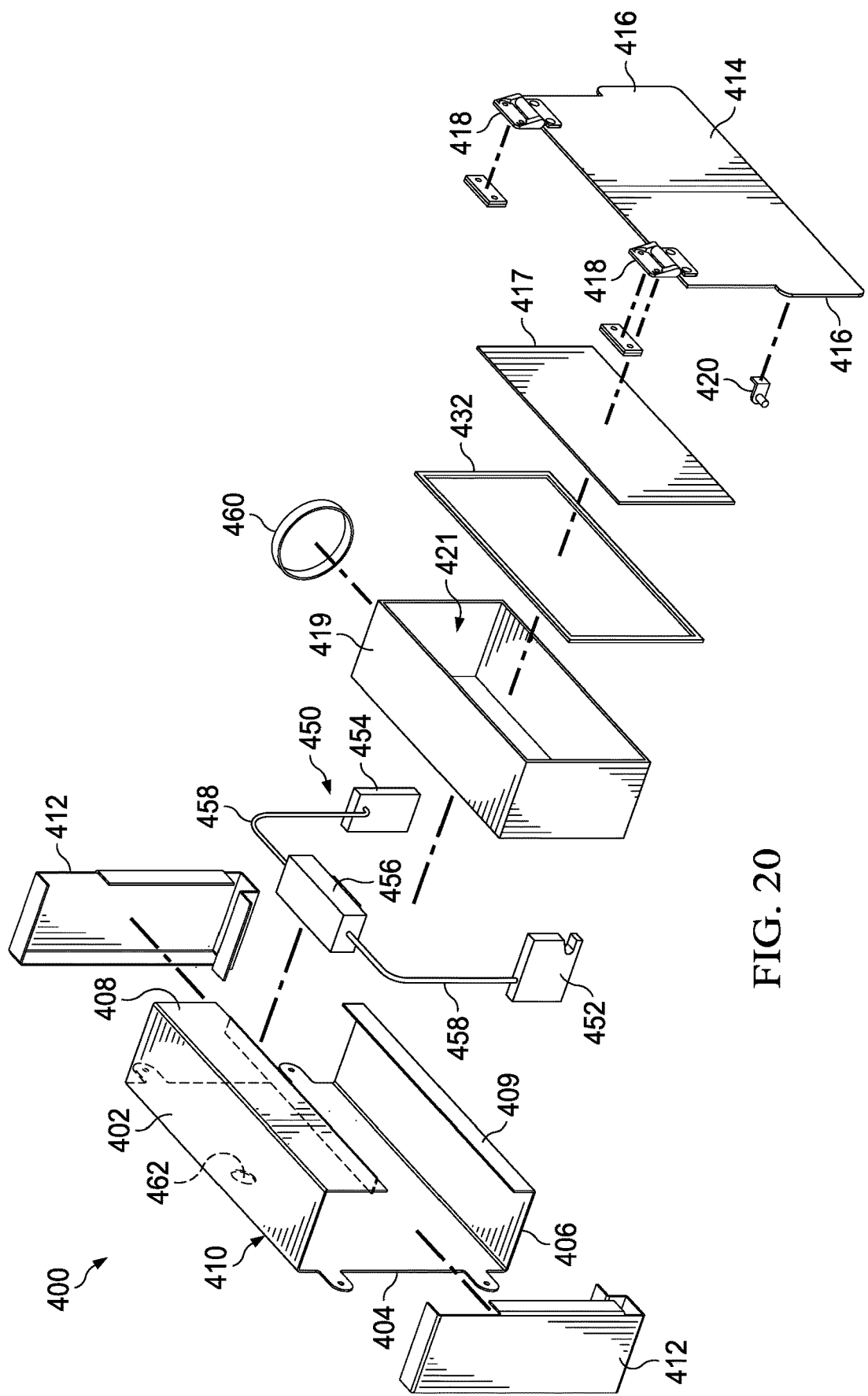
FIG. 20 is an exploded view of the device of FIG. 18.
Figure 21:
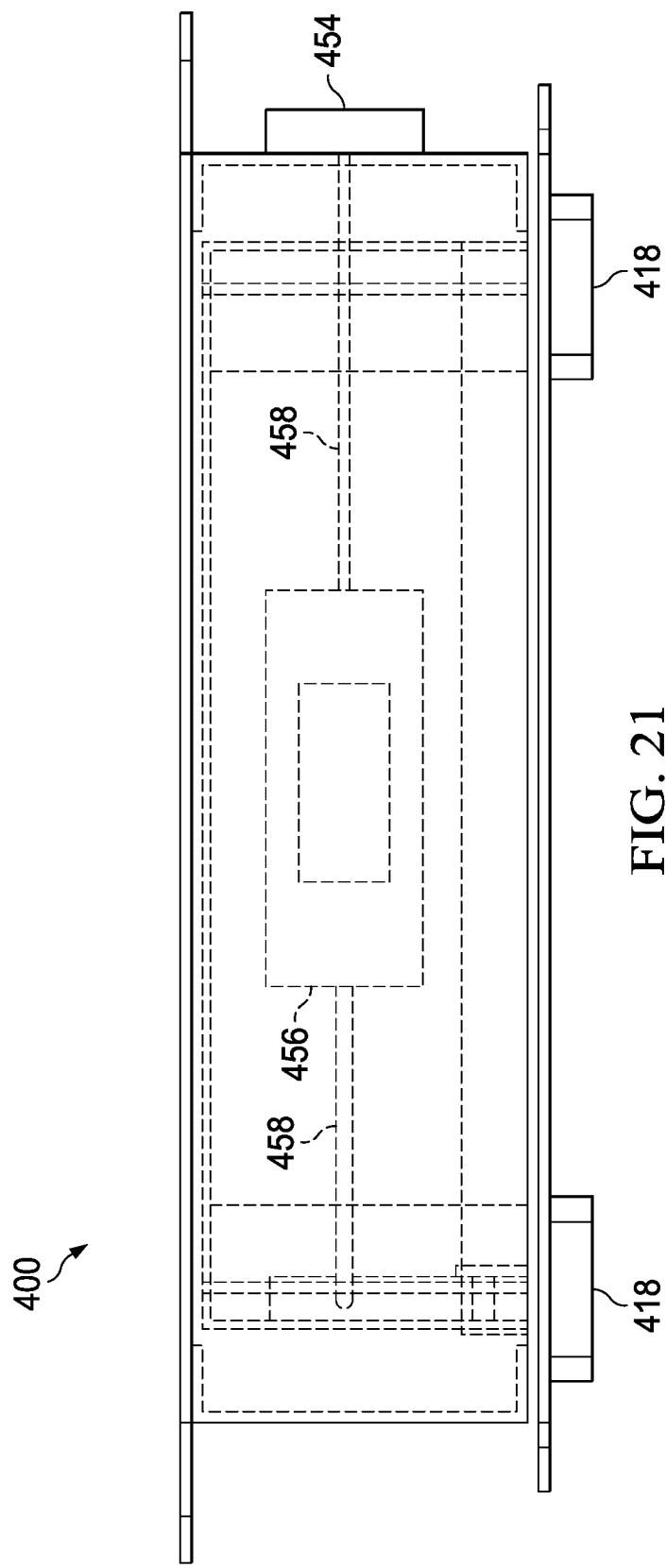
FIG. 21 is a top plan view of the device of FIG. 18 with transparency.
Figure 22:
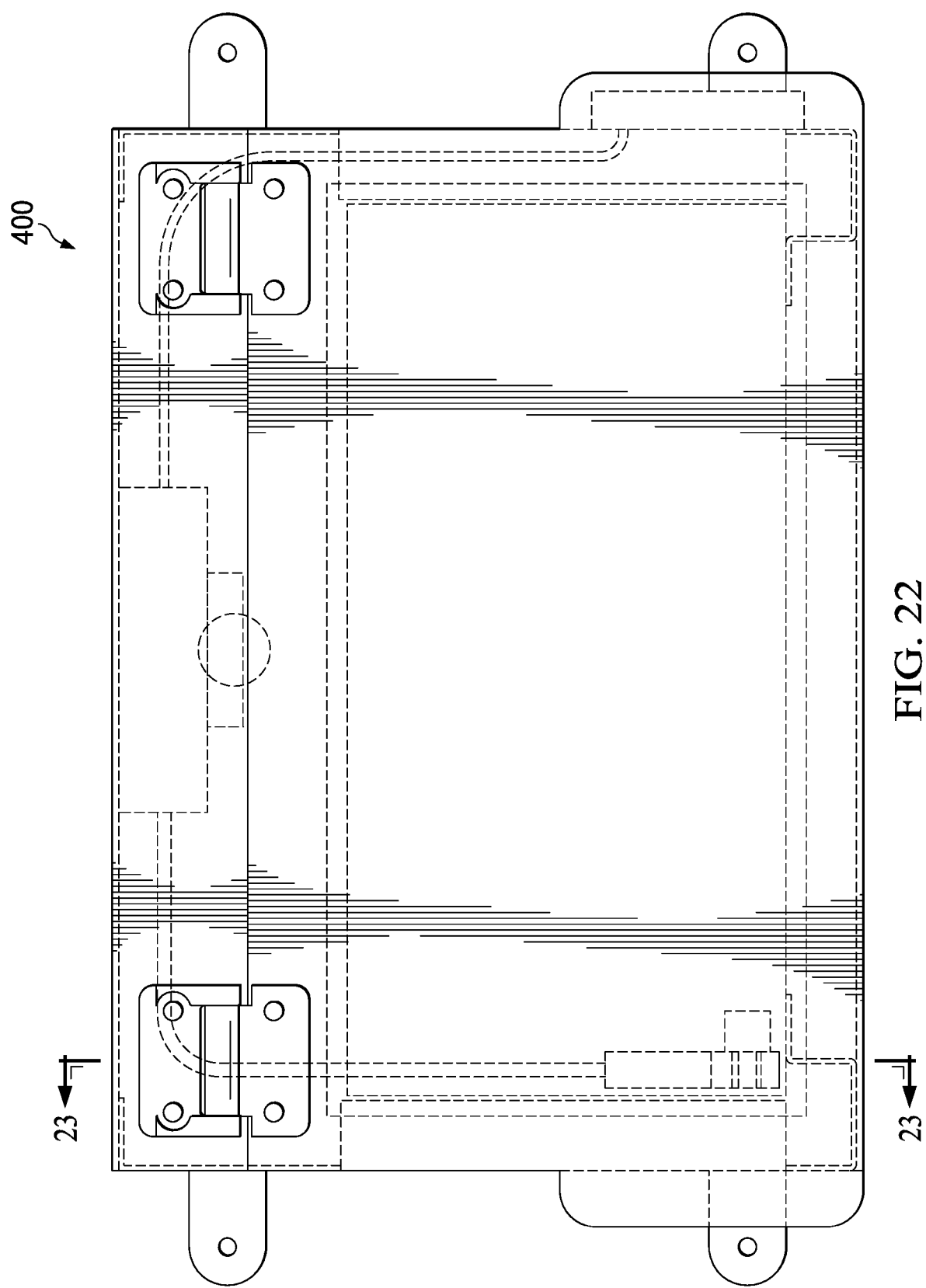
FIG. 22 is a front elevation view of the device of FIG. 18 with transparency.
Figure 23:
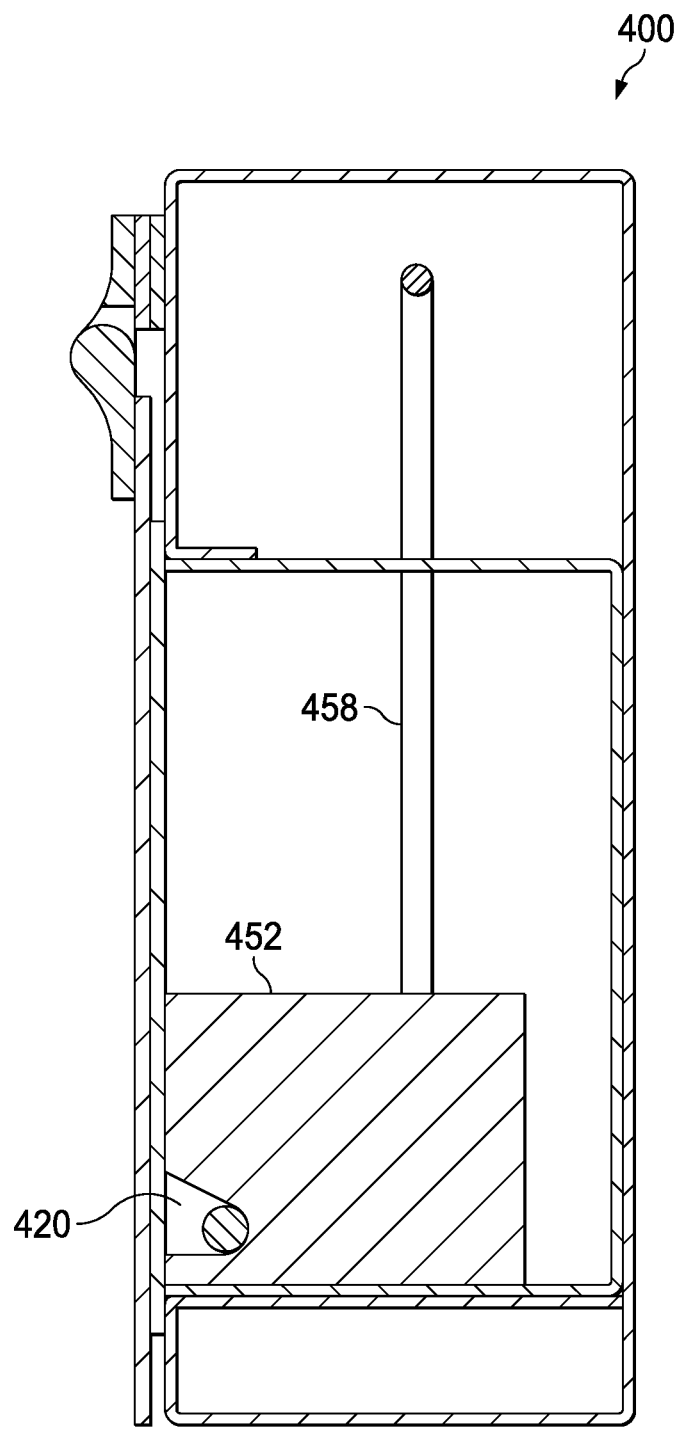
FIG. 23 is a side elevation section view taken through line 23-23 of FIG. 22.
Figure 24:
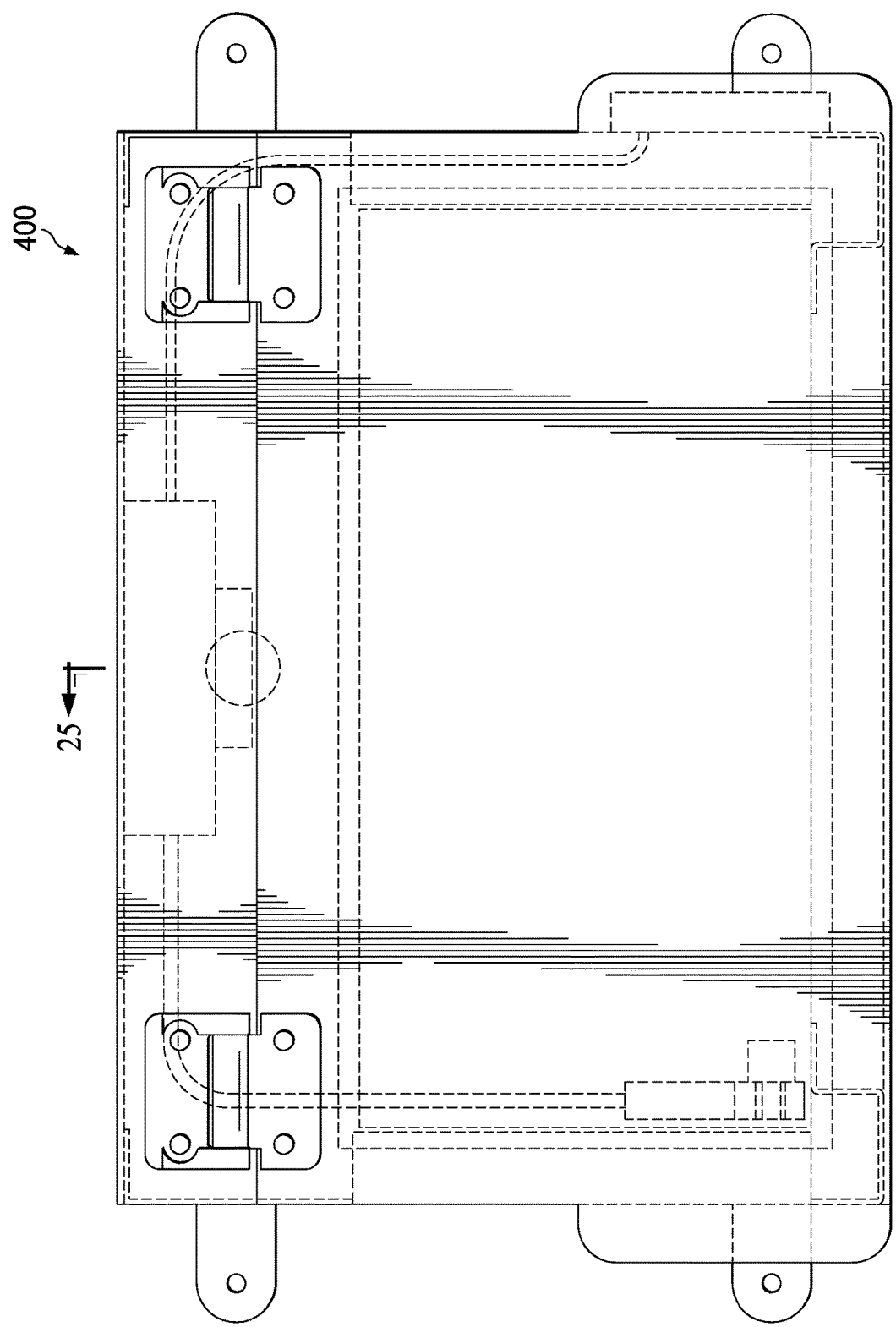
FIG. 24 is a front elevation view of the device of FIG. 18 with transparency.
Figure 25:
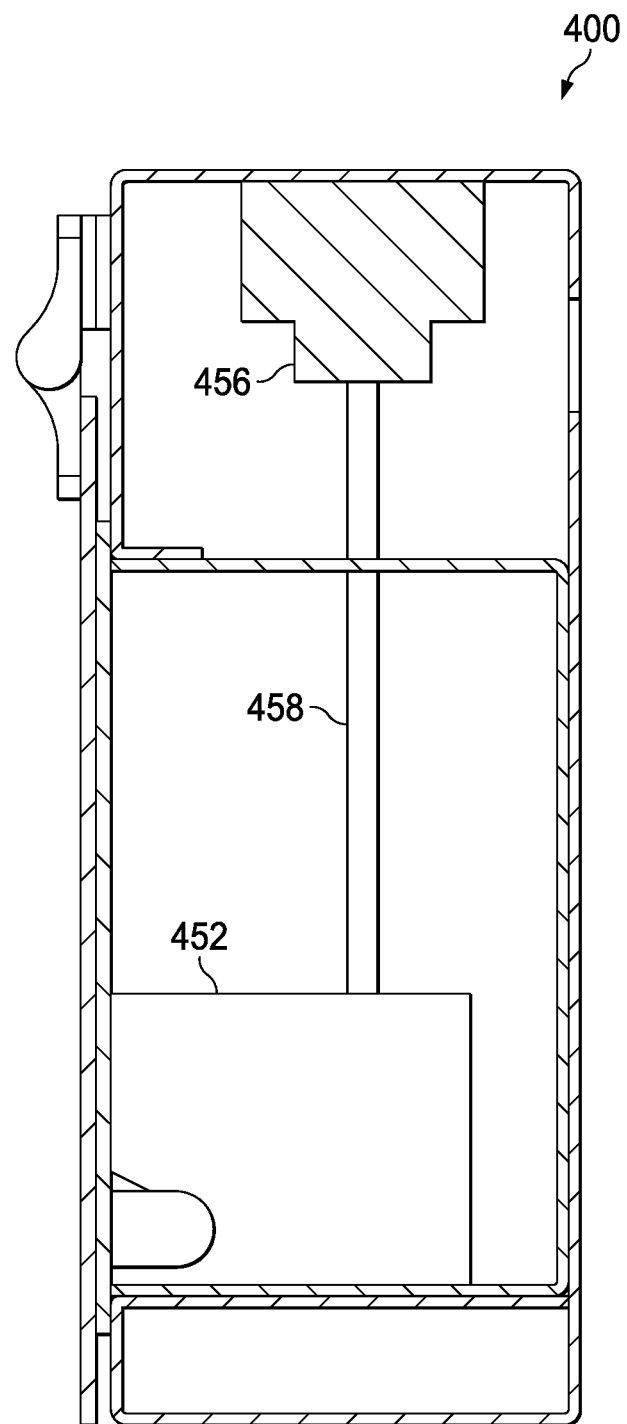
FIG. 25 is a side elevation section view taken through line 25-25 of FIG. 24.

As best shown in FIG. 20, the lip extending around the front of the distribution box 400 may further comprise a number of latches 420. The latches 420 may be configured to temporarily secure the door 414 in the closed position against the housing. The latches 420 may be magnetic devices configured to interact with the door 414 itself, magnets located thereon such that the door 414 is held securely in place against the housing until acted upon by a user, or similar spring-biased mechanical equivalents, for example.

A gasket 432 may be located along the perimeter of the front surface of the housing for the distribution box 400. In exemplary embodiments, the gasket 432 may extend along the lip created by the enclosure 410 and the side panels 412. The gasket 432 may be comprised of a conductive material and may be a foam, tape, pad, or the like. The door 416 may further be provided with additional insulation or electromagnetic shielding material, as at 417. Similarly, an interior enclosure 419 with an open face may be affixed within the enclosure 410 and generally within the box 400, wherein the open face 421 is aligned with the aperture 411. The interior enclosure 419, which surrounds the interior cavity 415, may be used to provide additional electromagnetic insulative capacity to the box 400, and provide a smooth working surface for inventory storage.

A control system 450 is also provided in the exemplary embodiment shown in connection with FIGS. 18-25. In some embodiments, the control system 450 is utilized as an access control or audit system, an inventory tracking system, or a combination thereof. In some embodiments, the distribution box 400 may be configured with an access control or audit system 450 that includes a lock mechanism 452, and authentication mechanism 454, an access control unit 456 and associated communicative coupling means 458. The distribution box 400 may also be provided with a latch 420 secured to the door 416 corresponding to and complementary to said locking mechanism 452, whereupon the door 416 is secured in default a closed position in which the box 400 cannot be opened to access its contents without proper authentication via the authentication means 454.

Depending upon the deployment environment, the authentication means 454 may be provided in a manner conducive and complementary to existing authentication means already in use at a location. For example, a lock access point may be provided which includes an RFID antenna located at a surface of the distribution box 400. The RFID antenna may be configured to communicate with a series of RFID tags 300 (as shown in FIGS. 17A-C, for example), an ID badge, or wrist band, such as the wrist band 460 depicted in connection with FIG. 20. In some embodiments, the authentication means 454 is an RFID antenna secured to the distribution box 400 outside of the shielded envelop of the box 400. When a user wearing an RFID-enabled wrist band 460 or other similar device passes the device 460 in close proximity to the lock access point 454, the RFID antenna receives the ID transmitted by the band 460, and passes the signal via conductive wire 458 to an access control unit 456 for further processing.

An electronic lock mechanism 452 is provided to couple to the door latch 420 to prevent unauthorized access to the contents of the distribution box 400. This lock receives actuation signals from the access control unit 456 via conductive wires 458, which in turn receives and processes inputs from the lock access mechanism 454. In some embodiments, RFID-enabled cards, badges, wrist bands, or bracelets 460 are provided to users, such as hospital staff, and the access control unit 456 is programmed to open the lock mechanism 452 upon a successful scan of a predetermined ID range received at the lock access device 454. In other embodiments, the distribution box 400 may be networked with the RFID inventory box system (see, e.g., FIG. 8) which it may query to determine authorized ID ranges. In the latter case, temporary ID bracelets 460 may be issued, such as for patients, wherein access to a distribution box 400 is restricted to a particular location (e.g., the patient's room) or a particular length of time (e.g., during a hospital stay).

Importantly, the invented distribution box 400 and access control system 450 may be configured to log access to the distribution box 400, either locally in a memory unit of the access control unit 456 or remotely (e.g., 150 in FIG. 8). Therefore, the distribution box 400 ensures an audit trail is created of inventory access at a granular level. A user desiring to view the audit trail may do so by accessing a web portal that provides information about the status and history of items in the box, as well as the users that have accessed the box. The web portal may also be used to change settings, including which users (RFID-enabled cards, wrist bands, or bracelets) are authorized to access the box.

In some embodiments, the lock access mechanism 454 may be configured with other alternative types of access readers, as is desired in a particular application. For example, the lock access mechanism could be provided as an RFID antenna, a biometric reader, a proximity induction-based card reader, a mag-stripe reader, a keypad, or a combination thereof.

In some cases, the distribution box 400 may further include an internal RFID antenna as part of the access control unit 456 for tracking and logging inventory items present both before and after an access event. While the box 400 may be configured with a targeted RF leak at the location of the lock access mechanism 454, exemplary embodiments may include two antennas (internal and external) shielded from one another to track box access and inventory levels. Network access, power source or both for the access control unit 456 may be achieved, for example, via an Ethernet pass-through 462 in the housing 410. Those skilled in the art will appreciate that, while an exemplary configuration of the lock 452 and latch 420 mechanism, lock access reader mechanism 454, access control unit 456 and pass-through 462 is shown in connection with FIGS. 18-25, other suitable configurations are possible without departing from the scope of the instant invention as needed for a particular application. Those skilled in the art will also appreciate that in other exemplary embodiments the box 400 may include a mechanical lock that can be accessed with a physical key in addition to the lock access mechanism. The mechanical lock may provide secondary security or be configured to override the lock access mechanism 454. In such an embodiment, the key may be used to open the box when the power is out.

The components of the distribution box 400, including but not limited to the enclosure 410 and the side panels 412, may be fastened, welded, adhered, or otherwise secured in their respective locations preferably by conductive materials. Conductive tape or other conductive material may be additionally placed along the seams of the components of the RFID box 400 so as to minimize RFID leakage. These components may be comprised of a metallic, conductive material such as, but not limited to, aluminum. Specifically, they may be comprised of 1/8" thick aluminum, though any thickness is contemplated. The use of a conductive material may serve to substantially electromagnetically "seal" the distribution box 400 thus minimizing RFID leakage, which thereby ensures accuracy in RFID readings by ensuring that an RFID antenna and RFID antenna/reader only detect RFID signals being emitted from within the RFID box 400 for accuracy and efficacy in inventory tracking procedures.

Figure 26:
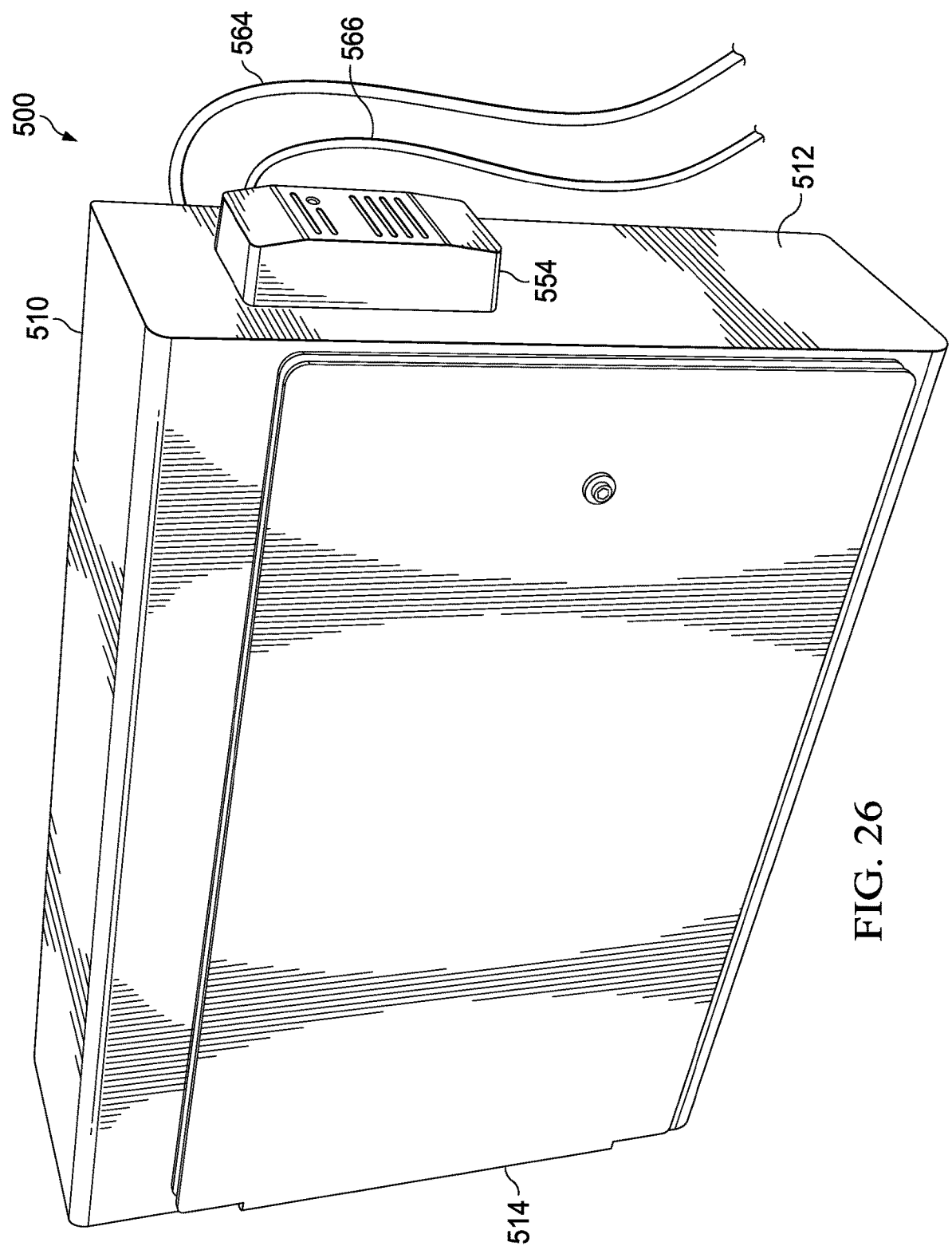
FIG. 26 is a perspective view of a further exemplary RFID distribution box.
Figure 28:
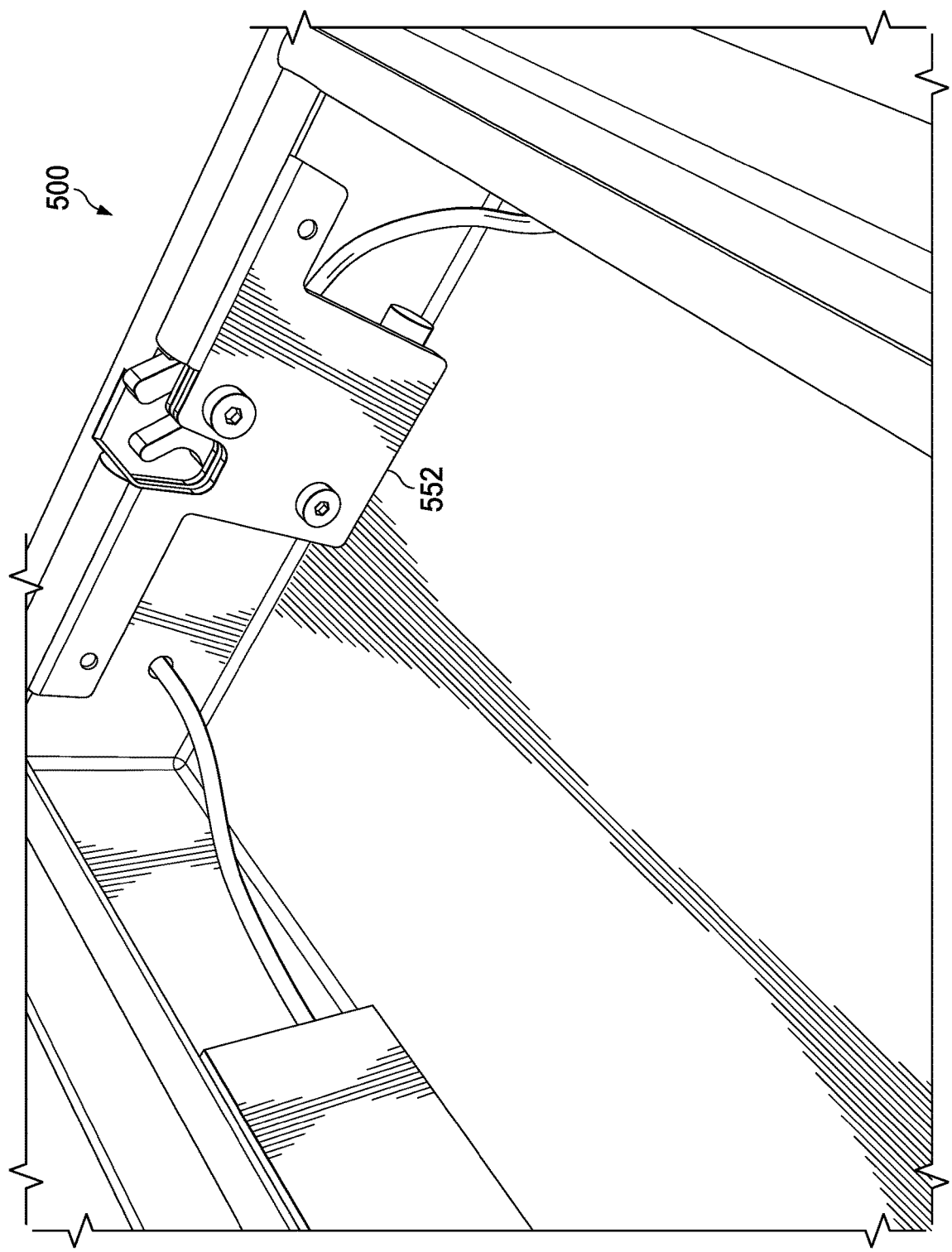
FIG. 28 is another perspective view of the device of FIG. 26.
Figure 29:
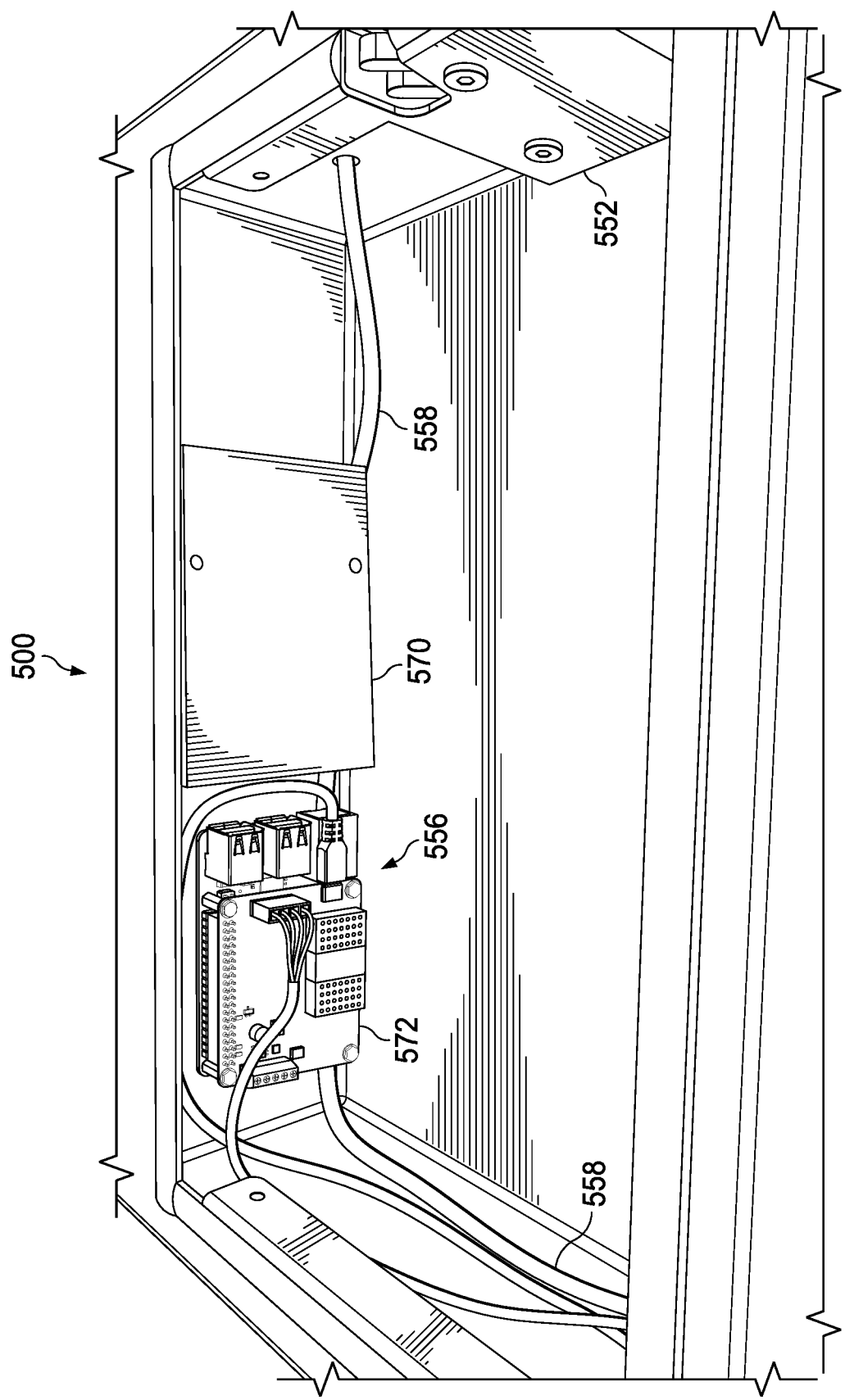
FIG. 29 is another perspective view of the device of FIG. 26.
Figure 30:
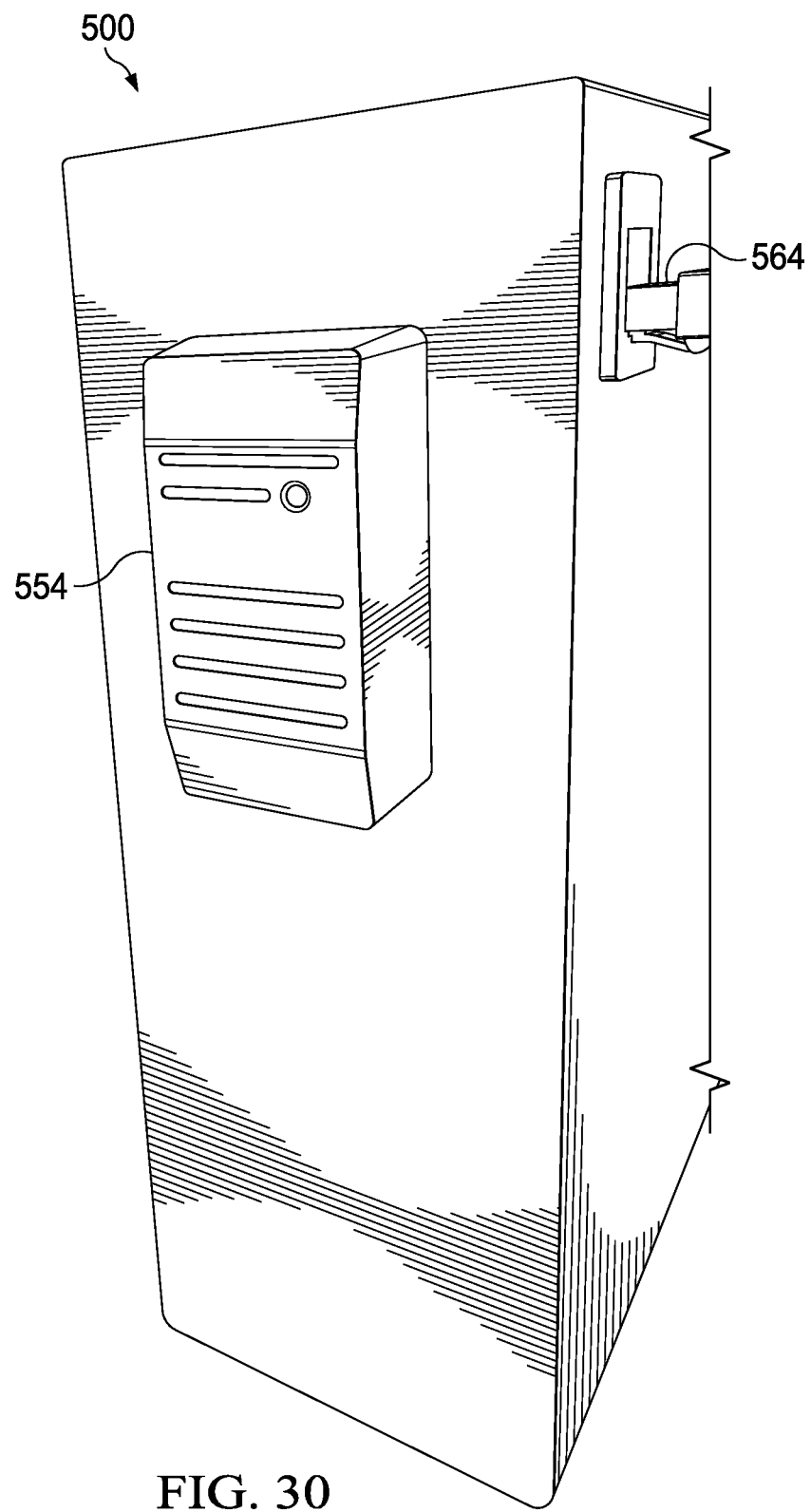
FIG. 30 is another perspective view of the device of FIG. 26.

A second exemplary embodiment of a distribution box 500 and its components are shown in connection with FIGS. 26-33. FIG. 26 depicts the exterior of the exemplary box 500, which is formed of a C-shaped housing 510, side panels 512 and a door 514. A lock access mechanism 554 is mounted to the side panel 512, and in this embodiment is an HID-brand proximity card reader unit. In other embodiments, other alternative access mechanisms may be substituted or used in conjunction with such an element as discussed above. Ethernet 564 and power 566 are shown leading to the control unit 556 inside of the enclosure 510. FIG. 30 also depicts the box 500 from a rearward side perspective, and illustrates the entry point of the network cable 564 and mounted reader unit 554.

Figure 27:
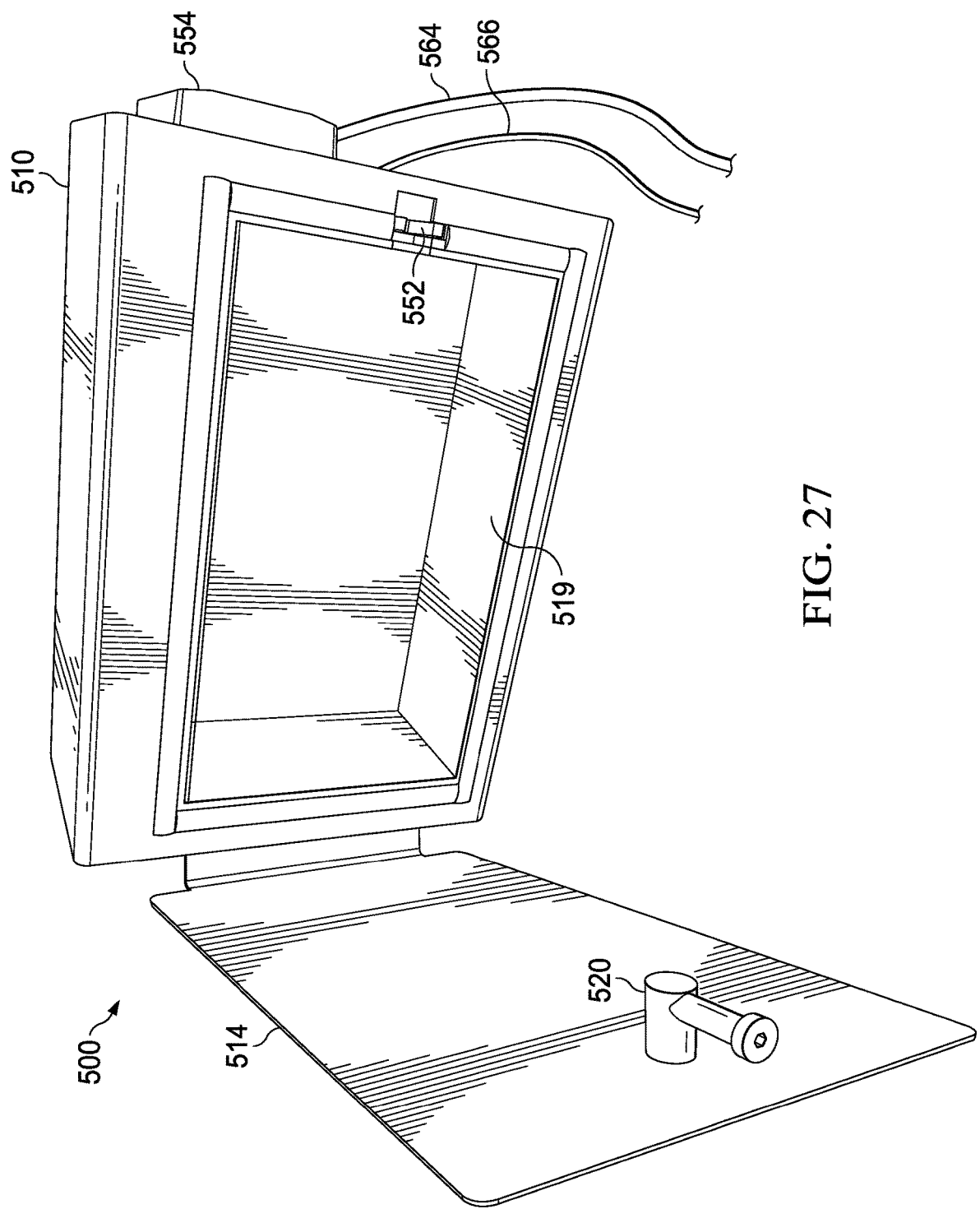
FIG. 27 is a further perspective view of the device of FIG. 26.

FIG. 27 illustrates the box 500 with the door 514 in the open position, hinged to the left side of the enclosure 510. The latch 520 is fixed to the right side of the door 514 in a position for complementary mating registration with the electronic latch 552 secured to the box 500 at the lower end of the right side panel 512, below the access reader unit 554. An interior enclosure 519 with an open face is affixed within the enclosure 510 and generally within the box 500. FIG. 28 is a perspective view of the right interior side of the box 500 with the interior enclosure removed. The electronic lock strike 552 is shown mounted therein.

Figure 31:
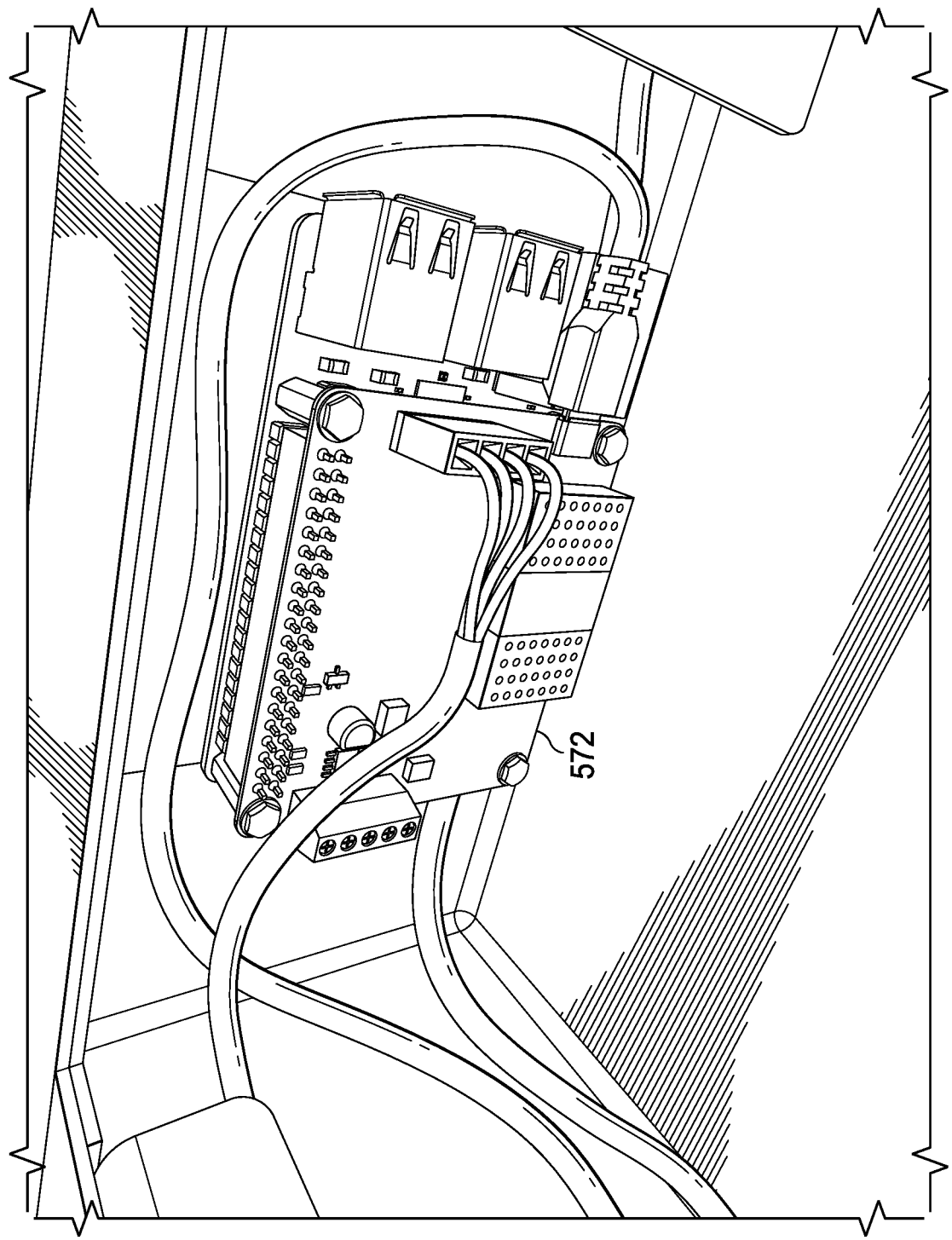
FIG. 31 is another perspective view of the device of FIG. 26.

FIG. 29 is a further perspective view of the interior of the box 500 with the interior enclosure 519 removed, primarily focused on the upper portion of the box interior. Here, the elements of the access control unit 556 can be seen, as well as electric connections 558 coupling the components of the control system generally. In this exemplary embodiment, the control unit of the box 500 can be seen to include a processing unit 570, a lock mechanism 552, connections 558, RFID reader 572 and access reader unit 554. In this embodiment, the box 500 is provided with a ThingMagic M6E-MICRO RFID reader unit 572, which is used to receive RFID signals from inventory items and kit baskets placed within or removed from the box 500. The processing unit 570 utilizes a Raspberry Pi 3 Model B Motherboard for processing the RFID information received from the reader 572 and the access reader unit 554, and handling network communications and lock mechanism 552 actuation. FIG. 31 shows a second view of the reader unit 572 for clarity.

Figure 32:
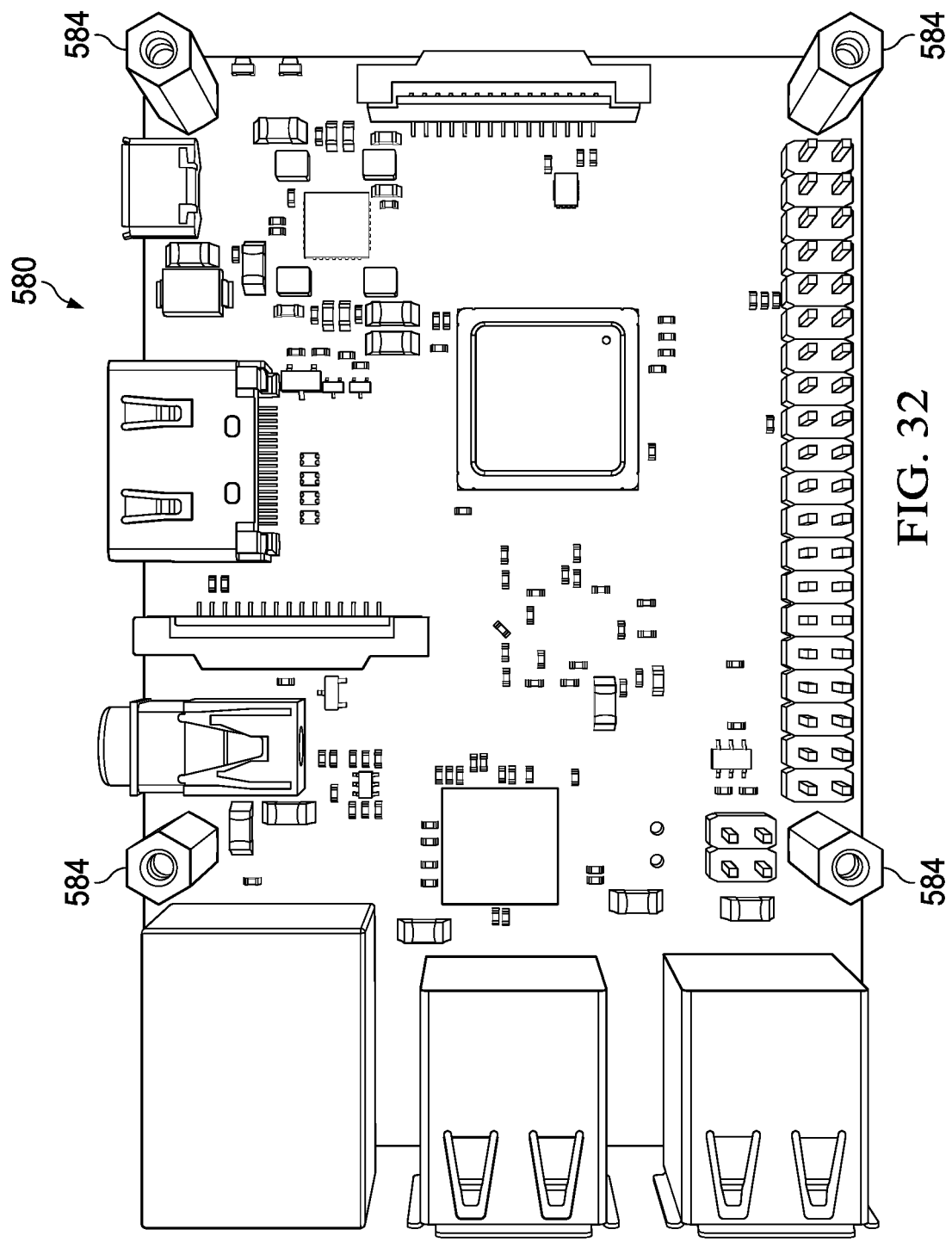
FIG. 32 is a plan view of an element of a process control unit of the device of FIG. 26.
Figure 33:
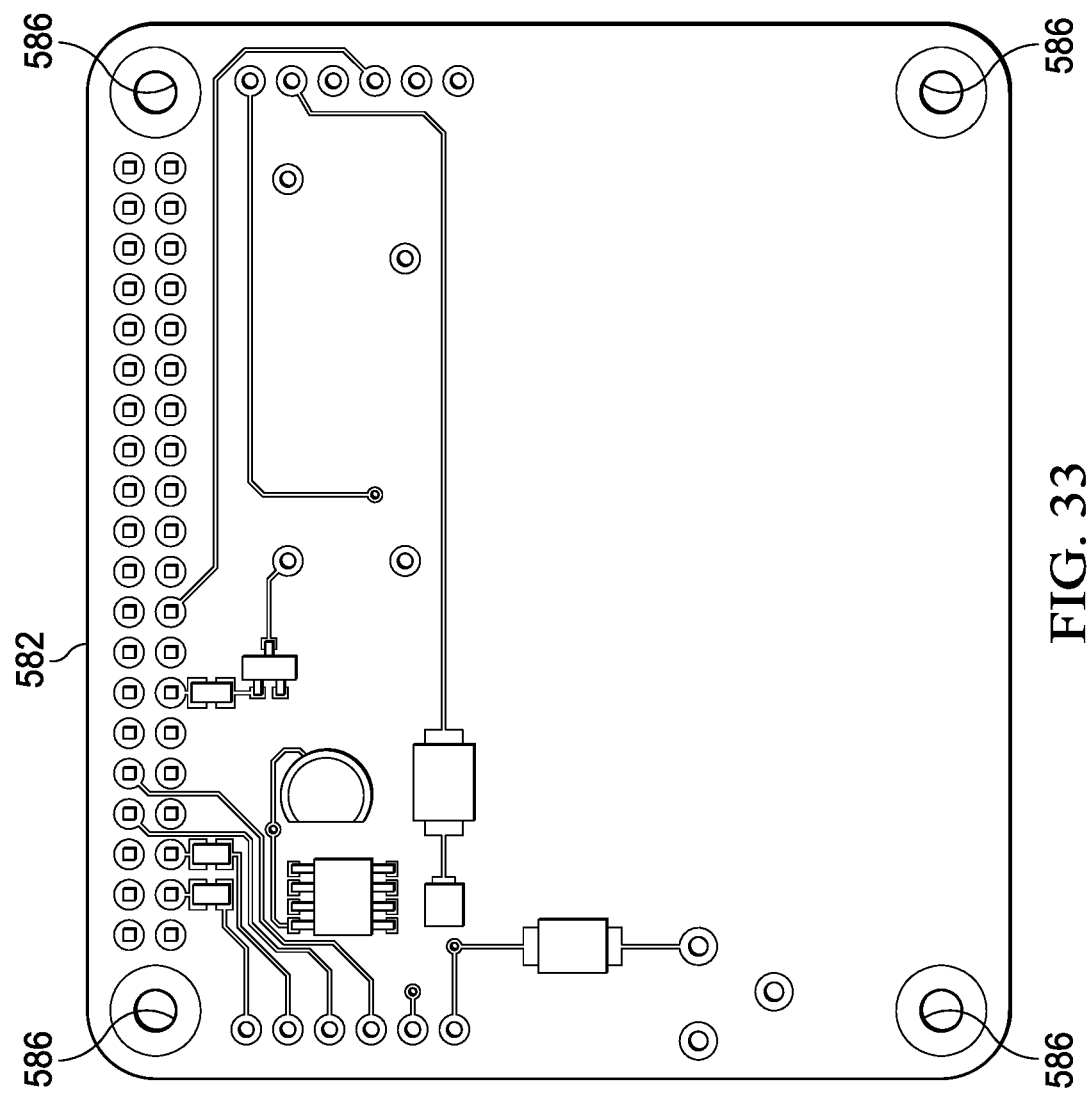
FIG. 33 is a plan view of an element of a process control unit of the device of FIG. 26.

FIGS. 32 and 33 depict components of the processing unit 570 used in this exemplary embodiment. The Raspberry Pi 3 Model B Motherboard 580 is shown in FIG. 32, and a daughter card 582 is shown in FIG. 33. The daughter card 582 is secured to the motherboard 580 via threaded fasteners (not shown) screwed into the threaded mounts 584 on the motherboard, via apertures 586 in the daughter card. The daughter card provides the necessary circuitry for actuation of the lock mechanism 552 with suitable boosts to voltage.

In certain embodiments, the processing unit 570 allows for local processing of authorization requests and comparison of baseline information against inventory scans. While changes in user roles and changes to baseline information may be effected through a web portal, the box 500 can perform many operations locally, allowing it to maintain operability even when network/internet connection is unavailable.

Figure 34:
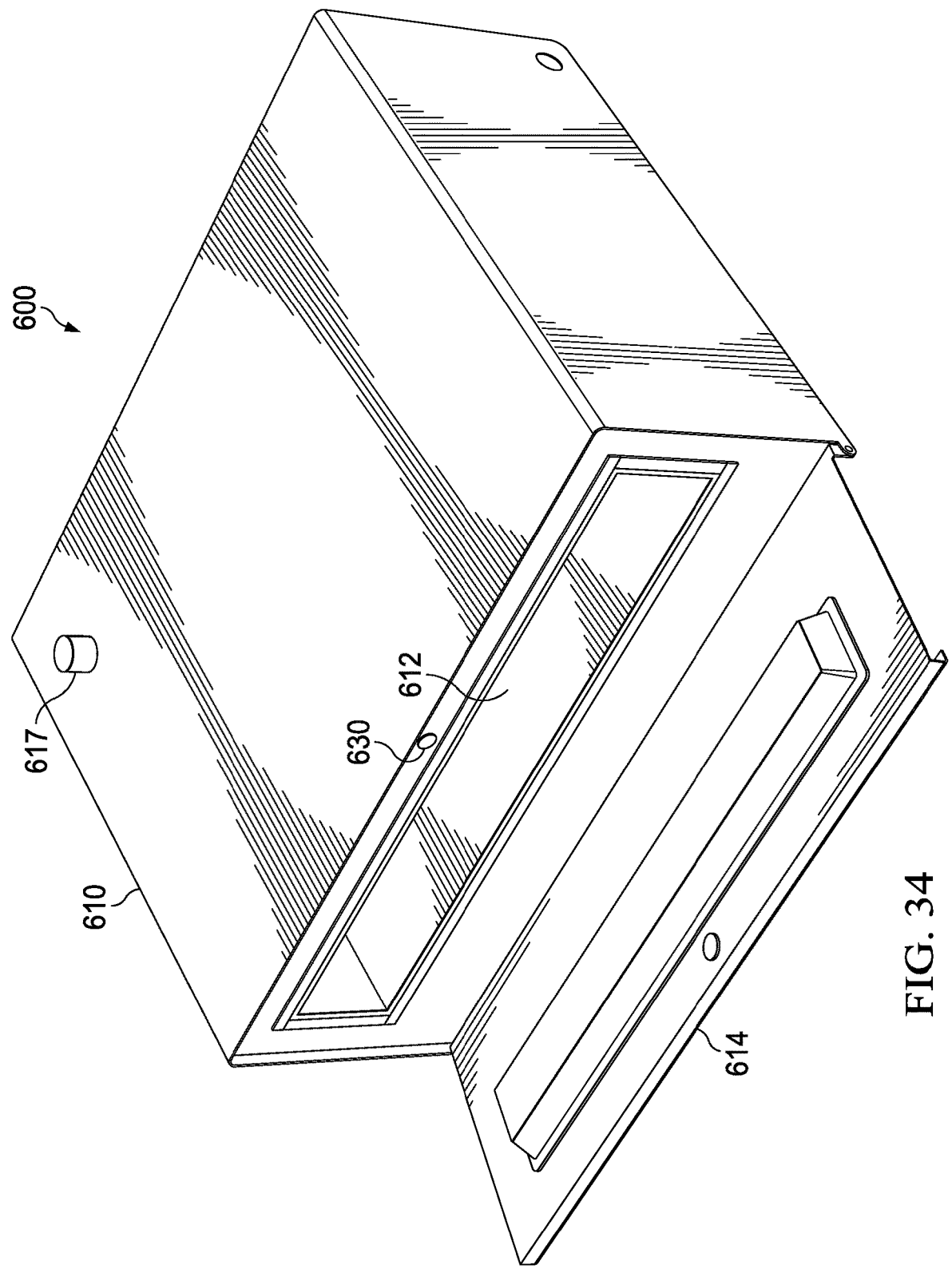
FIG. 34 is a perspective view of a further exemplary RFID distribution box.
Figure 35:
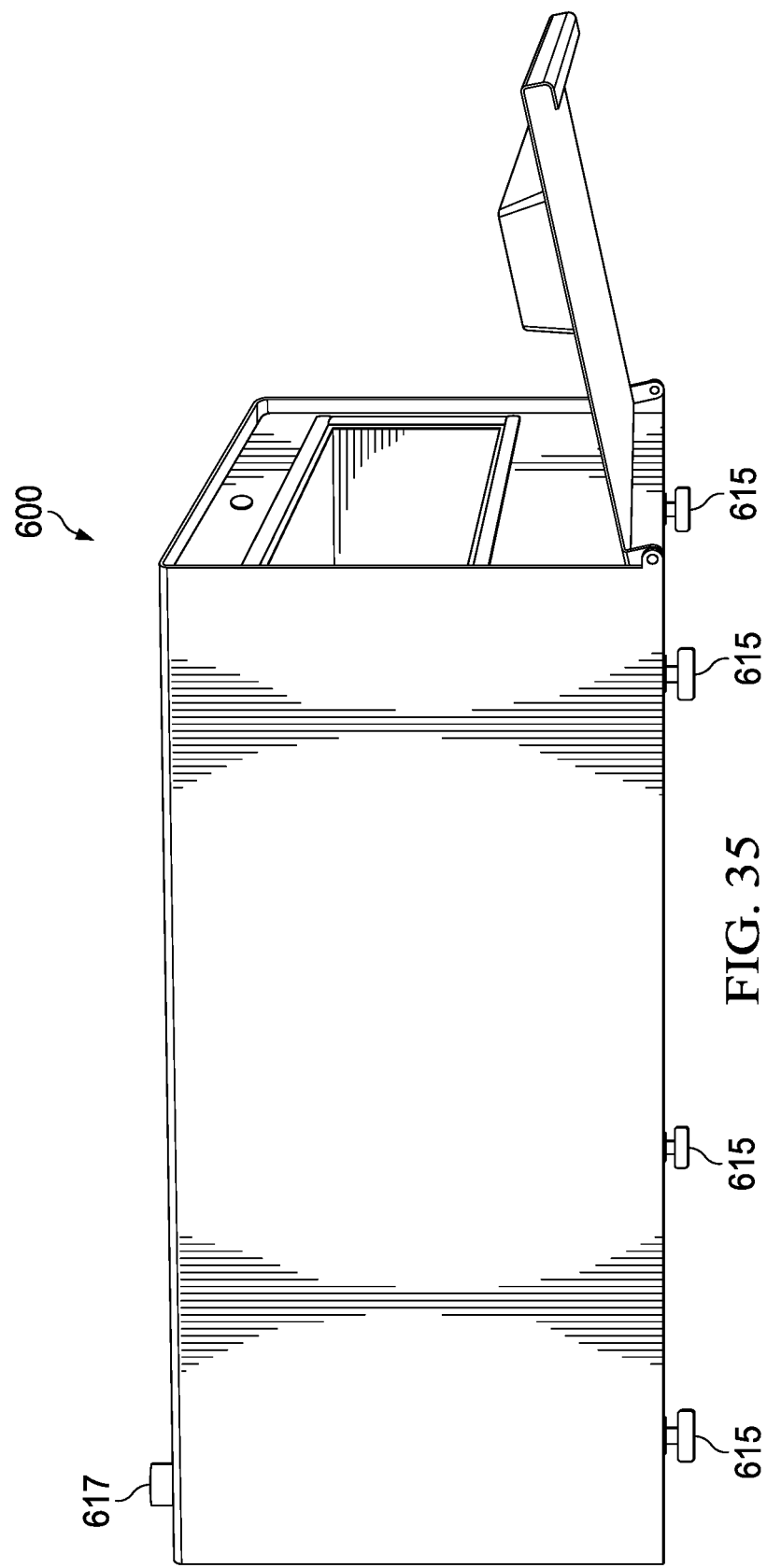
FIG. 35 is another perspective view of the device of FIG. 34.
Figure 36:
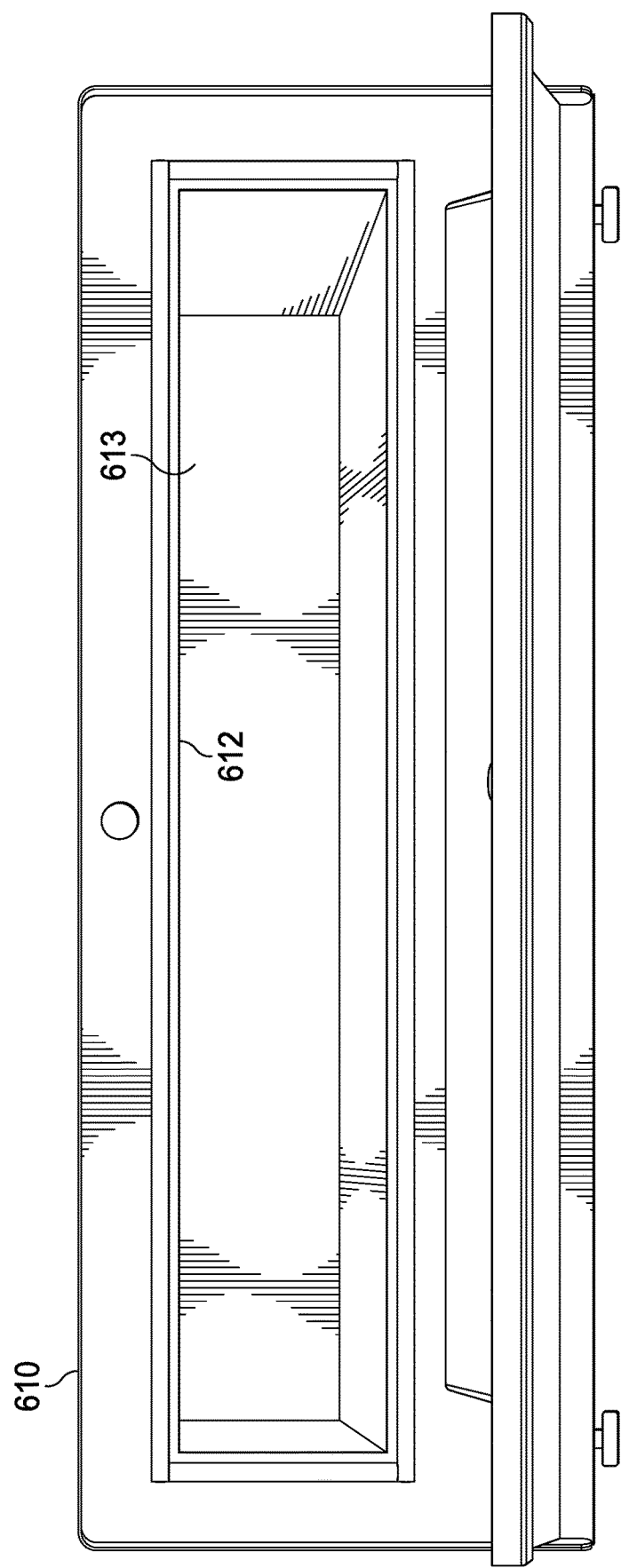
FIG. 36 is a front elevation view of the device of FIG. 34.
Figure 37:
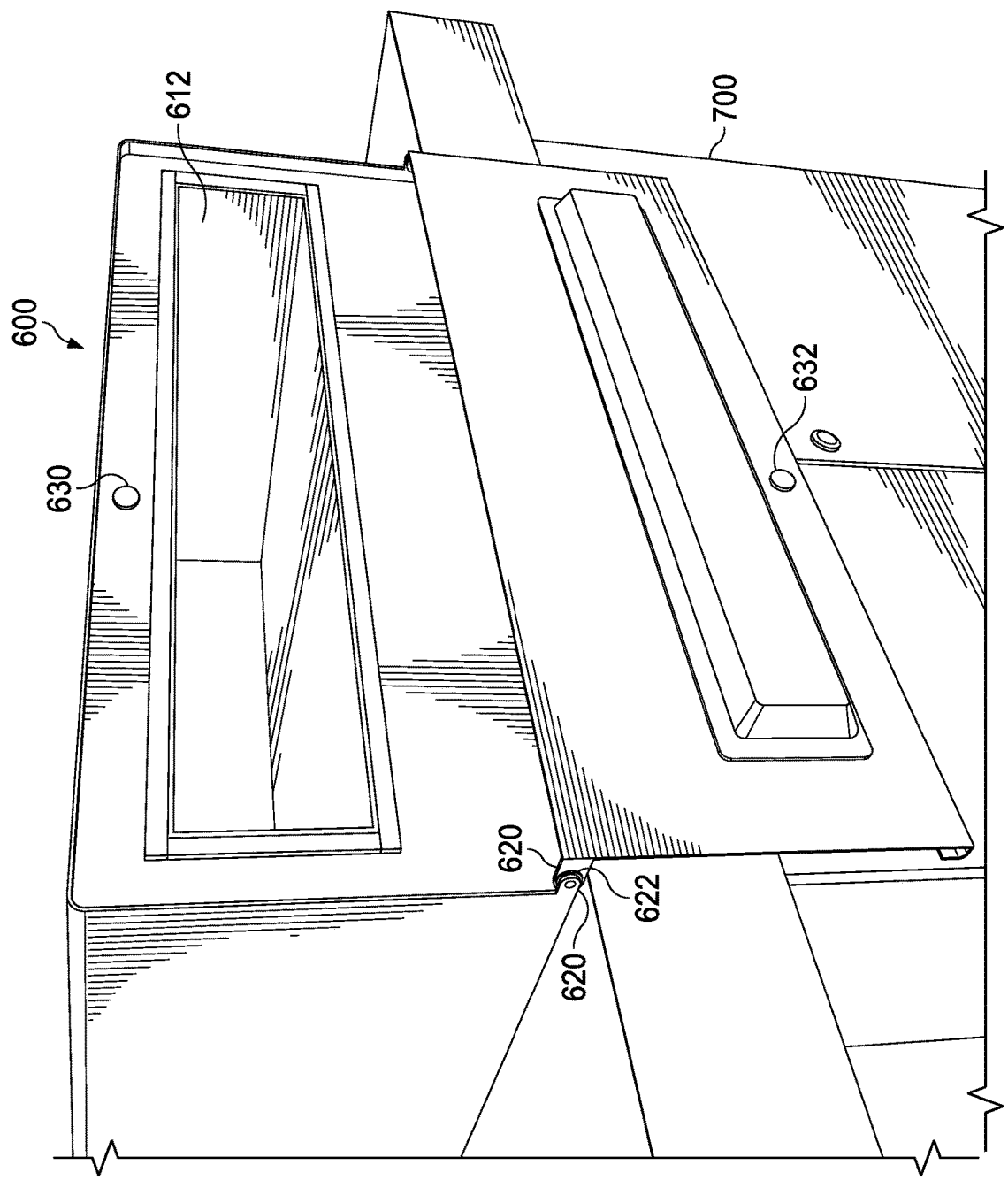
FIG. 37 is another perspective view of the device of FIG. 34.

Another embodiment of a distribution box 600 having different shape and size is shown in connection with FIGS. 34 through 37. FIG. 34 depicts the exterior of the exemplary box 600, which is formed of a housing 610 and a door 614. In this embodiment, and as best seen in FIG. 37, the door hinges are comprised of tabs 620 formed from the same sheets of metal as the door and cabinet, with a bearing 622 in-between, providing for a seamless appearance. A lock access mechanism (not shown) and card reader unit (not shown) may be mounted to the housing 610 as desired. An interior enclosure 612 defines an interior cavity 613 for receiving items. The box and cavity may be sized to receive a single tray containing pharmaceutical items and/or other items. In an exemplary embodiment, the dimensions of the interior cavity 613 may be 24.5 inches in width, 3.875 inches in height, and 16.7 inches in depth. Of course, in other embodiments the dimensions of the interior cavity 613 may vary as desired. While this embodiment could be attached to a wall, it may also be placed on a surface such as a counter top or on top of a cabinet 700, as shown in FIG. 37. In some embodiments the box may contain bottom brackets allowing it to be secured to surface. The compact nature of the box allows it to be used in locations that may have little space available, such as a fire station.

As shown in FIGS. 35 and 36, the box 600 has four adjustable feet 615, each located at a bottom corner of the box, which may be adjusted as necessary to allow the box 600 to be level or avoid wobbling when in use.

The box 600 may have a status light 617 located on the housing. The status light 617 may display one or more colors that communicate information to a user. In an exemplary embodiment, the light can turn green, orange and red. When a scan reveals that all items are present, and all items are unexpired, the light 617 may be green. A user can take one look at the box and upon seeing the green light know that there is no need to replace any expired items, and that all items are present. The light 617 turns orange when one or more items are expired, providing a visual notification to the user that restocking is necessary. When the scan indicates that according to baseline box content data an item is missing, the box may turn red, again providing a visual notification to the user that restocking is necessary and possibly a review of the audit records is necessary as well to see what user removed the item. Of course, in different embodiments, the light may be configured in different ways. The light may be an LED light in electronic communication with the motherboard 580. The box 600 may be powered by PoE (power over ethernet) or other means. An ethernet port may be located on its back side or other surface. In some embodiments, the box may include a battery to allow it to remain operable when the power goes out or during transport.

This embodiment may have a mechanical lock in addition to the lock operated by the lock access mechanism. The mechanical lock may be completely separate to and provide a secondary level of security to the lock access mechanism. This may allow for increased security. The mechanical lock may also be configured to override the lock access mechanism in times when the power is out or in other emergency situations.

Different embodiments may also have a display screen integrated into the box itself to provide written notifications to users. For example, the screen may display the name of a pharmaceutical item that has expired along with its expiration date. In some embodiments, the screen may display the name of the last user that has accessed the box. The screen may be sized such that it can only provide a few words to a user or it may be larger and even have touch-screen capabilities to allow users to configure settings, enter queries, or otherwise obtain information about contents and access history.

It will be appreciated by one of ordinary skill in the art that a box shaped like the embodiment in FIGS. 34 through 37 may contain many of the features shown in other embodiments of the figures as desired to provide a convenient solution to a consumer.

FIGS. 38 through 46 illustrate an exemplary embodiment of a double door RFID box 700. In this exemplary embodiment, the RFID box 700 is rectangular in shape and comprises a housing 710. The housing 710 is comprised of a front side 712, left side 714, right side 716, top side 718, bottom side 720, and back side 722, surrounding an inner cavity 724.

Located on the front side 712 of the housing 710 is an outer door 726 which may be attached to the housing 710 by a hinge mechanisms 728. In the exemplary embodiment of FIGS. 38-46, the hinge mechanism 728 movably connects the left side of the outer door 726 to the left edge of the front side 712 of the housing 710. In other embodiments, different means may be used to connect the outer door 726 to the housing in a variety of ways. As shown at least in FIGS. 38, 41 and 44, the outer door 726 may have a lip 729 on the end opposite the hinge mechanism 728 that extends away from the outer door 726 in a curving fashion in order to aid a user in manually opening and closing the outer door 726.

Figure 38:
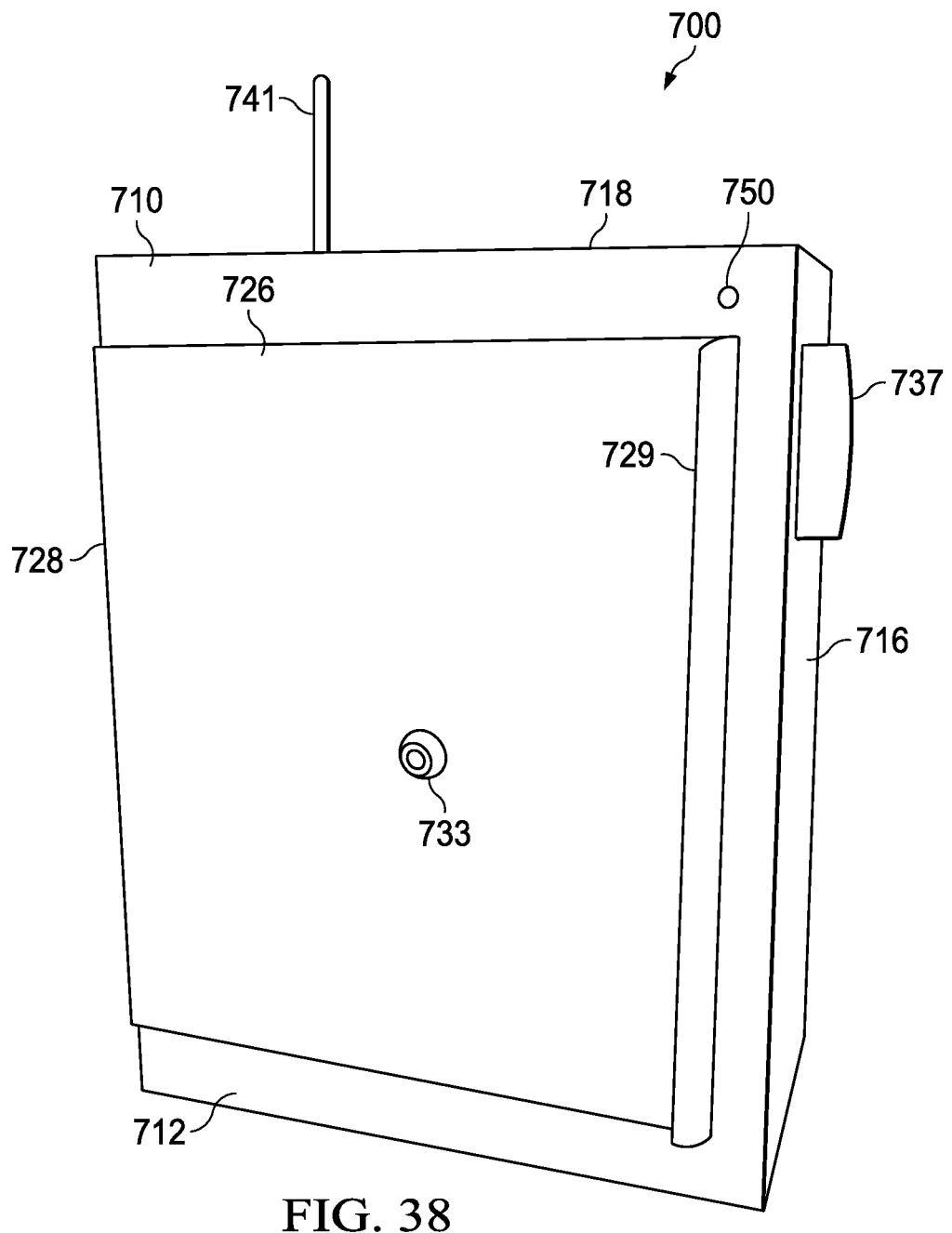
FIG. 38 is a perspective view of an exemplary embodiment of a double door RFID box.
Figure 39:
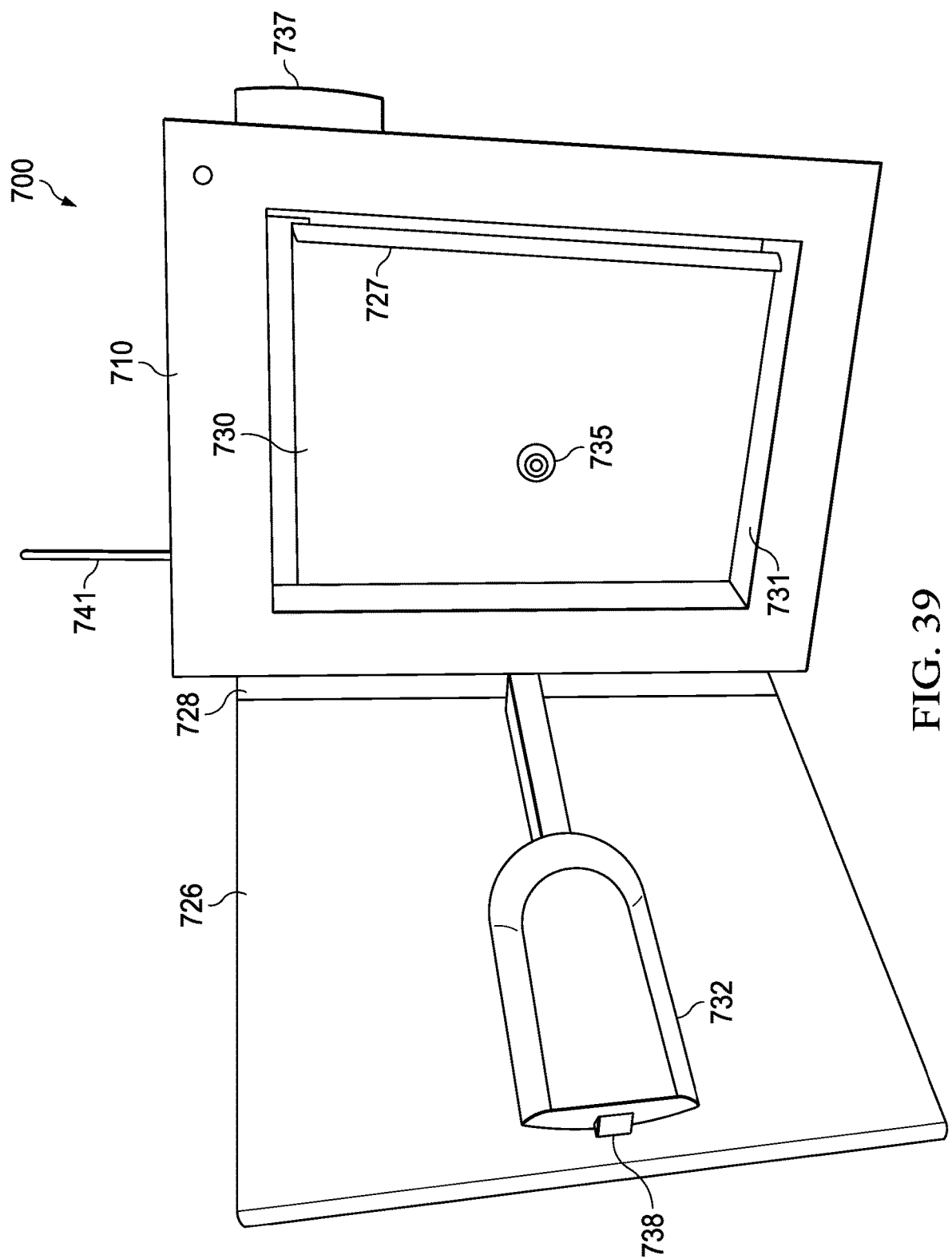
FIG. 39 is a perspective view of the exemplary embodiment of FIG. 38, with the outer door in an open position.
Figure 40:
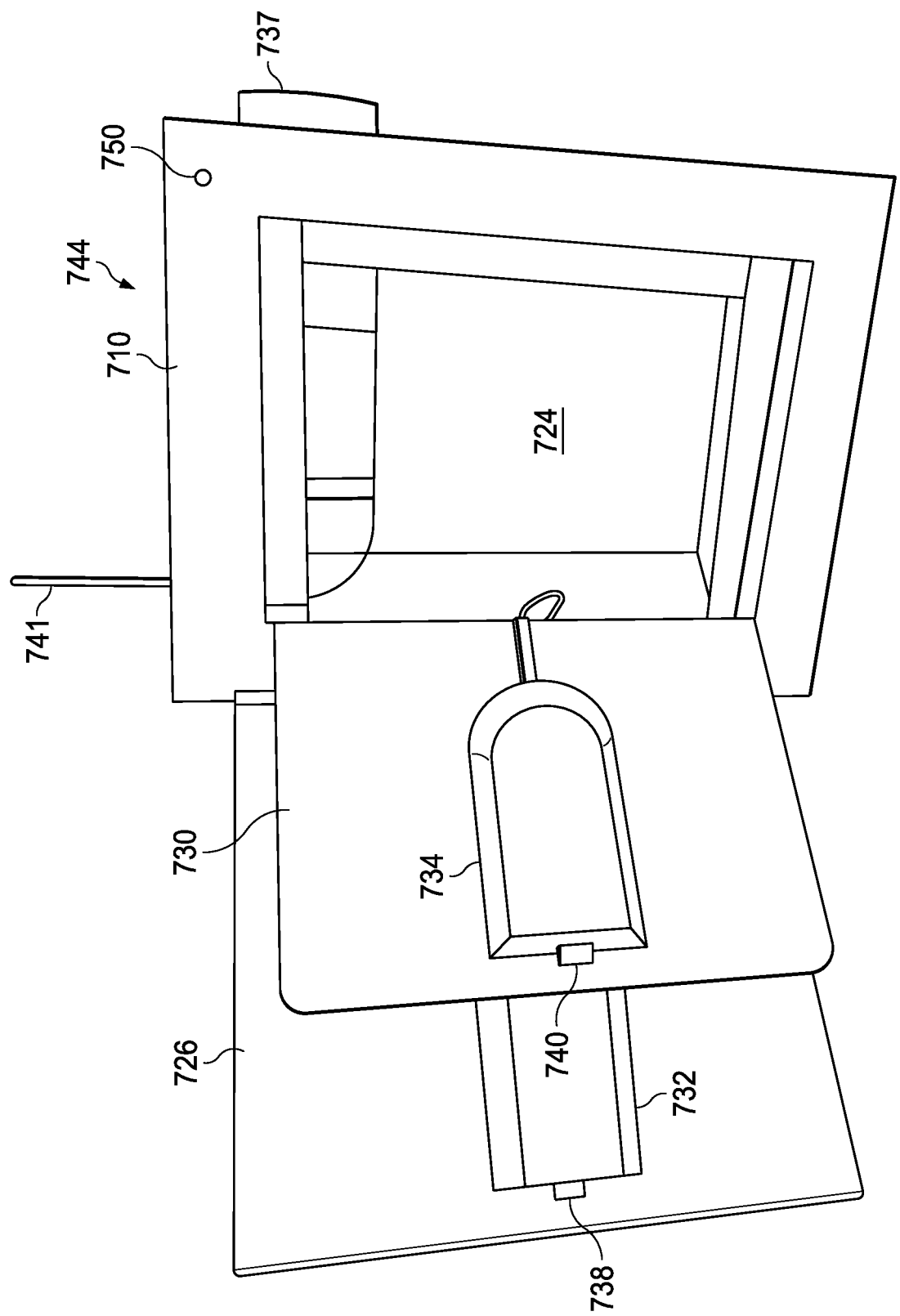
FIG. 40 is a perspective view of the exemplary embodiment of FIG. 38, with both the outer and inner doors in an open position.
Figure 42:
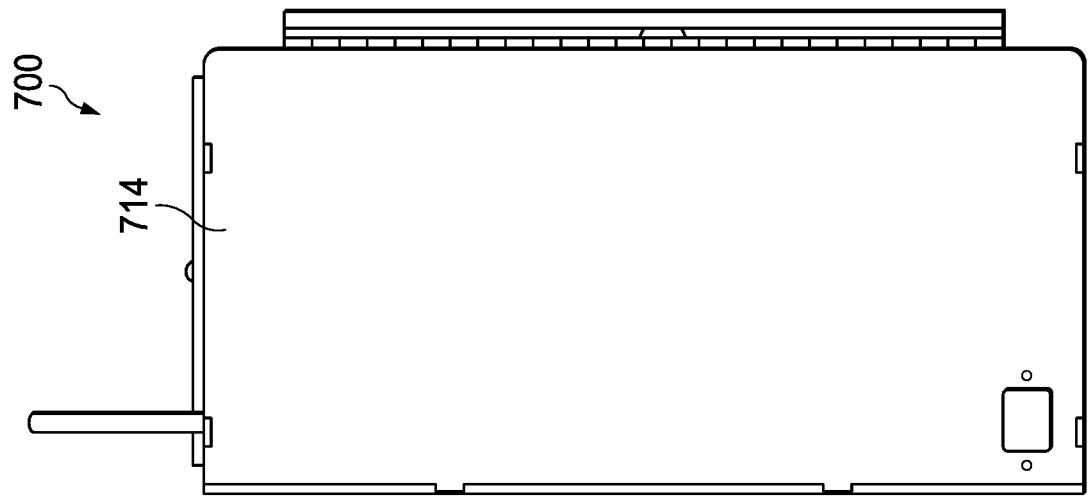
FIG. 42 is a left side elevational view of the exemplary embodiment of FIG. 38 with the doors in a closed position.
Figure 41:
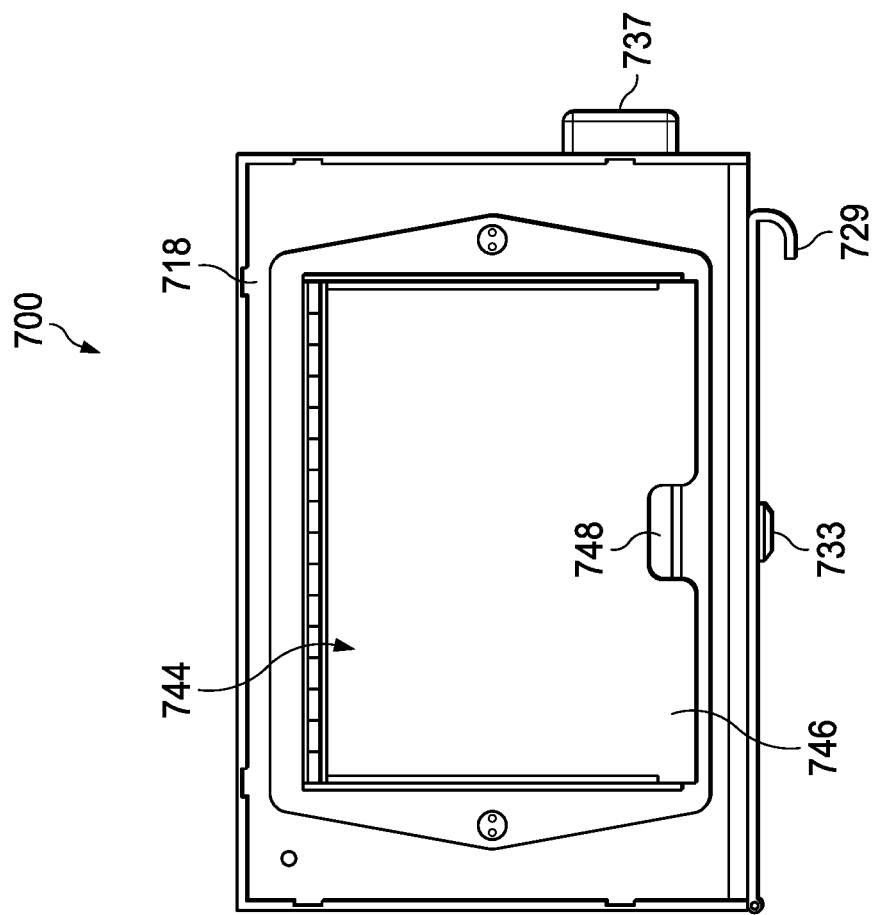
FIG. 41 is a top plan view of the exemplary embodiment of FIG. 38; with the doors in a closed position.
Figure 43:
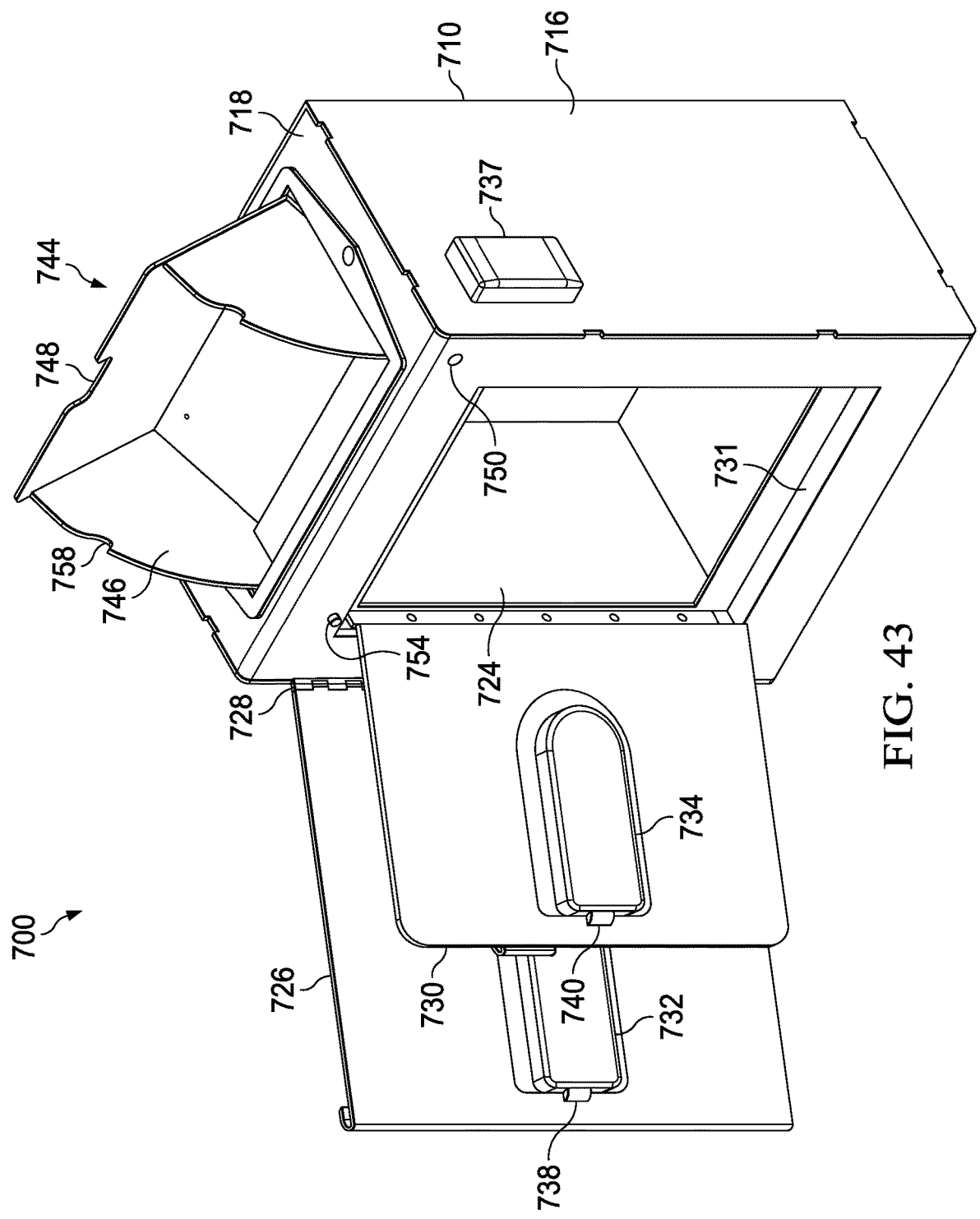
FIG. 43 is a perspective view of the exemplary embodiment of FIG. 38, with the doors in an open position and the drop box in and open position.
Figure 44:
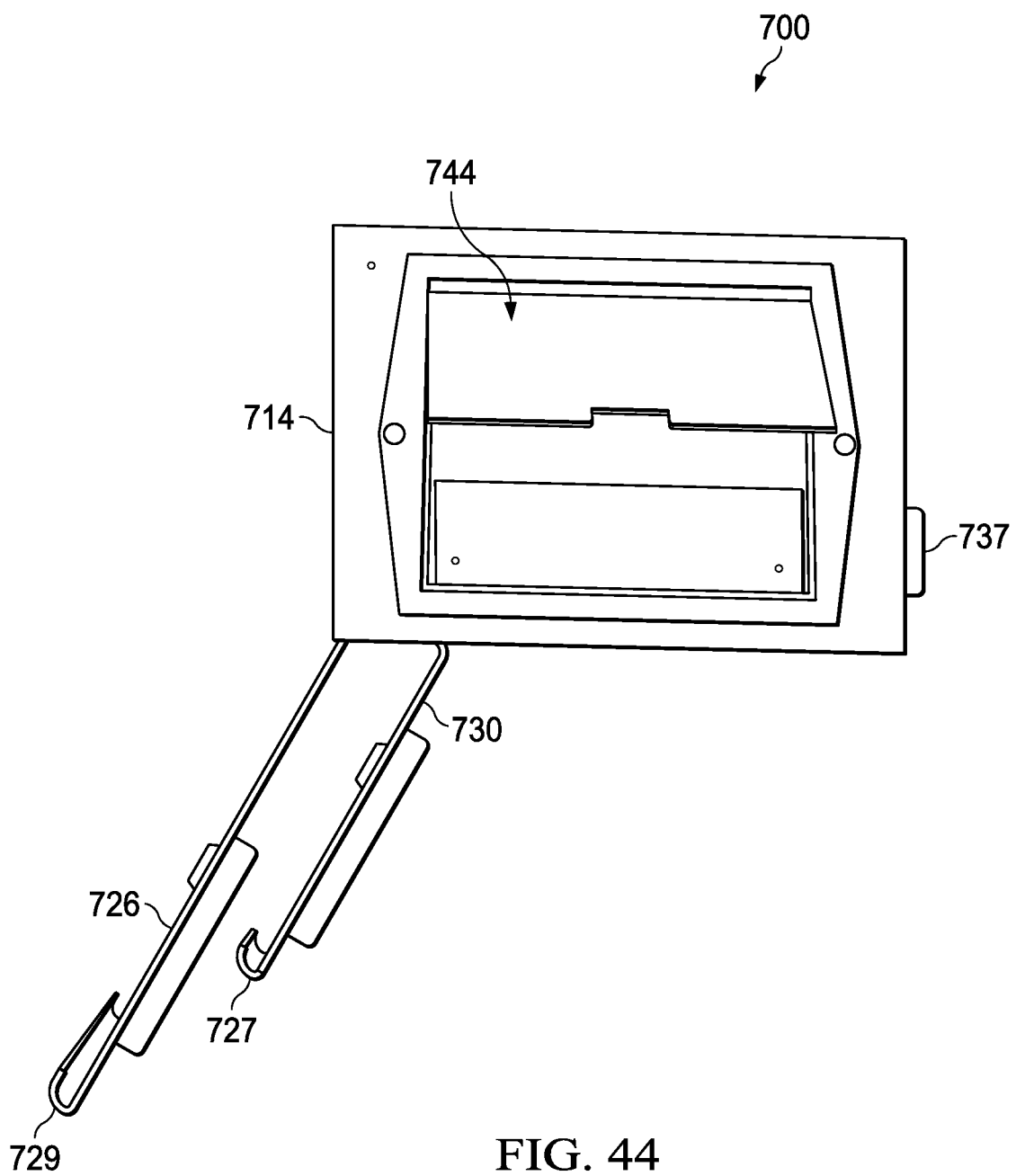
FIG. 44 is a top plan view of the exemplary embodiment of FIG. 38, with the doors in an open position and the drop box in an open position.

While in FIG. 38 the outer door 726 is shown in a closed position, in FIG. 39 the outer door 726 is shown in a substantially open position, wherein a user can view and access an inner door 730 located in a recess 731 in the front side 712 of the housing 710. The inner door 730 is connected to the recessed wall via a hinge mechanism. The inner door also has a lip 727 that can be used to manually move the door. FIGS. 40, 43, and 44 show the box 700 with both the outer door 726 and inner door 730 in open positions, allowing a user access to the inner cavity 724 of the box 700.

In this exemplary embodiment both the outer door 726 and inner door 730 are associated with electromechanical lock access mechanisms 732, 734 to allow for access into the RFID box. Each of the lock access mechanisms 732, 734 are electrically actuated, but also contain manual override locks 733, 735 that can bypass the electric actuation. The manual override locks 733, 735 can be accessed from the front face of the outer and inner doors 726, 730. The manual override locks 733, 735 may be keyed differently such that two different keys are needed to open both the outer and inner doors. Manual access may be necessary in the event of an electrical outage or the box 700 otherwise loses access to a power supply. Each lock access mechanism 732, 734 comprises a latch 738, 740 on the back side of its respective door that insertably engages with an aperture located in the housing 710 when in the "locked" orientation (apertures not shown). The apertures may be located within the recess 731 on the front side 712 of the housing.

Figure 45B:
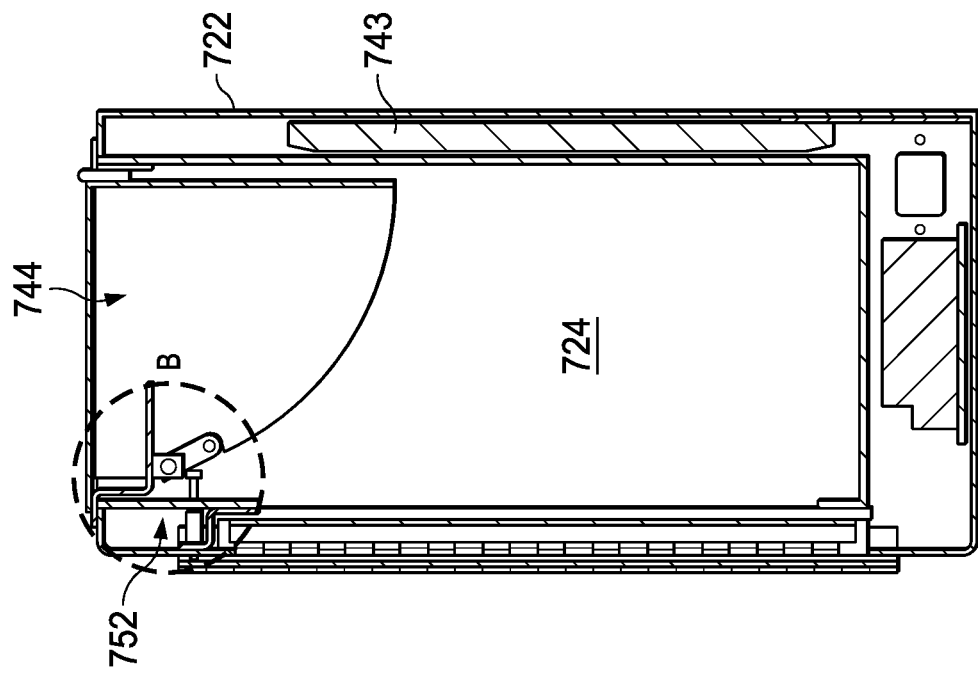
FIG. 45B is a side sectional view taken along section line A-A of FIG. 45A.
Figure 45A:
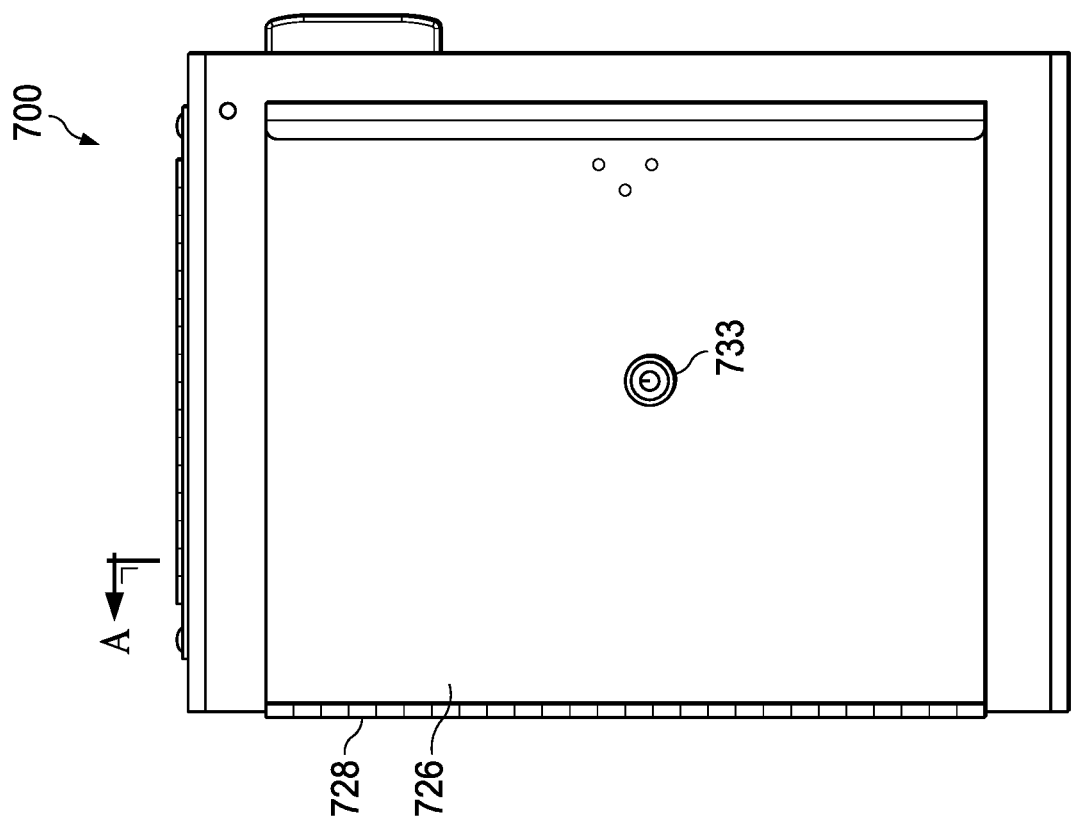
FIG. 45A is a front elevational view of the exemplary embodiment of FIG. 38.

The RFID box 700 includes an internal processing unit for controlling operations of the box 700, including access to the inner cavity. Referring to FIG. 46, the internal processing unit 736 is located within the housing, and in an exemplary embodiment may be located between the bottom side 720 of the housing 710 and the inner cavity 724. The internal processing unit may comprise a single board computer (SBC) associated with a printed circuit board (PCB). In an exemplary embodiment, the SBC may be a Raspberry PI Model 3, although other embodiments may use a variety of commercially-available processing units to perform the same functions. The SBC includes wireless capabilities that permit wireless connectivity to a wireless network via an external wireless antenna 741 located on the box 700. While shown in FIGS. 38-42, the wireless antenna 741 is not shown in FIGS. 43-46. The PCB may interface the low voltage signals of the SBC with the other devices, including an RFID radio module connected directly to the PCB, the electromechanical lock access mechanisms 732, 734, the access reader unit 737 located on the right side of the housing, and the LED light 750.

The access reader unit 737 is the source of authentication for the electronic actuation of the lock access mechanisms 732, 734. In some embodiments, the access reader unit 737 may be a proximity card reader. The PCB is also in electronic communication with an RFID antenna 743 located in the housing 710 of the box 700. As illustrated in FIGS. 45B and 46, the RFID antenna 734 is located between the back side 722 of the housing the inner cavity 724. The RFID antenna 734 may be connected by coaxial cable to an RFID reader module connected to PCB. In an exemplary embodiment, the RFID reader module may be a ThingMagic Micro Embedded RFID Reader Module, however in other embodiments a variety of other commercially-available RFID reader modules may be used.

As with other embodiments disclosed herein, one or more wires (not shown) may be used to facilitate communication between the various components of the box 700 and the internal processing unit, as well as supply power. The box 710 may be mains-powered and may be powered by PoE or other means. Referring to FIG. 46, an internal power supply 760 is also shown.

One or ordinary skill in the art will recognize that any location, variation, or combination of RFID antenna and RFID readers is contemplated, including versions described in other embodiments herein. Additionally, although a single antenna may be used to scan the entire volume of the inner cavity 724, in other embodiments multiple antennas, readers, or antenna/readers may be used to read RFID tags located in the box 700.

Referring to FIGS. 41-45, located on the top side 718 of the box is a lockable drop box mechanism 744. The drop box mechanism 744 comprises a pivotable drawer 746 with a finger slot 748 that allows for manual opening of the drawer 746 when the drawer 746 is in a closed and unlocked state. The drawer 746 allows items to be placed into the inner cavity 724 of the box 700 when the inner door 730 is closed. When the drawer 746 is in an open position an item can be placed into the drawer 746 by a user. The drawer 746 can then be manually pushed into a closed position, when the item will drop into the inner cavity 724. The drawer 746 may also close shut under the force of gravity, such that it is only in an open position when a user is holding it open. In some embodiments, the drawer 746 may have a lip, handle, knob, or other feature that aids a user in opening and closing the drawer 746. In some embodiments, the drop box mechanism 744 may be automated such that the opening and closing of the drawer 746 can be initiated by manipulating a button or switch.

Figure 45C:
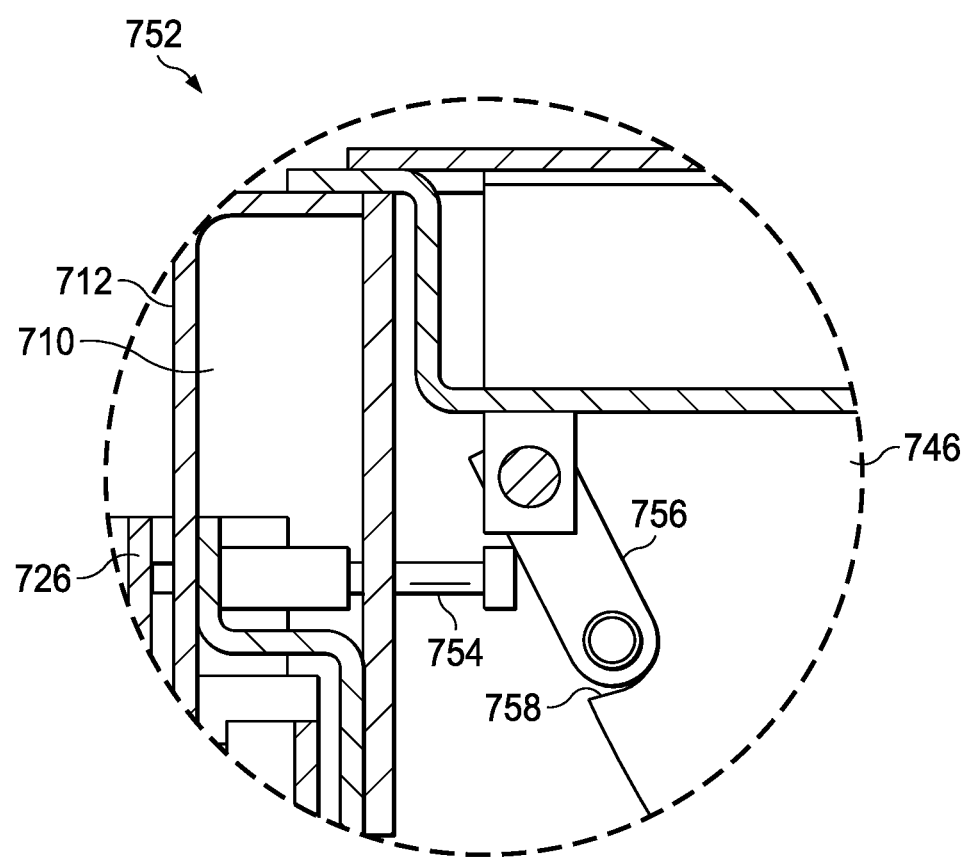
FIG. 45C is a side sectional view of Detail B shown in FIG. 45B.
Figure 46:
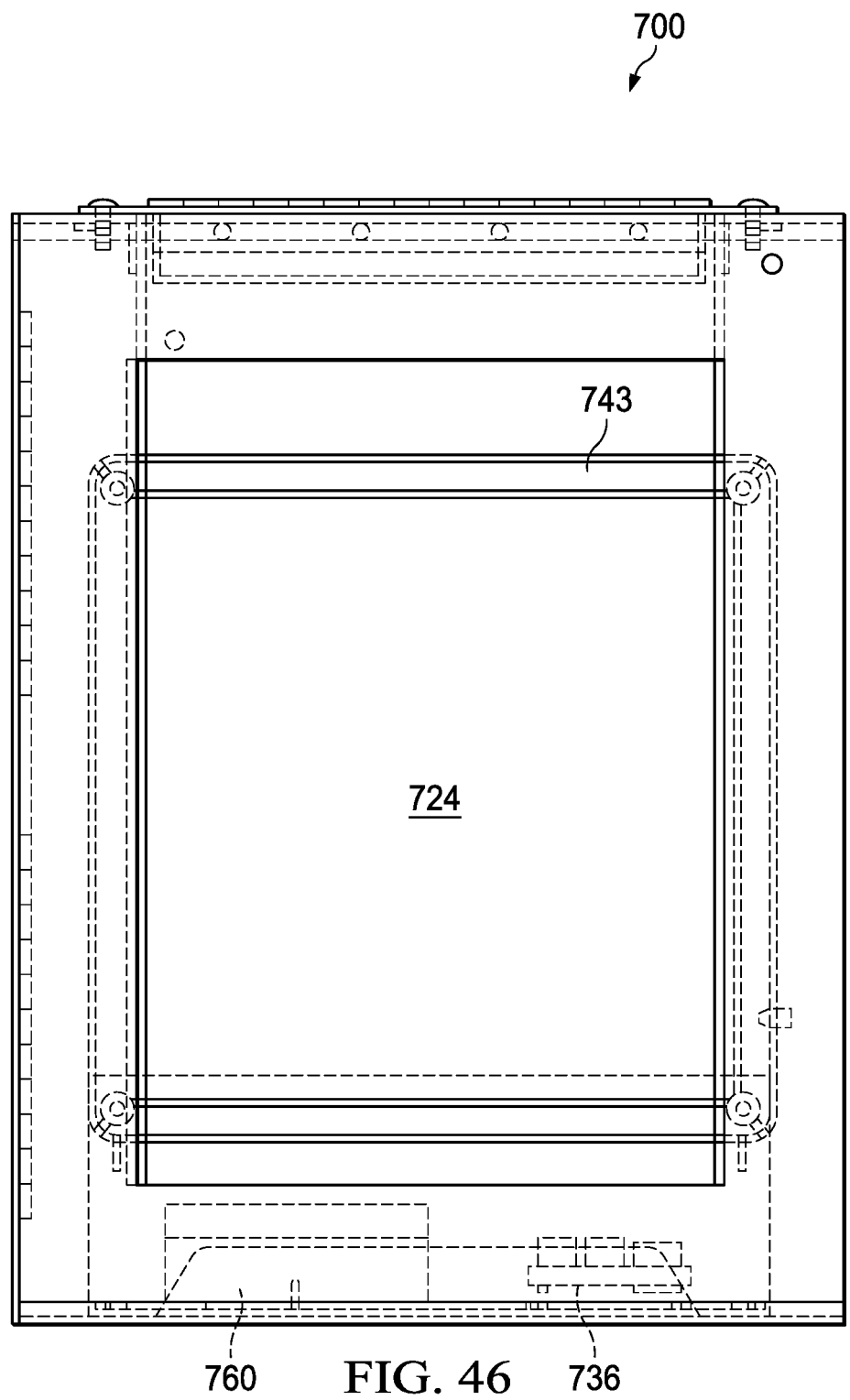
FIG. 46 is a front elevational view of the exemplary embodiment of FIG. 38 with transparency.

As illustrated in FIGS. 45B and 45C, the drop box 746 may contain a locking mechanism 752 that prevents the drawer from being opened when the inner door 730 is locked. In an exemplary embodiment, the locking mechanism 752 is comprised of a pin 754 that extends into the inner cavity 724 through the front side of the housing 712. The pin 754 is a spring pin biased to extend out of the front side of the housing 712 (its "initial" position). When the outer door 726 is in a closed position, the back side of the outer door 726 forces the pin 754 to move from its initial position into an extended position where the pin 754 shifts further into the inner cavity 724. In some exemplary embodiments, the outer door 726 may have a protrusion on its back side that lines up with the pin 754 when the outer door 726 is in the closed position and helps to push the pin 754 into an extended position when the door 726 is closed.

In its extended position, the pin 754 makes contact with a lever 756 connected to said housing 710 and forces the lever 756 to engage with a slot 758 located on the drawer 746. The lever 756 is spring loaded and biased into a position that is disengaged from the slot 758. When the pin 754 is extended, the engagement of the lever 756 into the slot 758 prevents the drawer 746 from being opened from the top side of the box 700. When the outer door 726 opens, the pin 754 springs from the extended position back to its initial position. Returned to its initial position the pin 754 is no longer in contact with the lever 756, and the lever 756 springs into a disengaged position in which it is no longer engaged with the slot 758 on the drawer 746. Accordingly, the drop box 744 can be opened by a user, who can then drop items into the inner cavity 724 using the drawer 746.

In other embodiments, an electrical locking mechanism may secure the drawer 746 in a closed position by being insertably received into the surrounding housing 710 when in a locked state. In such an embodiment the locking mechanism may be in electronic communication with the PCB, which controls the locking and unlocking of the drawer 746.

The drop box mechanism 744 may be useful in scenarios where there is far more concern about the removal of items from the box 700 than the addition of items to the box 700. Also, the drop box 744 allows for more flexibility in dropping in items as there is not the same need for authorized users as there is to access the inner cavity 724. That is, in an exemplary embodiment there only needs to be authorization for the opening of the outer door 726. In an exemplary scenario, a drug kit could be returned to the box 700 at the end of a shift or work day without requiring an authorized supervisor to open the inner door 730.

Although the exemplary embodiment of FIGS. 38-43 includes a drop box mechanism, in some embodiments of the double door RFID box there may be no drop box mechanism.

The RFID box includes means for visually indicating alerts to a user. A tri-colored LED (light emitting diode) 750 may be located the front side of the housing. In the exemplary embodiment of FIGS. 38-43 the LED 750 is located in the upper right hand portion of the front side of the housing 712, but in other embodiments the exact location may vary. Different colors and/or patterns of light may be emitted to communication information including, but not limited to, the status of contents, access, and user authorization. In other embodiments, multiple LED lights may be used, or even a small display screen may be located on outside of the box 700 in order to convey information to users. For example, the LED light may be programmed to be red until access is granted to an authorized user, at which time the light may change to green. As another example, the light may turn yellow to indicate that an item has been removed from the box. In another example, the light may change color to indicate that an inventory scan has detected items that are expired.

The double door RFID box 700 may be used to control access to narcotics or other controlled substances or expensive drugs that require security. The housing 710 and doors 726, 730 may be made of durable steel construction, and two different authorized users may need to be recognized by the system before both doors can be opened and the interior cavity 724 accessed. Authorized users may be recognized by pre-approved RFID IDs associated with RFID cards, RFID bracelets, or other RFID items that may be carried by a user. The need for two authorized users in order to access the inner cavity 724 of the box (each being authorized to open a single door) may satisfy security requirements in a hospital, medical facility, emergency medical service facility, fire station, or other facility that follows high-security protocols for securing and accessing narcotics or other drugs.

Operations of the box 700 are performed by software located on the internal processing unit 736, including the PCB, as well as software located on a remote server accessible over a network. In an exemplary embodiment, configuration of access levels, permissions, notifications, box content/inventory tracking, audit recording, and RFID maintenance levels may be performed by the remote server. In some embodiments the remote server may be a cloud based data storage and processing server. In other embodiments the remote server may simply be located on a local network within the same facility or campus. In other embodiments the internal processing unit may instead perform some or all of these functions, allowing the box 700 greater autonomy to perform various tasks even when not connected to a wireless network In an embodiment where the internal processing server performs all functions, including maintaining its own database, there may be no need for a remote server.

In an exemplary embodiment where a remote server is used, the remote server is associated with a database that stores the baseline box content data and updates it with the current box content data after each scan. Content data is provided by scans of RFID tags within the internal cavity, although the system may also allow manual entry of content data as well when necessary.

The remote server also stores information regarding authorized users, authorization levels, and the audit records for each box. Although a certain user, associated with a specific RFID card, may have authorization to open the outer door, they may not be authorized to open the inner door. In some embodiments there may be no authorization levels, just a requirement that two separate authorized users, as identified by their RFID cards, open each of the doors.

A user on a remote device can change authorization levels and perform RFID maintenance using an online portal supported by the remote server. A remote user device could be a personal computer, a cell phone, or any other electronic device able to access the online portal. The remote server can also push alerts and notifications to user devices when certain activities occur. For example, if the box is accessed by an authorized user, a supervisor may receive a text message letting them know who has accessed the contents of the box, what time the box was accessed, and what items, if any, were taken from the box. A user could receive a text message or email at the end of each day letting them know the current contents of the box, and whether any items are expired or under recall. One of ordinary skill in the art will appreciate that many types of alerts and notifications may be communicated to users in a variety of ways including email, text message, fax, or even automated voicemail. Furthermore, a user may check on the status of a particular box at any time by accessing an online portal using a variety of devices. Again, the operations described herein, and more, may be performed by the internal processing unit in an exemplary embodiment that does not require a remote server.

In an exemplary scenario, the RFID box 700 is stocked with one or more items and both the outer door 726 and inner door 730 are locked. The drop box mechanism 744 is shut and locked. A first RFID card associated with a first authorized user account is placed in close enough proximity to the access reader unit 737 that it is detected. The access reader unit 737 communicates with the PCB in the internal processing unit, which communicates the RFID information with the remote server over a wireless network. The remote server compares the RFID information presented by the internal processing unit with RFID information stored in a database. If authorization is confirmed, the internal processing unit directs the lock access mechanism 732 on the outer door 726 to unlock, allowing the outer door 726 to be opened by a user. In some embodiments the hinge mechanisms 728 on the outer and inner doors 726, 730 may include biased springs that cause the door to swing open once unlocked. The internal processing unit also directs the locking mechanism for the drop box 744 to unlock so that a user can open the drawer 746 via the finger slot 748 and drop in any items as desired.

In order to open the inner door 730, a second RFID card associated with a second authorized account is placed in close enough proximity to the access reader unit 737 that it is detected. The access reader unit 737 again communicates with the PCB in the internal processing unit, which directs the request to the remote server. If authorization is granted, the PCB directs the lock access mechanism 734 on the inner door 730 to unlock, allowing the inner door 730 to be opened by a user or swing open. A user may then access the contents of the inner cavity 724.

An audit trail of which user accounts were read by the access reader unit 737 is stored by the remote server. Records stored by the remote server may include which users requested access to the box, what time access was sought, and whether such access was granted or denied. In a system where there are two or more boxes, the audit trail will also include information identifying which specific box was accessed. The remote server may push notifications and/or alerts out to users to notify them of who has requested access to the box and/or received authorization. The remote server may also transmit such information to a remote portal to be accessed by users on a variety of electronic devices.

When both doors are shut, the latches re-engage with the respective apertures in the housing. In other embodiments, the doors may not automatically lock once fully shut, and may require the use of an authorized RFID card to relock.

Once both doors are shut, the internal processing unit may initiate a scan of the inner cavity 724 to detect RFID tags. The results of the scan are transmitted from the computer to the remote server containing a database of information related to previously-scanned items. The remote server compares the scan results to the last scan to determine if any items are missing and if any new items are present. Any expired or recalled items may also be identified. Notifications regarding missing items, new items, or users may be communicated from the remote server. Items determined to be missing may be noted on the audit trail. For example, the audit trail may identify that at 12:43 pm on a particular day, user A was granted access through the inner door and removed two unit doses of Hydrocodone tablets from box A. The audit trail may also identify that user B was granted access to the outer door at 12:00 pm on that same day. The audit trail could also show that user C sought access through the inner door at 12:30 pm on the same day and was denied. The audit trail could further show that at 12:50 on that day, user D sought access through the inner door, which was granted, and left two unit doses of Fentanyl in the inner cavity.

It will be appreciated by one of ordinary skill in the art that various forms of software and hardware could be used. In exemplary embodiments where there is no remote server, the internal processing unit stores all information, including information pertaining to authorized users, audit records, inventory, content. The internal processing unit is able to push notifications and alerts to users, and can support a web portal. Variations including those systems described in other embodiments herein may be used as desired without departing from the inventive concept.

In an exemplary embodiment, the drop box may include a micro switch that can signal to the internal computer that an item has been deposited into the inner cavity through the drop box and an inventory scan needs to be performed in order to update content data. In such an embodiment, the box will be able to send alerts and notifications regarding items that have been dropped into the drop box, and will not wait for updates when the outer door is closed.

In an exemplary embodiment, the box may initiate notifications if the doors have been opened for a certain amount of time, in order to increase security. This may be achieved through the use of micro switches located on each of the doors. This may also be achieved through the internal processing unit tracking the locking and unlocking of both doors.

In an exemplary embodiment, there may not be double doors, but instead a single door for accessing the internal cavity. Authorization requirements would vary accordingly, as only one authorized user would be needed to open this embodiment of the box. However, in this embodiment the box may still have a drop box mechanism and any of the other features described herein for the double door RFID box. A single door box may be beneficial to support delivery confirmation in a hospital or other large facility setting where drugs that are not narcotics or otherwise subject to the highest standards of security are moved around the facility on a daily basis. A single door box may be used as a receptacle to hold such drugs temporarily, yet still serve the function of tracking the location of the drug, who dropped it off, at what time it was dropped off, and similar information regarding when it is removed.

Two or more RFID box devices according to the exemplary embodiments described herein may be used together in the same system to track the location of items and user access/authorization. A multi-device system may be used in a hospital or large clinical setting where drugs are routinely moved from one location to another depending upon specific needs. For example, a hospital with a pharmacy unit that sends drugs to various hospital floors throughout the day for eventual use. In an exemplary embodiment of a multi-device system, the system may not only detect the removal of items from one RFID box, but identify when those same items are deposited in a second RFID box at a later time. The system may also track, record, and report the time interval between the removal of an item from one device and the deposit of the same item in another device. A common remote server in communication with each RFID box may provide authorizations, track overall and individual inventories, and monitor the operations of each box and send notifications and alerts. Each device may have a unique identifier with the remote server that is associated with information regarding the specific location of each device and any other features particular to each device. Accordingly, if a user receives a notification that a certain item has been taken from a particular device, they will know where in the facility that device is, and accordingly the last physical location of the item.

Although one or more double door RFID boxes may be part of a multi-device system, in various embodiments different combinations of RIFD boxes according to other embodiments of RFID boxes identified herein may be used.

One of ordinary skill in the art will recognize that any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A device for securing and tracking RFID-tagged inventory comprising:
    a housing surrounding an interior cavity, said housing having a front side, a top side, a left and right side, a bottom side, and a back side;
    an outer door, said outer door connected to said front side of said housing, and said outer door adapted for movement between a closed position and an open position;
    an inner door, said inner door adapted for movement between a closed position and an open position;
    a drop box mechanism located in said top side of said housing, said drop box mechanism comprising a drawer adapted to move between an open position and a closed position, said drawer adapted to receive items when said drawer is in said open position, and said drawer adapted to place items into said inner cavity when said drawer is in said closed position;
    an RFID antenna located within said housing; said RFID antenna configured to communicate with one or more RFID tags located within said interior cavity;
    an RFID reader located within said housing, said RFID reader configured to communicate with one or more RFID tags located within said interior cavity; and
    a processor located within said housing, said processor in electronic communication with said RFID antenna and said RFID reader;
    wherein said drop box mechanism is associated with said outer door such that said drawer is prevented from moving to said open position when said outer door is closed; and
    wherein said processor is adapted to instruct said RFID antenna and said RFID reader to perform a scan to identify items present in said interior cavity upon the closing of said outer door.

2. The device of claim 1, wherein said inner door is located in a recess in said front side of said housing.

3. The device of claim 1, wherein said outer and inner doors are spring biased in an open position.

4. The device of claim 1, wherein said device further comprises:
    an LED light located on said housing, said LED light adapted to communicate notifications to a user.

5. The device of claim 1, wherein said inner door is located behind said outer door and said inner door can only be in an open position when said outer door is in an open position.

6. The device of claim 1, wherein said outer door and inner door comprise lips adapted to aid a user in manually opening and closing said doors.

7. The device of claim 1, further comprising:
    a first lock mechanism associated with said outer door, said first lock mechanism in electronic communication with said processor;
    a second lock mechanism associated with said inner door, said second lock mechanism in electronic communication with said processor;
    an access reader unit; said access reader unit in electronic communication with said processor, said access reader unit adapted to recognize RFID cards associated with authorized users;
    wherein said processor is adapted to direct said first electromechanical lock mechanism to unlock said outer door upon the recognition by said access reader unit of a first RFID card associated with a first authorized user, and said processor is adapted to direct said first electromechanical lock mechanism to unlock said outer door upon the recognition by said access reader unit of a second authorized RFID card associated with a second authorized user.

8. The device of claim 7, wherein said first and second lock mechanisms comprise mechanical manual override locks.

9. The device of claim 1, further comprising:
    a locking mechanism adapted to lock said drawer in said closed position, said locking mechanism comprising:
    a slot, said slot located on said drawer;
    a lever, said lever connected to said housing, said lever spring positioned to engage with said slot when said drawer is in said closed position; said lever spring loaded and biased in a position disengaged from said slot; and
    a spring pin, said spring pin extending through said front side of said housing, said spring pin biased to extend out of said front side of said housing; said spring pin adapted to slide through said housing and make contact with said lever when said outer door is moved from said open position to said closed position;
    wherein when said outer door is closed and said pin engages with said lever, said lever engages with said slot and prevents said drawer from being opened.

10. The device of claim 1, wherein said drawer includes a finger slot for opening said drawer.

11. A device for securing and tracking RFID-tagged inventory comprising:
- a housing surrounding an interior cavity, said housing having a front side, a top side, a left and right side, a bottom side, and a back side;
- a door, said door connected to the front side of said housing, and said door adapted for movement between a closed position and an open position;
- a drop box mechanism located in said top side of said housing, said drop box mechanism comprising a drawer adapted to move between an open position and a closed position, said drawer adapted to receive items when said drawer is in said open position, and said drawer adapted to place items into said inner cavity when said drawer is in said closed position;
- an RFID antenna located within said housing; said antenna configured to communicate with one or more RFID tags located within said interior cavity;
- an RFID reader located within said housing, said reader configured to communicate with one or more RFID tags located within said interior cavity; and
- a processor located within said housing, said processor in electronic communication with said at least one RFID antenna and said at least one RFID reader;
- wherein said drop box mechanism is associated with said door such that said drawer is prevented from moving to said open position when said door is closed; and
- wherein said processor is adapted to instruct said at least one RFID antenna and said at least one RFID antenna/reader to perform a scan to identify items present in said interior cavity upon the closing of said door.

12. The device of claim 11, wherein said device further comprises an LED light located on said housing, said LED light adapted to communicate notifications to a user.

13. The device of claim 11, wherein said door is spring biased in said open position.

14. The device of claim 11, further comprising:
- a first lock mechanism associated with said door, said first lock mechanism in electronic communication with said processor;
- an access reader unit; said access reader unit in electronic communication with said processor, said access reader unit adapted to recognize an RFID card associated with an authorized user;
- wherein said processor is adapted to direct said lock mechanism to unlock said door upon the recognition by said access reader unit of an RFID card associated with an authorized user.

15. The device of claim 14, wherein said first lock mechanism comprises an electronically actuated lock in communication with said processor.

16. The device of claim 14, wherein said first lock mechanism comprises a mechanical manual override lock.

17. The device of claim 11, further comprising:
- a second lock mechanism adapted to lock said drawer in said closed position, said second lock mechanism comprising:
  - a slot, said slot located on said drawer;
  - a lever, said lever connected to said housing, said lever spring positioned to engage with said slot when said drawer is in said closed position; said lever spring loaded and biased in a position disengaged from said slot; and
  - a spring pin, said spring pin extending through said front side of said housing, said spring pin biased to extend out of said front side of said housing; said spring pin adapted to slide through said housing and make contact with said lever when said door is moved from said open position to said closed position;
- wherein said lever is adapted to engage with said slot and prevent said drawer from being opened when said door is closed.

18. The device of claim 11, wherein said drawer comprises a finger slot for opening said drawer.

* * * * *